US011857770B2

(12) United States Patent
Byerly et al.

(10) Patent No.: US 11,857,770 B2
(45) Date of Patent: Jan. 2, 2024

(54) MEDICATION DELIVERY DEVICE WITH A SENSED ELEMENT

(71) Applicant: Eli Lilly and Company, Indianapolis, IN (US)

(72) Inventors: Roy Howard Byerly, Indianapolis, IN (US); Timothy Mark Blum, Columbus, OH (US)

(73) Assignee: Eli Lilly and Company, Indianapolis, IN (US)

( * ) Notice: Subject to any disclaimer, the term of this patent is extended or adjusted under 35 U.S.C. 154(b) by 664 days.

(21) Appl. No.: 16/968,425

(22) PCT Filed: Feb. 20, 2019

(86) PCT No.: PCT/US2019/018757
§ 371 (c)(1),
(2) Date: Aug. 7, 2020

(87) PCT Pub. No.: WO2019/164936
PCT Pub. Date: Aug. 29, 2019

(65) Prior Publication Data
US 2020/0397996 A1    Dec. 24, 2020

Related U.S. Application Data

(60) Provisional application No. 62/779,652, filed on Dec. 14, 2018, provisional application No. 62/633,655, filed on Feb. 22, 2018.

(51) Int. Cl.
*A61M 5/315* (2006.01)
(52) U.S. Cl.
CPC .... *A61M 5/31528* (2013.01); *A61M 5/31551* (2013.01); *A61M 5/31568* (2013.01);
(Continued)

(58) Field of Classification Search
CPC .......... A61M 5/31551; A61M 5/31568; A61M 5/31585; A61M 5/31593
See application file for complete search history.

(56) References Cited

U.S. PATENT DOCUMENTS 5,536,249 A    7/1996  Castellano et al.
5,820,602 A   10/1998  Kovelman et al.
(Continued)

FOREIGN PATENT DOCUMENTS

EP    1074273 B1    9/2004
EP    1353715 B1    5/2005
(Continued)

OTHER PUBLICATIONS

Screen capture from YouTube video clip entitled "*KwikPen: for injecting Humalog, Humalog Mix 25 and Humalog Mix 50*", (at 2:03 of 3:00), 1 page, uploaded on Feb. 13, 2011 by user "manjanest", EndoDiabetes.com video, 2011, Retrieved from Internet: https://www.youtube.com/watch?v=rMCg1Lp2q-w.
(Continued)

*Primary Examiner* — Dung T Ulsh
(74) *Attorney, Agent, or Firm* — M. Daniel Spillman

(57)    ABSTRACT

A medication delivery device including a device body and a dose setting component coupled to the device body. Component is rotatable relative to the device body in relation to an amount of a set or delivered dose. An annular sensed element, such as a metal or magnetic ring, is positioned on a proximal surface of the dose setting component. A carrier secures the sensed element to the dose setting component. The carrier includes a proximal overlapping support that is contactable against the sensed element opposite the proximal surface of the dose setting component. The carrier is configured to axially and rotationally fix the sensed element (Continued)

to the dose setting component. The device may include a dose detection system operable with the sensed element.

25 Claims, 30 Drawing Sheets

(52) U.S. Cl.
CPC .... *A61M 5/31585* (2013.01); *A61M 5/31593* (2013.01); *A61M 2205/3306* (2013.01); *A61M 2205/3317* (2013.01); *A61M 2205/3327* (2013.01)

(56) References Cited

U.S. PATENT DOCUMENTS

| | | | |
|---|---|---|---|
| 6,248,090 B1 | 6/2001 | Jensen et al. | |
| 6,287,283 B1 | 9/2001 | Ljunggreen et al. | |
| 6,585,698 B1 | 7/2003 | Packman et al. | |
| 6,999,890 B2 | 2/2006 | Kai | |
| 7,008,399 B2 | 3/2006 | Larsen et al. | |
| 7,291,132 B2 | 11/2007 | DeRuntz et al. | |
| 7,511,480 B2 * | 3/2009 | Steffen | A61M 5/31556 324/207.21 |
| 7,534,230 B2 | 5/2009 | Follman et al. | |
| 7,713,229 B2 | 5/2010 | Veit et al. | |
| 7,772,835 B2 | 8/2010 | Dmytriw et al. | |
| 8,181,849 B2 | 5/2012 | Bazargan et al. | |
| 8,385,972 B2 | 2/2013 | Bochenko et al. | |
| 8,560,271 B2 | 10/2013 | Koehler et al. | |
| 8,638,108 B2 | 1/2014 | Nielsen et al. | |
| 8,734,394 B2 | 5/2014 | Adams et al. | |
| 8,771,233 B2 | 7/2014 | Watanabe et al. | |
| 8,882,704 B2 | 11/2014 | Fago et al. | |
| 8,894,611 B2 | 11/2014 | Larsen et al. | |
| 9,022,988 B1 | 5/2015 | Shaban | |
| 9,089,650 B2 | 7/2015 | Nielsen et al. | |
| 9,125,991 B2 | 9/2015 | Schabbach et al. | |
| 9,186,465 B2 | 11/2015 | Jorgensen et al. | |
| D770,038 S | 10/2016 | Ahlgrim et al. | |
| 9,604,004 B2 | 3/2017 | Jakobsen | |
| 9,623,188 B2 | 4/2017 | Nielsen et al. | |
| 9,775,957 B2 | 10/2017 | Despa et al. | |
| 9,782,543 B2 | 10/2017 | Groeschke et al. | |
| 9,782,544 B2 | 10/2017 | Heumann et al. | |
| 9,943,647 B2 | 4/2018 | Mukai et al. | |
| 10,010,678 B2 | 7/2018 | Schildt et al. | |
| 10,016,567 B2 | 7/2018 | Denyer et al. | |
| 10,155,090 B2 | 12/2018 | Larsen et al. | |
| 10,173,020 B2 | 1/2019 | Sutherland et al. | |
| 10,383,996 B2 | 8/2019 | Miller et al. | |
| 10,391,235 B2 | 8/2019 | Schabbach et al. | |
| 10,682,469 B2 | 6/2020 | Jakobsen et al. | |
| 2003/0065536 A1 | 4/2003 | Hansen et al. | |
| 2005/0038407 A1 | 2/2005 | Sumka | |
| 2006/0175427 A1 | 8/2006 | Jonientz et al. | |
| 2008/0167615 A1 | 7/2008 | Niehoff | |
| 2009/0318865 A1 | 12/2009 | Moller et al. | |
| 2012/0072236 A1 | 3/2012 | Atkin | |
| 2013/0079727 A1 | 3/2013 | Schildt et al. | |
| 2014/0005950 A1 | 1/2014 | Groeschke et al. | |
| 2014/0194826 A1 | 7/2014 | Nielsen et al. | |
| 2014/0194829 A1 | 7/2014 | Baek et al. | |
| 2014/0276583 A1 | 9/2014 | Chen et al. | |
| 2015/0025470 A1 | 1/2015 | Baran et al. | |
| 2015/0202375 A1 | 7/2015 | Schabbach et al. | |
| 2015/0202376 A1 | 7/2015 | Haupt | |
| 2015/0246179 A1 | 9/2015 | Zur et al. | |
| 2015/0290396 A1 | 10/2015 | Nagar et al. | |
| 2015/0352288 A1 | 12/2015 | Andersen | |
| 2015/0356273 A1 | 12/2015 | Cave | |
| 2016/0030679 A1 * | 2/2016 | Nielsen | G16H 20/17 604/189 |
| 2016/0051760 A1 | 2/2016 | Krusell et al. | |
| 2016/0051764 A1 | 2/2016 | Dreier et al. | |
| 2016/0074587 A1 | 3/2016 | Searle et al. | |
| 2016/0213853 A1 | 7/2016 | Despa et al. | |
| 2016/0235925 A1 | 8/2016 | Kuhn et al. | |
| 2016/0239610 A1 | 8/2016 | Andersen | |
| 2016/0259913 A1 | 9/2016 | Yu et al. | |
| 2016/0263324 A1 | 9/2016 | Shaanan et al. | |
| 2016/0287804 A1 | 10/2016 | Madsen et al. | |
| 2016/0331906 A1 | 11/2016 | Harms et al. | |
| 2016/0378951 A1 | 12/2016 | Gofman et al. | |
| 2017/0068799 A1 | 3/2017 | Mensinger et al. | |
| 2017/0124284 A1 | 5/2017 | McCullough et al. | |
| 2017/0124285 A1 | 5/2017 | McCullough et al. | |
| 2017/0232203 A1 | 8/2017 | Krusell | |
| 2017/0235920 A1 | 8/2017 | Bauss et al. | |
| 2017/0274149 A1 | 9/2017 | Aeschlimann | |
| 2017/0286638 A1 | 10/2017 | Searle et al. | |
| 2018/0008778 A1 | 1/2018 | Erbstein | |
| 2018/0036484 A1 | 2/2018 | Andersen | |
| 2018/0099084 A1 | 4/2018 | Schabbach et al. | |
| 2018/0154086 A1 | 6/2018 | Toporek et al. | |
| 2018/0157803 A1 | 6/2018 | Mirov | |
| 2018/0165422 A1 | 6/2018 | Mirov | |
| 2018/0225560 A1 | 8/2018 | Schneider et al. | |
| 2018/0243511 A1 | 8/2018 | Gylleby et al. | |
| 2018/0280624 A1 | 10/2018 | Bitton et al. | |
| 2018/0296767 A1 | 10/2018 | Säll | |
| 2018/0326164 A1 | 11/2018 | Bauss et al. | |
| 2019/0022328 A1 | 1/2019 | Schleicher et al. | |
| 2019/0022330 A1 | 1/2019 | Schleicher et al. | |
| 2019/0262541 A1 * | 8/2019 | Christensen | G02B 5/208 |
| 2021/0008287 A1 * | 1/2021 | Jugl | G16H 20/17 |

FOREIGN PATENT DOCUMENTS

| | | | |
|---|---|---|---|
| EP | 3042676 | 7/2016 | |
| EP | 3103492 | 12/2016 | |
| EP | 2945665 | 3/2018 | |
| EP | 3517153 | 7/2019 | |
| GB | 2256050 A | 11/1992 | |
| JP | H08164206 A | 6/1996 | |
| JP | 2010525869 A | 7/2010 | |
| JP | 2013228313 A | 11/2013 | |
| WO | 9009202 | 8/1990 | |
| WO | 1999015214 A1 | 4/1999 | |
| WO | 2002064196 A1 | 8/2002 | |
| WO | 2002092153 A1 | 11/2002 | |
| WO | 2003047426 A1 | 6/2003 | |
| WO | 2004078241 A1 | 9/2004 | |
| WO | 2005009231 A1 | 2/2005 | |
| WO | 2006069455 A1 | 7/2006 | |
| WO | 2007107564 A1 | 9/2007 | |
| WO | 2009062675 A1 | 5/2009 | |
| WO | 2009132777 | 11/2009 | |
| WO | 2010098927 A2 | 9/2010 | |
| WO | 2010098928 A1 | 9/2010 | |
| WO | 2010098929 A1 | 9/2010 | |
| WO | 2010098931 A1 | 9/2010 | |
| WO | 2010112575 A1 | 10/2010 | |
| WO | 2010142598 A1 | 12/2010 | |
| WO | 2012046199 A1 | 4/2012 | |
| WO | 2013120778 A1 | 8/2013 | |
| WO | 2014037331 A1 | 3/2014 | |
| WO | 2014111340 | 7/2014 | |
| WO | 2015189170 | 12/2015 | |
| WO | 2016014365 A1 | 1/2016 | |
| WO | 2016120207 | 8/2016 | |
| WO | 2016128426 | 8/2016 | |
| WO | 2016131713 | 8/2016 | |
| WO | 2016142216 | 9/2016 | |
| WO | 2016142727 | 9/2016 | |
| WO | 2016155997 | 10/2016 | |
| WO | 2016193229 | 12/2016 | |
| WO | 2016198516 | 12/2016 | |
| WO | WO-2016198516 A1 * | 12/2016 | ........ A61M 5/31528 |
| WO | 2017013463 | 1/2017 | |
| WO | 2017013464 | 1/2017 | |
| WO | 2017032586 | 3/2017 | |
| WO | 2017050781 | 3/2017 | |
| WO | 2017097507 | 6/2017 | |

(56) References Cited

FOREIGN PATENT DOCUMENTS

| WO | 2017108312 | 6/2017 |
| WO | 2017148855 | 9/2017 |
| WO | 2017153105 | 9/2017 |
| WO | 2017200989 | 11/2017 |
| WO | 2018013419 | 1/2018 |
| WO | 2018046680 | 3/2018 |
| WO | 2018104289 | 6/2018 |
| WO | 2018104292 | 6/2018 |
| WO | 2018138542 | 8/2018 |
| WO | 2018160425 | 9/2018 |
| WO | 2019001919 | 1/2019 |
| WO | 2019018793 | 1/2019 |
| WO | 2019057911 | 3/2019 |
| WO | 2019057916 | 3/2019 |
| WO | 2019164936 | 8/2019 |

OTHER PUBLICATIONS

Screen capture from YouTube video clip entitled "*Injecting Insulin With the Lantus SoloSTAR Pen*", (at 5:49 of 10:07), 1 page, uploaded on Oct. 29, 2012 by user " '胰島素", Sanofi-aventis U.S. LLC, A Sanofi Company video, 2012, Retrieved from Internet: https://www.youtube.com/watch?v=g7JLG36ZO-U.

Screen capture from YouTube video clip entitled "*How to Use Flexpen for injecting NovoMix 30, Levemir and Novorapid (Novolog) Insulins*", (at 1:25 of 2:22), 1 page, uploaded on Nov. 11, 2012 by user "manjanest", EndoDiabetes Ltd 2009 & 12 video, 2012, Retrieved from Internet: http://www.youtube.com/watch?v=KPM0P-VAQ Screen capture from YouTube video clip entitled "*How to use FlexTouch Insulin Pen for injecting Novorapid (Novolog) and Degludec (Tresiba) Insulins*", (at 1:32 of 2:27), 1 page, uploaded on Nov. 13, 2011 by user "manjanest", EndoDiabetes.com, 2011, Retrieved from Internet: https //www_youtube_com/watch?v=vKTelIngYcc.

*Screen capture from YouTube video clip entitled "How to use Humapen Savvio for Injecting Humalog, Humalog Mix 25 and 50 & Humulin I and S*", (at 1:48 of 3:01), 1 page, uploaded on Jun. 12, 2013 by user "manjanest", EndoDiabetes Ltd. video, 2013, Retrieved from Internet: http://www.youtube.com/watch?v=-gXKETYM6Fc.

Patent Cooperation Treaty International Search Report pertaining to International Application No. PCT/US2019/018780; International Filing Date: Feb. 20, 2019; dated Aug. 8, 2019.

Patent Cooperation Treaty Written Opinion of the International Searching Authority pertaining to International Application No. PCT/US2019/018780; International Filing Date: Feb. 20, 2019; dated Aug. 8, 2019.

Patent Cooperation Treaty International Search Report pertaining to International Application No. PCT/US2019/018757; International Filing Date: Feb. 20, 2019; dated Jun. 11, 2019.

Patent Cooperation Treaty Written Opinion of the International Searching Authority pertaining to International Application No. PCT/US2019/018757; International Filing Date: Feb. 20, 2019; dated Jun. 11, 2019.

\* cited by examiner

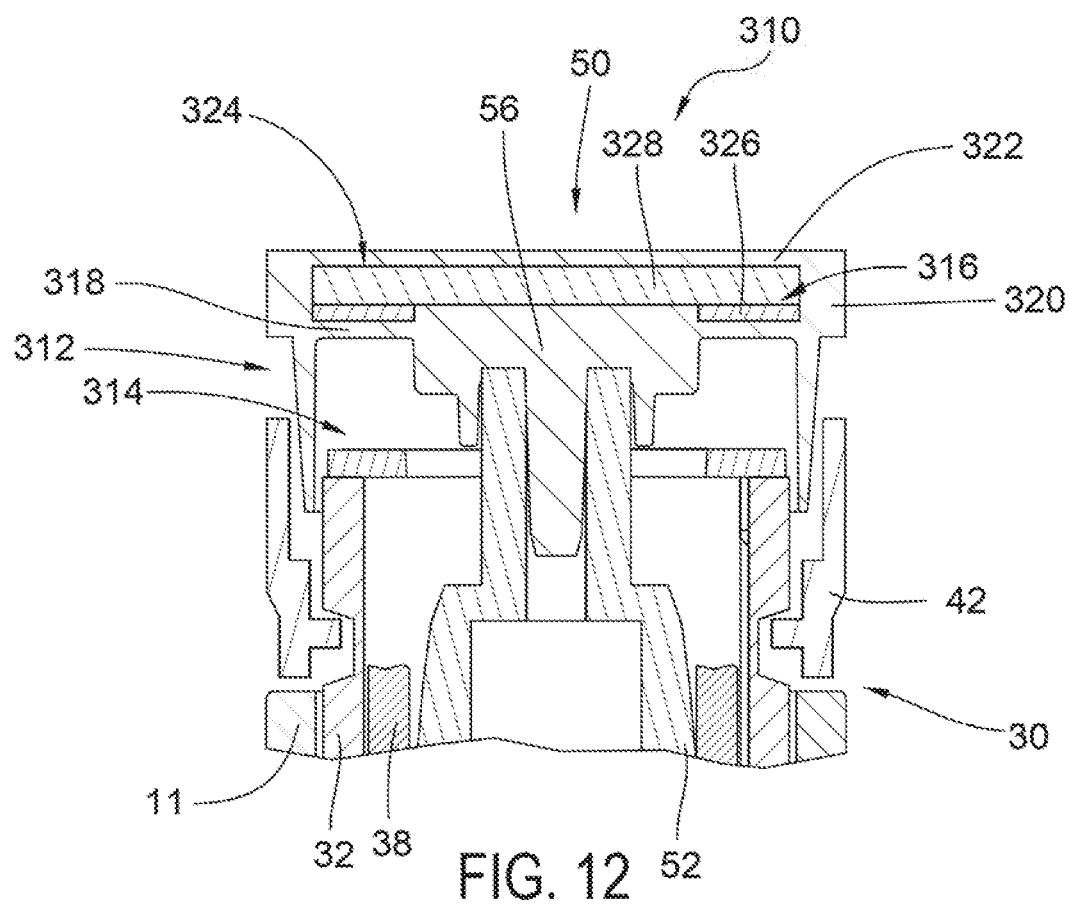

MEDICATION DELIVERY DEVICE WITH A SENSED ELEMENT

TECHNICAL FIELD

The present disclosure relates to a medication delivery device, and illustratively to a medication delivery device with a sensed element used in dose detection.

BACKGROUND

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device, and which detects the relative movement of a sensed component secured to a second member of the device.

The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by the medication delivery device during an injection event. Further, there is a need for such a dose detection device to be removable and reusable with multiple delivery devices. In other embodiments, there is a need for such a dose detection device to be integral with the delivery device.

It is also important to deliver the correct medication. A patient may need to select either a different medication, or a different form of a given medication, depending on the circumstances. If a mistake is made as to which medication is in the medication delivery device, then the patient will not be properly dosed, and records of dose administration will be inaccurate. The potential for this happening is substantially diminished if a dose detection device is used which automatically confirms the type of medication contained by the medication delivery device.

SUMMARY

In one embodiment, a medication delivery device including a rotatable sensed element that may be utilized as part of a dose detection system is disclosed. An annular sensed element, such as a metal ring, a magnetic ring, or others, is positioned on a proximal surface of a dose setting component. The dose setting component is coupled to a device body and rotatable relative thereto in relation to an amount of a set and/or delivered dose. A carrier can axially and rotationally fixed the sensed element to the dose setting component. The carrier includes a proximal overlapping support contactable against the annular sensed element opposite the proximal surface of the dose setting component. In some embodiments, the carrier may be configured with elements to help in its attachment to the dose setting component. In some embodiments, the sensed element is coupled to the dose setting member without an adhesive.

Another embodiment disclosed is a method of coupling a sensed element to a dose setting component of a medication delivery device. Steps include: providing a carrier and an annular sensed element, the carrier including a tubular body sized to fit within the annular sensed element, a proximal lip extending radially beyond the tubular body, and a plurality of coupling legs extending distally from the tubular body away from the proximal lip; coupling the annular sensed element over the tubular body of the carrier and in contact underneath the proximal lip; and coupling the carrier with the annular sensed element to the dose setting component for sandwiching the annular sensed element between the radial lip and the proximal surface of the dose setting component, where the coupling legs of the carrier is engaged with the dose setting component to rotationally lock the carrier with the annular sensed element to the dose setting component.

BRIEF DESCRIPTION OF THE DRAWINGS

The features and advantages of the present disclosure will become more apparent to those skilled in the art upon consideration of the following detailed description taken in conjunction with the accompanying figures.

FIG. 12 is cross-sectional view of a dose detection system according to another embodiment, in which the sensor and sensed element are integrated into a medication delivery device.

DETAILED DESCRIPTION

Figure 1:
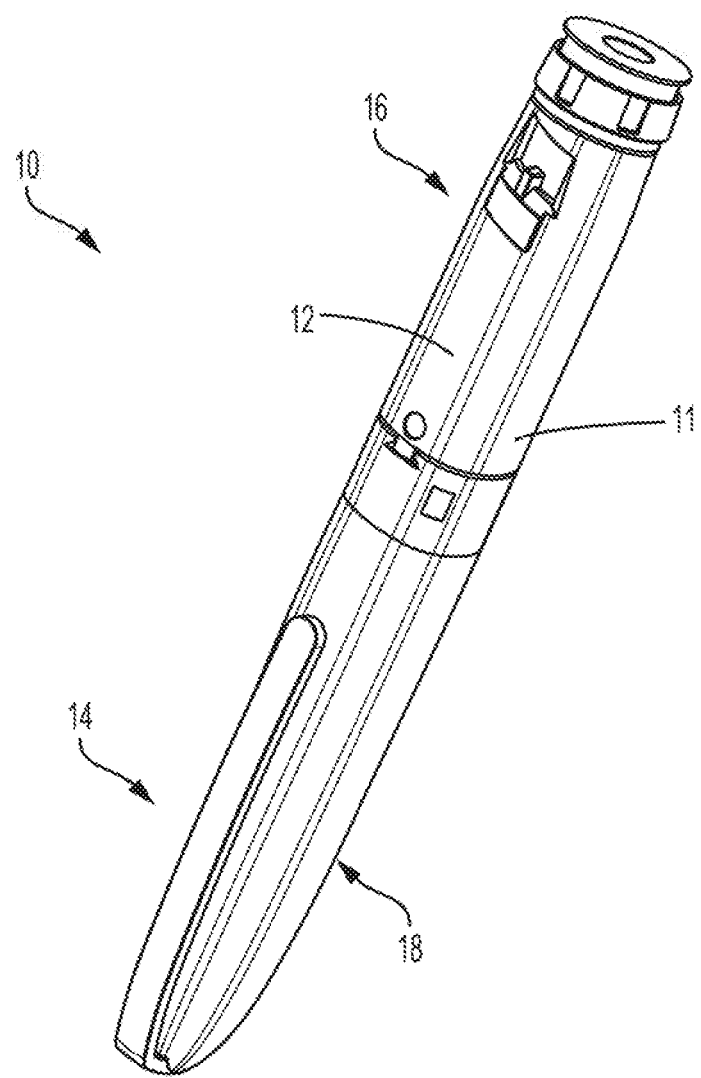
FIG. 1 is a perspective view of an exemplary medication delivery device with which the dose detection system of the present disclosure is operable.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for determining the amount of a dose delivered by a medication delivery device based on the sensing of relative rotational movement between a dose setting member and an actuator of the medication delivery device. The sensed relative angular positions or movements are correlated to the amount of the dose delivered. In a second aspect, the sensing system is for determining the type of medication contained by the medication delivery device. By way of illustration, the medication delivery device is described in the form of a pen injector. However, the medication delivery device may be any device which is used to set and to deliver a dose of a medication, such as an infusion pump, bolus injector or an auto injector device. The medication may be any of a type that may be delivered by such a medication delivery device.

Devices described herein, such as a device 10, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
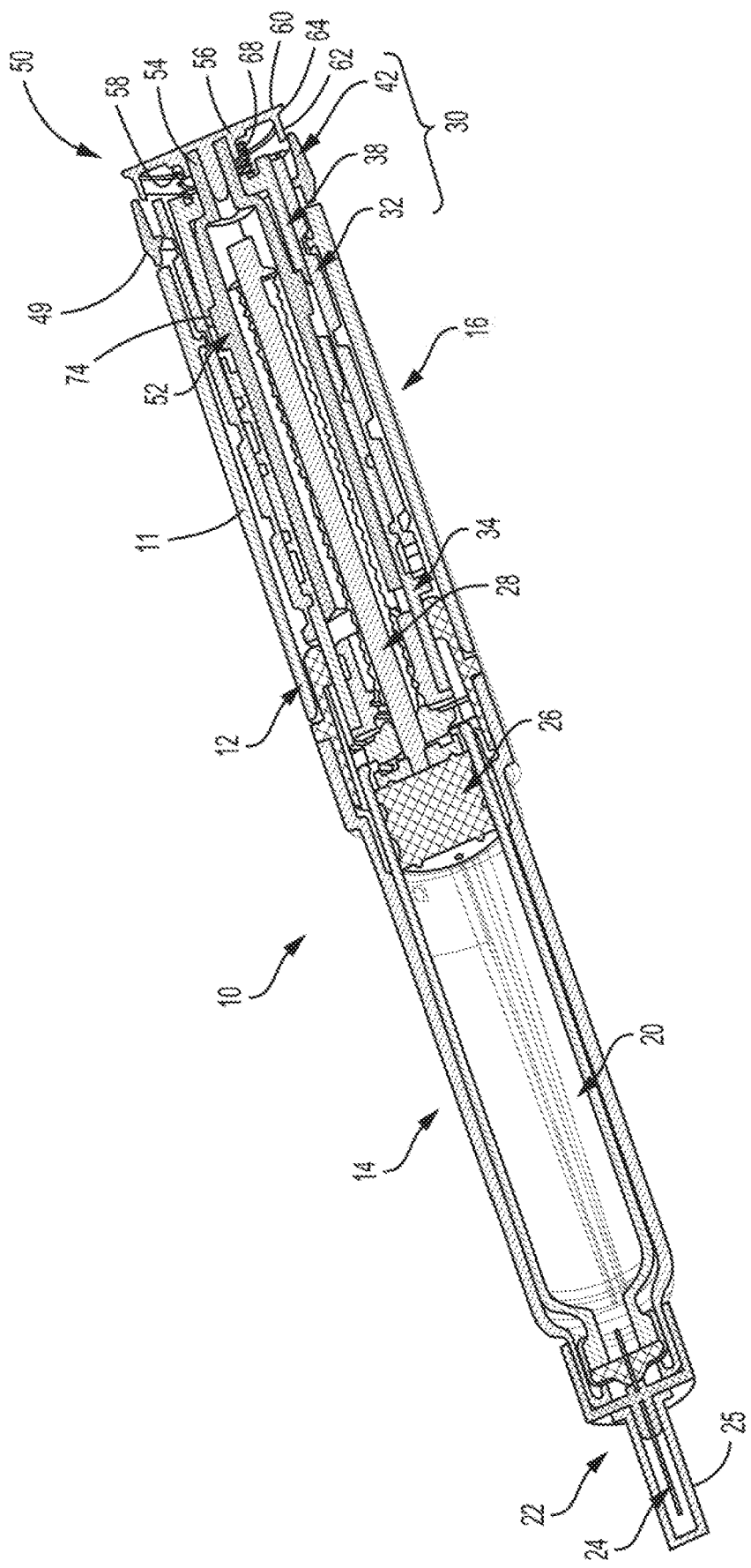
FIG. 2 is a cross-sectional perspective view of the exemplary medication delivery device of FIG. 1.

An exemplary medication delivery device 10 is illustrated in FIGS. 1-4 as a pen injector configured to inject a medication into a patient through a needle. Pen injector 10 includes a body 11 comprising an elongated, pen-shaped housing 12 including a distal portion 14 and a proximal portion 16. Distal portion 14 is received within a pen cap 18. Referring to FIG. 2, distal portion 14 contains the reservoir or cartridge 20 configured to hold the medicinal fluid of medication to be dispensed through its distal outlet end during a dispensing operation. The outlet end of distal portion 14 is equipped with a removable needle assembly 22 including an injection needle 24 enclosed by a removable cover 25. A piston 26 is positioned in reservoir 20. An injecting mechanism positioned in proximal portion 16 is operative to advance piston 26 toward the outlet of reservoir 20 during the dose dispensing operation to force the contained medicine through the needled end. The injecting mechanism includes a drive member 28, illustratively in the form of a screw, axially moveable relative to housing 12 to advance piston 26 through reservoir 20.

A dose setting member 30 is coupled to housing 12 for setting a dose amount to be dispensed by device 10. In the illustrated embodiment, dose setting member 30 is in the form of a screw element operative to spiral (i.e., simultaneously move axially and rotationally) relative to housing 12 during dose setting and dose dispensing. FIGS. 1 and 2 illustrate the dose setting member 30 fully screwed into housing 12 at its home or zero dose position. Dose setting member 30 is operative to screw out in a proximal direction from housing 12 until it reaches a fully extended position corresponding to a maximum dose deliverable by device 10 in a single injection.

Figures 3, 4:
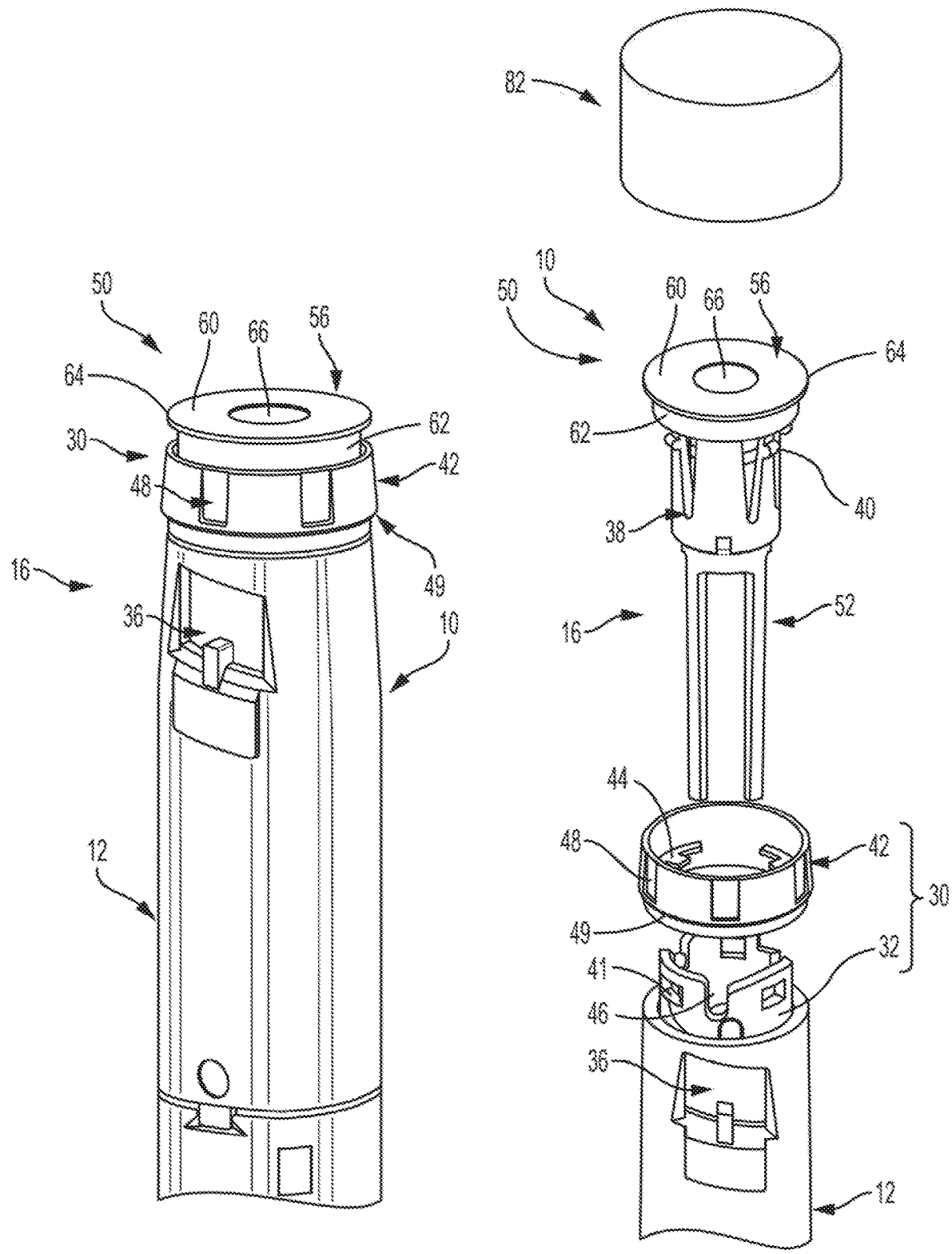
FIG. 3 is a perspective view of the proximal portion of the exemplary medication delivery device of FIG. 1.
FIG. 4 is a partially-exploded, perspective view of the proximal portion of the exemplary medication delivery device of FIG. 1, together with a dose detection system of the present disclosure.

Referring to FIGS. 2-4, dose setting member 30 includes a cylindrical dose dial member 32 having a helically threaded outer surface that engages a corresponding threaded inner surface of housing 12 to allow dose setting member 30 to spiral relative to housing 12. Dose dial member 32 further includes a helically threaded inner surface that engages a threaded outer surface of sleeve 34 (FIG. 2) of device 10. The outer surface of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotationally locked to dial member 32 by detents 40 received within openings 41 in dial member 32. Dose setting member 30 may further include a collar or skirt 42 positioned around the outer periphery of dial member 32 at its proximal end. Skirt 42 is axially and rotationally locked to dial member 32 by tabs 44 received in slots 46. Further embodiments described later shown examples of the device without a skirt.

Dose setting member 30 therefore may be considered to comprise any or all of dose dial member 32, flange 38, and skirt 42, as they are all rotationally and axially fixed together. Dose dial member 32 is directly involved in setting the dose and driving delivery of the medication. Flange 38 is attached to dose dial member 32 and, as described later, cooperates with a clutch to selectively couple dial member 32 with a dose button 56. Skirt 42 provides a surface external of body 11 to enable a user to rotate the dial member 32 for setting a dose.

Skirt 42 illustratively includes a plurality of surface features 48 and an annular ridge 49 formed on the outer surface of skirt 42. Surface features 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose button 56 and/or dose dial member 32 for dose setting. In the embodiment of FIG. 4, a user may grasp and rotate the radial exterior surface of one-piece dose button 56, which also includes a plurality of surface features, for dose setting.

Delivery device 10 includes an actuator 50 having a clutch 52 which is received within dial member 32. Clutch 52 includes an axially extending stem 54 at its proximal end. Actuator 50 further includes dose button 56 positioned proximally of skirt 42 of dose setting member 30. In an alternative embodiment, dose setting member 30 may include a one-piece dose button without the skirt, such as, for example, shown in FIGS. 14, 18, 19, and 22. Dose button 56 includes a mounting collar 58 (FIG. 2) centrally located on the distal surface of dose button 56. Collar 58 is attached to stem 54 of clutch 52, such as with an interference fit or an ultrasonic weld, so as to axially and rotatably fix together dose button 56 and clutch 52.

Figure 22:
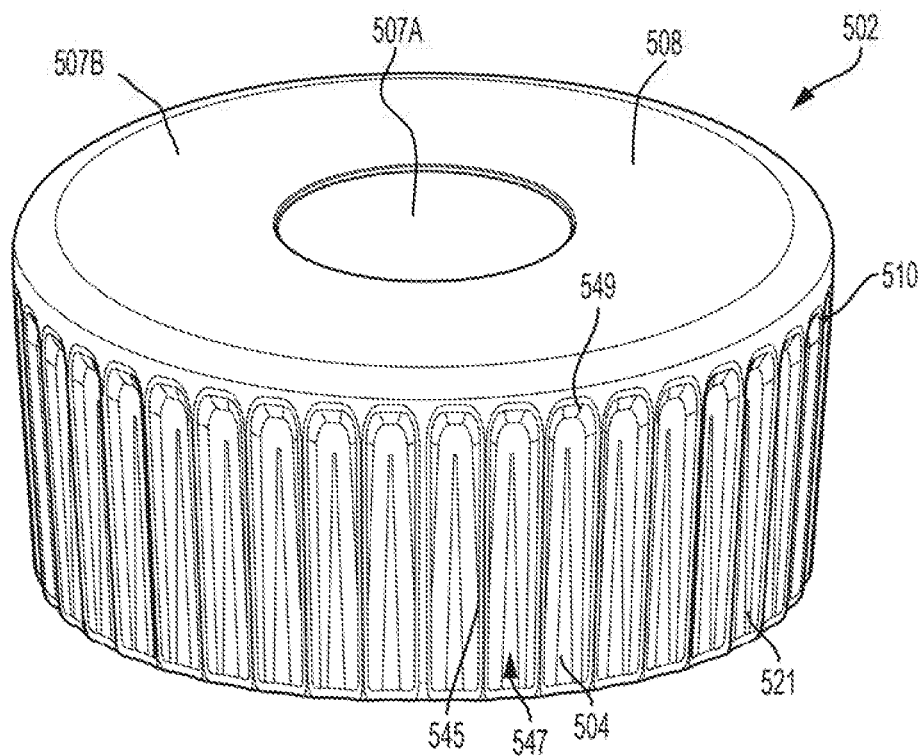
FIG. 22 is a perspective view of the dose button in FIG. 20.

Dose button 56 includes a disk-shaped proximal end surface or face 60 and an annular wall portion 62 extending distally and spaced radially inwardly of the outer peripheral edge of face 60 to form an annular lip 64 there between. Proximal face 60 of dose button 56 serves as a push surface against which a force can be applied manually, i.e., directly by the user to push actuator 50 in a distal direction. Dose button 56 illustratively includes a recessed portion 66 centrally located on proximal face 60, although proximal face 60 alternatively may be a flat surface. Similarly, the alternative one-piece dose button, such as shown in FIG. 22, may include a recessed portion 66 centrally located on proximal face 60 or alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation.

Delivery device 10 is operable in both a dose setting mode and a dose dispensing mode. In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" may equal one-half or one unit of medication. The set dose amount is visible to the user via the dial indicator markings shown through dosage window 36. Actuator 50, including dose button 56 and clutch 52, move axially and rotationally with dose setting member 30 during the dialing in the dose setting mode.

Dose dial member 32, flange 38 and skirt 42 are all fixed rotationally to one another, and rotate and extend proximally of the medication delivery device 10 during dose setting, due to the threaded connection of dose dial member 32 with housing 12. During this dose setting motion, dose button 56 is rotationally fixed relative to skirt 42 by complementary splines 74 of flange 38 and clutch 52 (FIG. 2), which are urged together by bias member 68. In the course of dose setting, skirt 42 and dose button 56 move relative to housing 12 in a spiral manner from a "start" position to an "end" position. This rotation relative to the housing is in proportion to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56. The axial force is applied by the user directly to dose button 56. This causes axial movement of actuator 50 in the distal direction relative to housing 12.

The axial shifting motion of actuator 50 compresses biasing member 68 and reduces or closes the gap between dose button 56 and tubular flange 38. This relative axial movement separates the complementary splines 74 on clutch 52 and flange 38, and thereby disengages actuator 50, e.g., dose button 56, from being rotationally fixed to dose setting member 30. In particular, dose setting member 30 is rotationally uncoupled from actuator 50 to allow back-driving rotation of dose setting member 30 relative to actuator 50 and housing 12. The dose dispensing mode of operation may also be initiated by activating a separate switch or trigger mechanism.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3.

The start and end angular positions of dose dial member 32, and therefore of the rotationally fixed flange 38 and skirt 42, relative to dose button 56 provide an "absolute" change in angular positions during dose delivery. Determining whether the relative rotation was in excess of 360° is determined in a number of ways. By way of example, total rotation may be determined by also taking into account the incremental movements of the dose setting member 30 which may be measured in any number of ways by a sensing system.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein. Another example of the delivery device is an auto-injector device that may be found in U.S. Pat. No. 8,734,394, entitled "Automatic Injection Device With Delay Mechanism Including Dual Functioning Biasing Member," which is hereby incorporated by reference in its entirety, where such device being modified with one or more various sensor systems described herein to determine an amount of medication delivered from the medication delivery device based on the sensing of relative rotation within the medication delivery device.

The dose detection systems described herein use a sensing component and a sensed component attached to members of the medication delivery device. The term "attached" encompasses any manner of securing the position of a component to another component or to a member of the medication delivery device such that they are operable as described herein. For example, a sensing component may be attached to a member of the medication delivery device by being directly positioned on, received within, integral with, or otherwise connected to, the member. Connections may include, for example, connections formed by frictional engagement, splines, a snap or press fit, sonic welding or adhesive.

The term "directly attached" is used to describe an attachment in which two components, or a component and a member, are physically secured together with no intermediate member, other than attachment components. An attachment component may comprise a fastener, adapter or other part of a fastening system, such as a compressible membrane interposed between the two components to facilitate the attachment. A "direct attachment" is distinguished from a connection where the components/members are coupled by one or more intermediate functional members, such as the way dial member 32 is coupled in FIG. 2 to the dose button 56 by a clutch 52.

The term "fixed" is used to denote that an indicated movement either can or cannot occur. For example, a first member is "fixed rotationally" with a second member if the two members are required to move together in rotation. In one aspect, a member may be "fixed" relative to another member functionally, rather than structurally. For example, a member may be pressed against another member such that the frictional engagement between the two members fixes them together rotationally, while the two members may not be fixed together absent the pressing of the first member.

Various sensor systems are contemplated herein. In general, the sensor systems comprise a sensing component and a sensed component. The term "sensing component" refers to any component which is able to detect the relative position of the sensed component. The sensing component includes a sensing element, or "sensor", along with associated electrical components to operate the sensing element. The "sensed component" is any component for which the sensing component is able to detect the position and/or movement of the sensed component relative to the sensing component. For the dose delivery detection system, the sensed component rotates relative to the sensing component, which is able to detect the angular position and/or the rotational movement of the sensed component. For the dose type detection system, the sensing component detects the relative angular position of the sensed component. The sensing component may comprise one or more sensing elements, and the sensed component may comprise one or more sensed elements. The sensor system is able to detect the position or movement of the sensed component(s) and to provide outputs representative of the position(s) or movement(s) of the sensed component(s).

A sensor system typically detects a characteristic of a sensed parameter which varies in relationship to the position of the one or more sensed elements within a sensed area. The sensed elements extend into or otherwise influence the sensed area in a manner that directly or indirectly affects the characteristic of the sensed parameter. The relative positions of the sensor and the sensed element affect the characteristics of the sensed parameter, allowing a microcontroller unit (MCU) of the sensor system to determine different rotational positions of the sensed element.

Suitable sensor systems may include the combination of an active component and a passive component. With the sensing component operating as the active component, it is not necessary to have both components connected with other system elements such as a power supply or MCU.

Any of a variety of sensing technologies may be incorporated by which the relative positions of two members can be detected. Such technologies may include, for example, technologies based on tactile, optical, inductive or electrical measurements. Such technologies may include the measurement of a sensed parameter associated with a field, such as a magnetic field. In one form, a magnetic sensor senses the change in a sensed magnetic field as a magnetic component is moved relative to the sensor. In another embodiment, a sensor system may sense characteristics of and/or changes to a magnetic field as an object is positioned within and/or moved through the magnetic field. The alterations of the field change the characteristic of the sensed parameter in relation to the position of the sensed element in the sensed area. In such embodiments the sensed parameter may be a capacitance, conductance, resistance, impedance, voltage, inductance, etc. For example, a magneto-resistive type sensor detects the distortion of an applied magnetic field which results in a characteristic change in the resistance of an element of the sensor. As another example, Hall effect sensors detect changes in voltage resulting from distortions of an applied magnetic field.

In one aspect, the sensor system detects relative positions or movements of the sensed elements, and therefore of the associated members of the medication delivery device. The sensor system produces outputs representative of the position(s) or the amount of movement of the sensed component. For example, the sensor system may be operable to generate outputs by which the rotation of the dose setting member during dose delivery can be determined. MCU is operably connected to each sensor to receive the outputs. In one aspect, MCU is configured to determine from the outputs the amount of dose delivered by operation of the medication delivery device.

The dose delivery detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable. The sensor system is operable to determine the total angular displacement of a dose setting member during dose delivery. Thus, if the angular displacement is 90°, then 5 units of dose have been delivered.

One approach for detecting the angular displacement is to count increments of dose amounts as the injection proceeds. For example, a sensor system may use a repeating pattern of sensed elements, such that each repetition is an indication of a predetermined degree of angular rotation. Conveniently, the pattern may be established such that each repetition corresponds to the minimum increment of dose that can be set with the medication delivery device.

An alternative approach is to detect the start and stop positions of the relatively moving member, and to determine the amount of delivered dose as the difference between those positions. In this approach, it may be a part of the determination that the sensor system detects the number of full rotations of the dose setting member. Various methods for this are well within the ordinary skill in the art, and may include "counting" the number of increments to assess the number of full rotations.

The sensor system components may be permanently or removably attached to the medication delivery device. In an illustrative embodiment, as least some of the dose detection system components are provided in the form of a module that is removably attached to the medication delivery device. This has the advantage of making these sensor components available for use on more than one pen injector.

In some embodiments, a sensing component is mounted to the actuator and a sensed component is attached to the dose setting member. The sensed component may also comprise the dose setting member or any portion thereof. The sensor system detects during dose delivery the relative rotation of the sensed component, and therefore of the dose setting member, from which is determined the amount of a dose delivered by the medication delivery device. In an illustrative embodiment, a rotation sensor is attached, and rotationally fixed, to the actuator. The actuator does not rotate relative to the body of the medication delivery device during dose delivery. In this embodiment, a sensed component is attached, and rotationally fixed, to the dose setting member, which rotates relative to the actuator and the device body during dose delivery. The sensed component may also comprise the dose setting member or any portion thereof. In an illustrative embodiment, the rotation sensor is not attached directly to the relatively rotating dose setting member during dose delivery.

Figure 5:
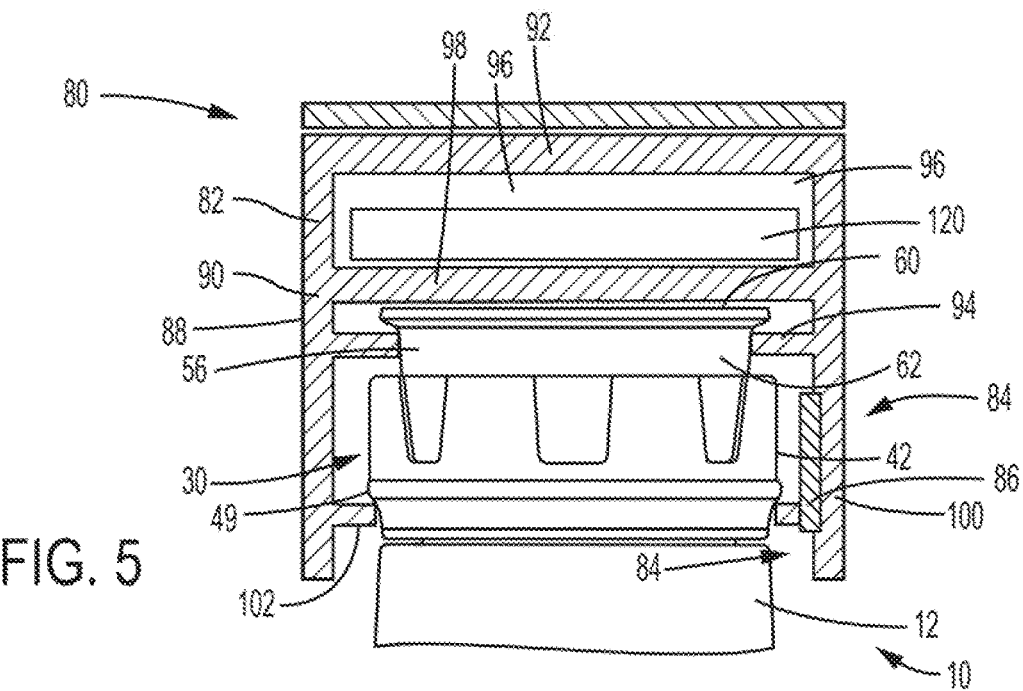
FIG. 5 is a side, diagrammatic view, partially in cross section, of a dose detection system module according to another exemplary embodiment attached to the proximal portion of a medication delivery device.

Referring to FIG. 5, there is shown in diagrammatic form a dose delivery detection system 80 including one example of a module 82 useful in combination with a medication delivery device, such as device 10. Module 82 carries a sensor system, shown generally at 84, including a rotation sensor 86 and other associated components such as a processor, memory, battery, etc. Module 82 is provided as a separate component which may be removably attached to the actuator.

Figure 15:
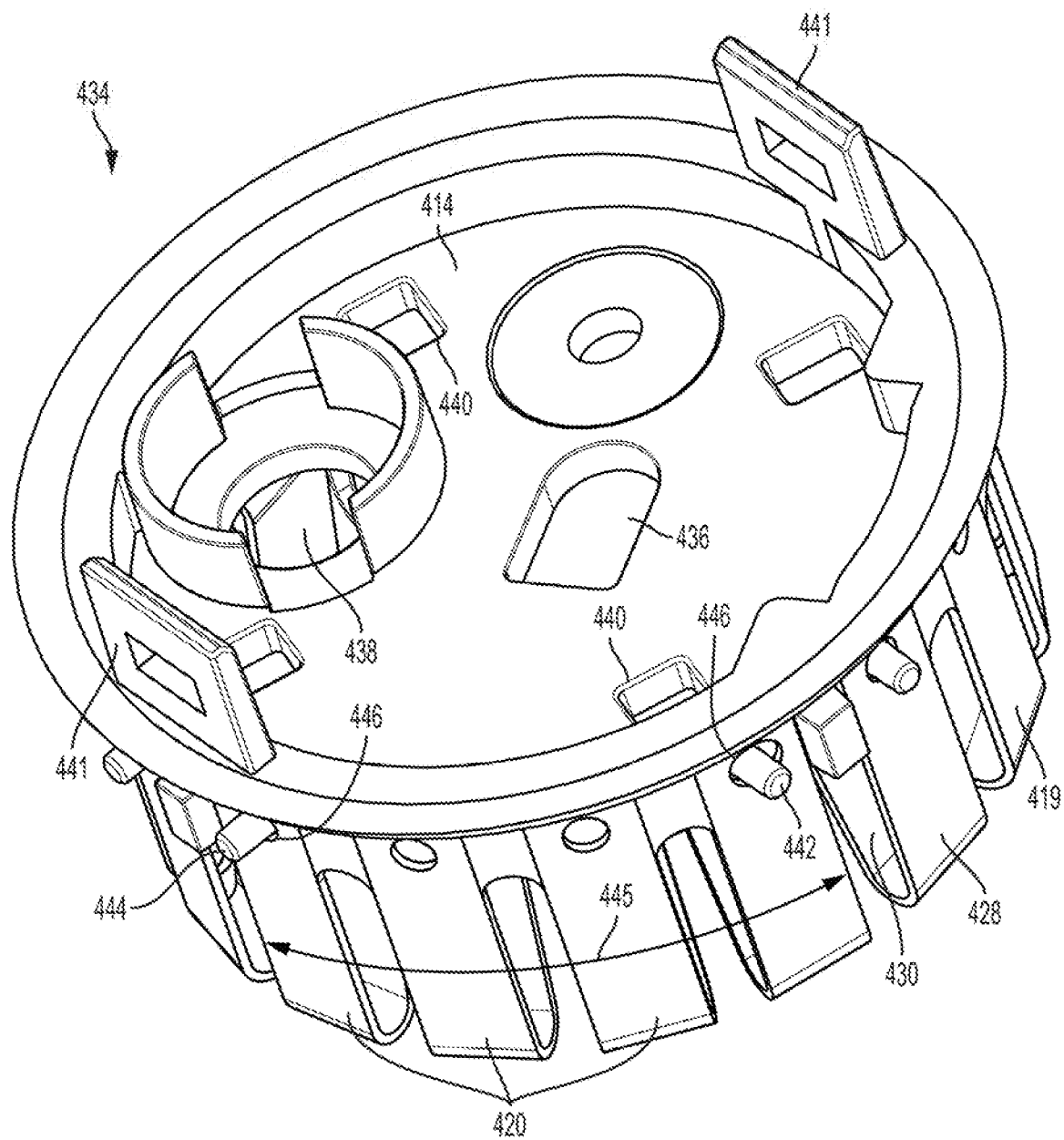
FIG. 15 is a perspective view of a subassembly of a module housing of the dose detection system module in FIG. 13.
Figure 23:
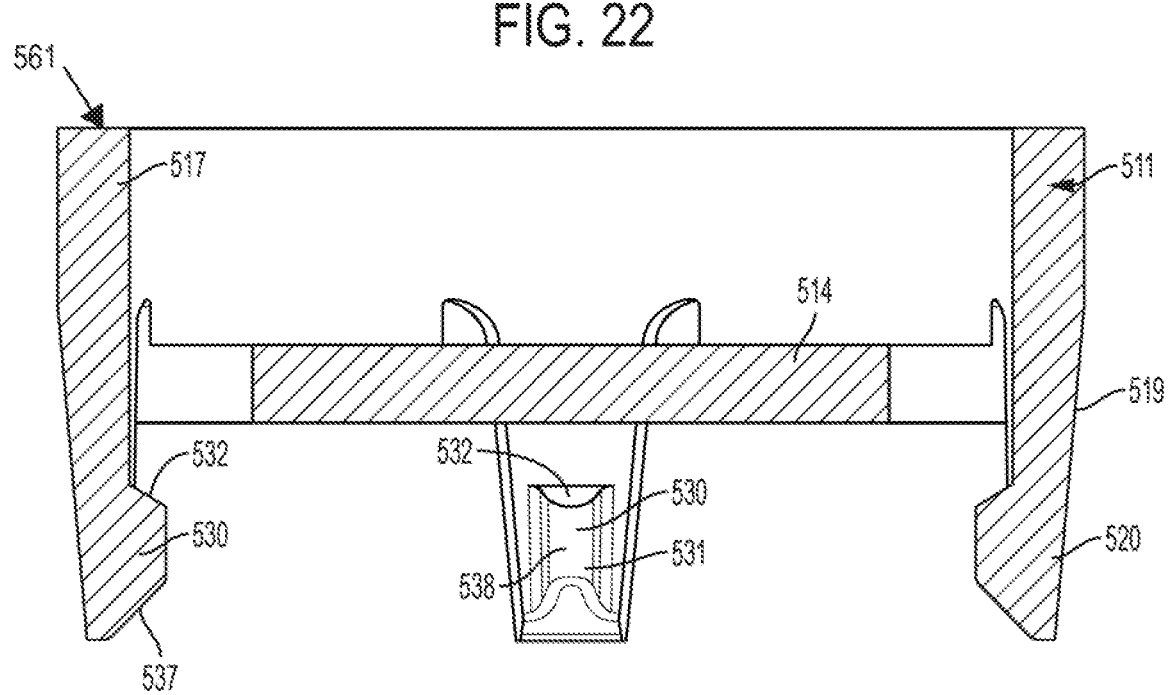
FIG. 23 is a cross-sectional view of the subassembly of the module housing in FIG. 20.
Figure 37:
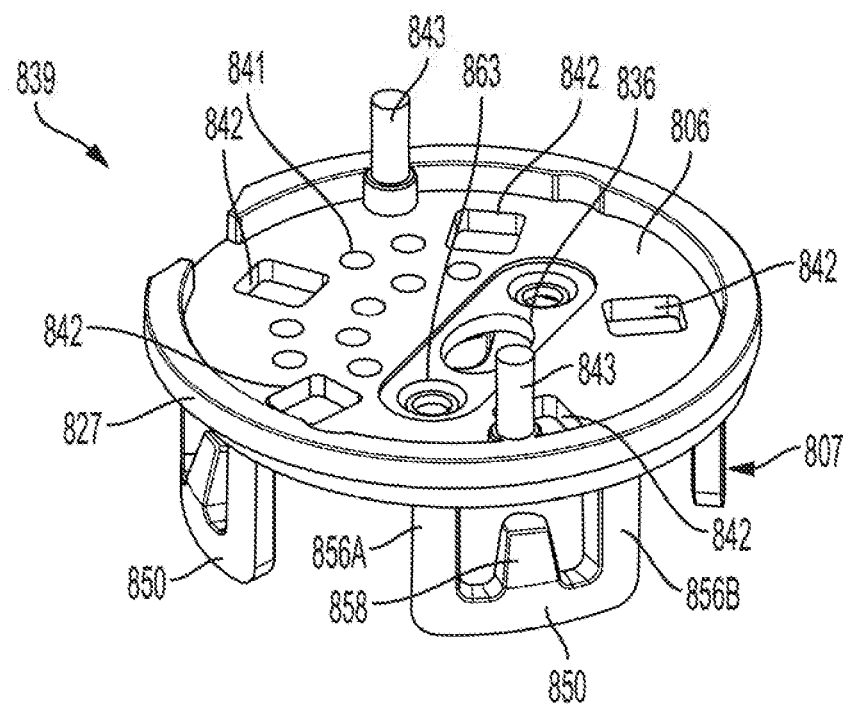
FIG. 37 is a perspective proximal view of a unit component of the module of FIG. 35.

Dose detection module 82 includes a body 88 attached to dose button 56. Body 88 illustratively includes a cylindrical side wall 90 and a top wall 92, spanning over and sealing side wall 90. By way of example, in FIG. 5 upper side wall 90 is diagrammatically shown having inwardly-extending tabs 94 attaching module 82 to dose button 56. Dose detection module 82 may alternatively be attached to dose button 56 via any suitable fastening means, such as a snap or press fit, threaded interface, etc., provided that in one aspect module 82 may be removed from a first medication delivery device and thereafter attached to a second medication delivery device. The attachment may be at any location on dose button 56, provided that dose button 56 is able to move any required amount axially relative to dose setting member 30, as discussed herein. Examples of alternative attachment elements for module 82 are shown in FIGS. 15, 23 and 37 described later.

During dose delivery, dose setting member 30 is free to rotate relative to dose button 56 and module 82. In the illustrative embodiment, module 82 is rotationally fixed with dose button 56 and does not rotate during dose delivery. This may be provided structurally, such as with tabs 94 of FIG. 5, or by having mutually-facing splines or other surface features on the module body 88 and dose button 56 engage upon axial movement of module 82 relative to dose button 56. In another embodiment, the distal pressing of the module provides a sufficient frictional engagement between module 82 and dose button 56 as to functionally cause the module 82 and dose button 56 to remain rotationally fixed together during dose delivery.

Top wall 92 is spaced apart from face 60 of dose button 56 and thereby provides a cavity 96 in which some or all of the rotation sensor and other components may be contained. Cavity 96 may be open at the bottom, or may be enclosed, such as by a bottom wall 98. Bottom wall 98 may be positioned in order to bear directly against face 60 of dose button 56. Alternatively, bottom wall 98 if present may be spaced apart from dose button 56 and other contacts between module 82 and dose button 56 may be used such that an axial force applied to module 82 is transferred to dose button 56. In another embodiment, module 82 may be rotationally fixed to the one-piece dose button configuration, such as shown in FIG. 22.

In an alternate embodiment, module 82 during dose setting is instead attached to dose setting member 30. For example, side wall 90 may include a lower wall portion 100 having inward projections 102 that engage with skirt 42 in a position underneath ridge 49. In this approach, tabs 94 may be eliminated and module 82 effectively engages the proximal face 60 of dose button 56 and the distal side of annular ridge 49. In this configuration, lower wall portion 100 may be provided with surface features which engage with the surface features of skirt 42 to rotationally fix module 82 with skirt 42. Rotational forces applied to housing 82 during dose setting are thereby transferred to skirt 42 by virtue of the coupling of lower wall portion 100 with skirt 42.

Module 82 is disengaged rotationally from skirt 42 in order to proceed with dose delivery. The coupling of lower wall portion 100 with skirt 42 is configured to disconnect upon distal axial movement of module 82 relative to skirt 42, thereby allowing skirt 42 to rotate relative to module 82 during dose delivery.

In a similar fashion, module 82 may be coupled with both dose button 56 and skirt 42 during dose setting. This has the advantage of providing additional coupling surfaces during rotation of the module in dose setting. The coupling of the module 82 to the skirt 42 is then released prior to dose injection, such as by the axial movement of module 82 relative to skirt 42 as dose delivery is being initiated, thereby allowing dose setting member 30 to rotate relative to module 82 during dose delivery.

In certain embodiments, rotation sensor 86 is coupled to side wall 90 for detecting a sensed component. Lower wall portion 100 also serves to reduce the likelihood that a user's hand inadvertently applies drag to dose setting member 30 as it rotates relative to module 82 and housing 12 during dose delivery. Further, since dose button 56 is rotationally fixed to dose setting member 30 during dose setting, the side wall 90, including lower wall portion 100, provide a single, continuous surface which may be readily grasped and manipulated by the user during dose setting.

When the injection process is initiated by pressing down on the dose detection module 82, dose button 56 and dose setting member 30 are rotationally fixed together. Movement of module 82, and therefore dose button 56, a short distance, for example less than 2 mm, releases the rotational engagement and the dose setting member 30 rotates relative to module 82 as the dose is delivered. Whether by use of a finger pad or other triggering mechanism, the dose detection system is activated before the dose button 56 has moved a sufficient distance to disengage the rotational locking of the dose button 56 and the dose setting member 30.

Illustratively, the dose delivery detection system includes an electronics assembly suitable for operation of the sensor system as described herein. Electronics assembly is operably connected to the sensor system to receive outputs from one or more rotational sensors. Electronics assembly may include conventional components such as a processor, power supply, memory, microcontrollers, etc. contained for example in cavity 96 defined by module body 88. Alternatively, at least some components may be provided separately, such as by means of an external device such as a computer, smart phone or other device. Means are then provided to operably connect the external controller components with the sensor system at appropriate times, such as by a wired or wireless connection.

Figure 46:
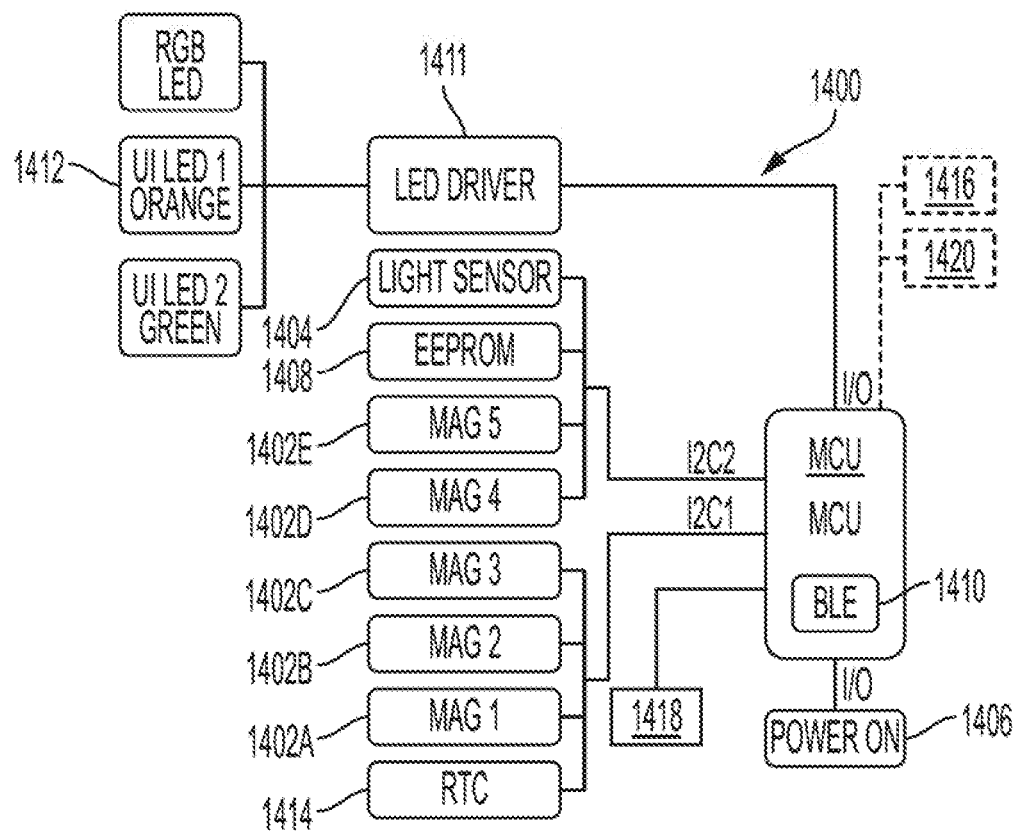
FIG. 46 depicts a block diagram of the controller and its components.

An exemplary electronics assembly 120 comprises a flexible printed circuit board (FPCB) having a plurality of electronic components. The electronics assembly comprises a sensor system including one or more rotation sensors 86 operatively communicating with a processor for receiving signals from the sensor representative of the sensed relative rotation. The electronics assembly further includes the MCU comprising at least one processing core and internal memory. One example of an electronics assembly schematic is shown in FIG. 46. The system includes a battery, illustratively a coin cell battery, for powering the components. The MCU includes control logic operative to perform the operations described herein, including detecting a dose delivered by medication delivery device 10 based on a detected rotation of the dose setting member relative to the actuator. In one embodiment, the detected rotation is between the skirt 42 and the dose button 56 of a pen injector.

The MCU is operative to store the detected dose in local memory (e.g., internal flash memory or on-board EEPROM). The MCU is further operative to wirelessly transmit and/or receive a signal representative of the detected dose to a paired remote electronic device, such as a user's smartphone, over a Bluetooth low energy (BLE) or other suitable short or long range wireless communication protocol. Illustratively, the BLE control logic and MCU are integrated on a same circuit. Further description of the electronics arrangement is described further below.

Much of the sensing electronics is contained in the cavity 96. However, the rotation sensor may be positioned in a variety of locations in order to sense the relative movement of the sensed component. For example, the rotation sensor may be located within cavity 96, within body 88 but outside of the cavity 96, or in other locations of the body, such as on lower wall portion 100. The only requirement is that the rotation sensor be positioned to effectively detect the rotational movement of the sensed component during dose delivery. In some embodiments, the rotation sensor is integral to the device 10.

One or more sensed elements are attached to the dose setting member 30. In one aspect, the sensed elements are directly attached to skirt 42 of the dose setting member. Alternatively, sensed elements may be attached to any one or more of the dose setting components, including the dial member, flange and/or skirt. The only requirement is that the sensed element(s) be positioned to be sensed by the rotation sensor during relative rotational movement during dose delivery. In other embodiments, the sensed component comprises the dose setting member 30 or any portion thereof.

Further illustrative embodiments of a dose delivery detection system 80 are provided in FIGS. 6-13. The embodiments are shown in somewhat diagrammatic fashion, as common details have already been provided with respect to FIGS. 1-5. In general, each embodiment includes similar components of the dose detection module 82, including a body 88 having a cylindrical upper wall 90 and a top wall 92.

Figure 35:
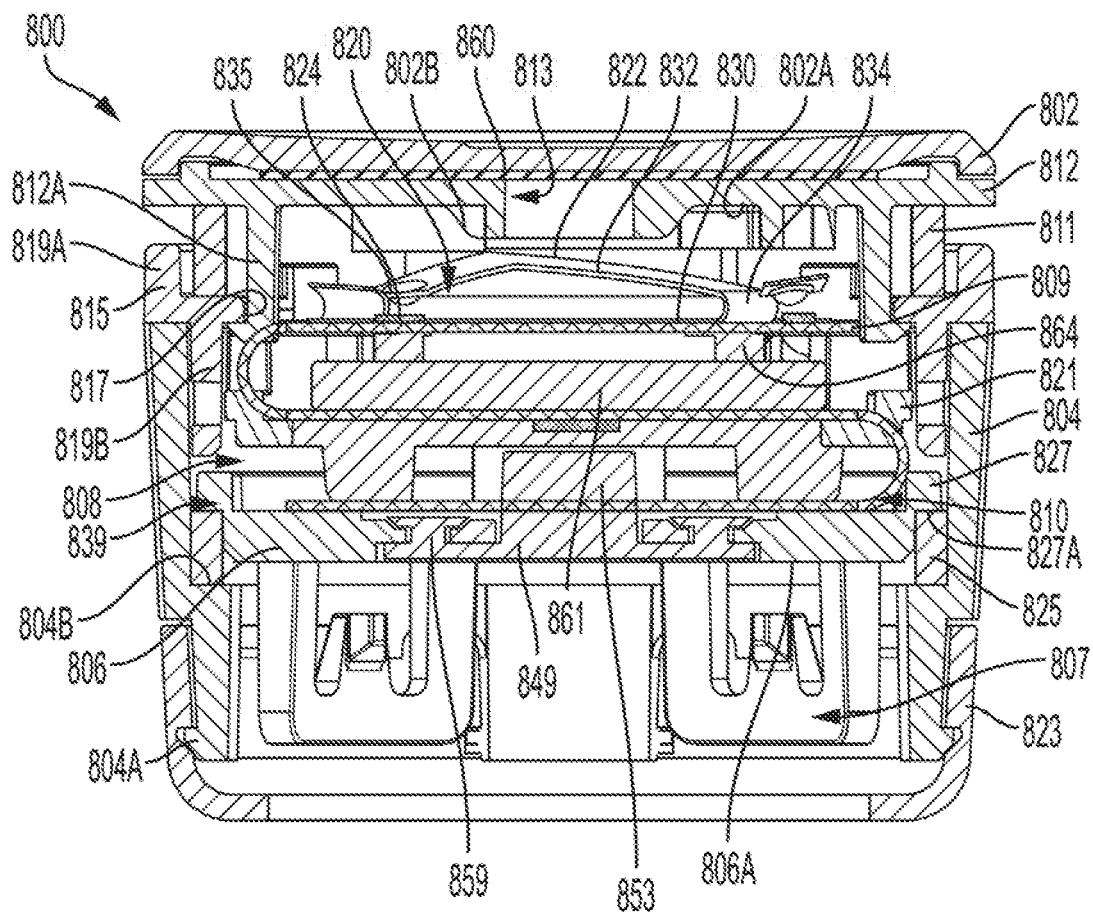
FIG. 35 is a cross-sectional view of another embodiment of a module of a dose delivery detection system attached to the proximal portion of the medication delivery device.

Each embodiment also includes a lower wall 100, although it will be appreciated that variations on these components, including the absence of lower wall 100, are within the scope of the disclosure. Other parts common to the earlier descriptions herein include an electronics assembly 120 contained within cavity 96 of module body 88, dose button 56, dose setting member 32 and device housing 12. Further, in each embodiment the dose detection module 82 is diagrammatically shown as being attached to the annular side wall 62 of dose button 56, although alternative forms and locations of attachment may be used. For example, dose detection module 82 may be attached to dose button 56 and releasably attached to skirt 42 in some embodiments. Also, dose detection module 82 may be attached to one-piece dose button, such as shown in FIGS. 22 and 35.

Each example also demonstrates the use of a particular type of sensor system. However, in some embodiments the dose detection system includes multiple sensing systems using the same or different sensing technologies. This provides redundancy in the event of failure of one of the sensing systems. It also provides the ability to use a second sensing system to periodically verify that the first sensing system is performing appropriately.

Figure 6:
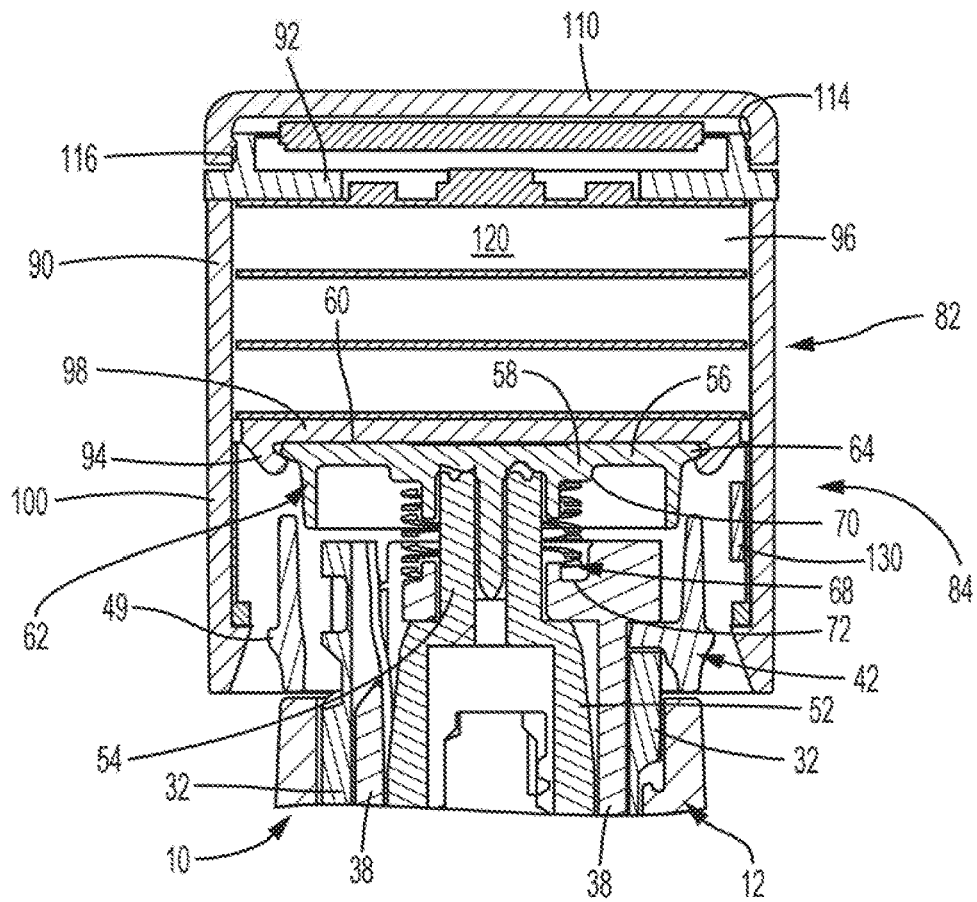
FIG. 6 is a cross-sectional view of a module of a dose detection system according to an exemplary embodiment attached to the proximal portion of a medication delivery device.

In certain embodiments, as shown in FIG. 6, attached to top wall 92 of module 82 is a finger pad 110. Finger pad 110 is coupled to top wall 92, which is in turn attached to upper side wall 90. Finger pad 110 includes a ridge 114 which extends radially inward and is received within circumferential groove 116 of wall component 92. Groove 116 allows a slight axial movement between finger pad 110 and wall component 92. Springs (not shown) normally urge finger pad 110 upwardly away from wall component 92. Finger pad 110 may be rotationally fixed to wall component 92. Axial movement of finger pad 110 in the distal direction toward module body 88 as the injection process is initiated may be used to trigger selected events. One use of finger pad 110 may be the activation of the medication delivery device electronics upon initial pressing and axial movement of the finger pad 110 relative to the module body 88 when dose injection is initiated. For example, this initial axial movement may be used to "wake up" the device, and particularly the components associated with the dose detection system. In one example, module 82 includes a display for indication of information to a user. Such a display may be integrated with finger pad 110. MCU may include a display drive software module and control logic operative to receive and processed sensed data and to display information on said display, such as, for example, dose setting, dosed dispensed, status of injection, completion of injection, date and/or time, or time to next injection.

In the absence of a finger pad, the system electronics may be activated in various other ways. For example, the initial axial movement of module 82 at the start of dose delivery may be directly detected, such as by the closing of contacts or the physical engagement of a switch. It is also known to activate a medication delivery device based on various other actions, e.g., removal of the pen cap, detection of pen movement using an accelerometer, or the setting of the dose. In many approaches, the dose detection system is activated prior to the start of dose delivery.

Figure 7:
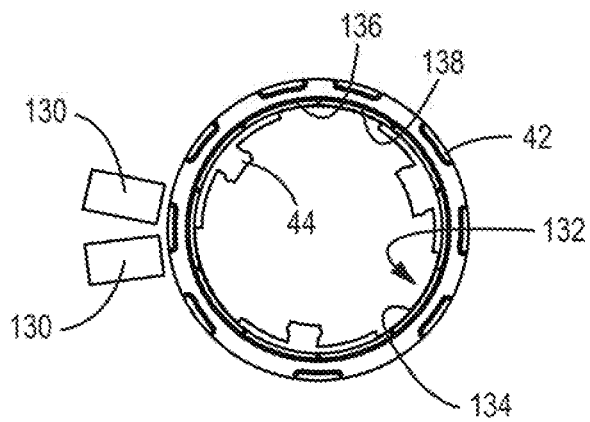
FIG. 7 is a top, diagrammatic view showing rotation sensors positioned to detect magnetic sensed elements attached to a dose setting member in accordance with an exemplary embodiment.
Figure 8:
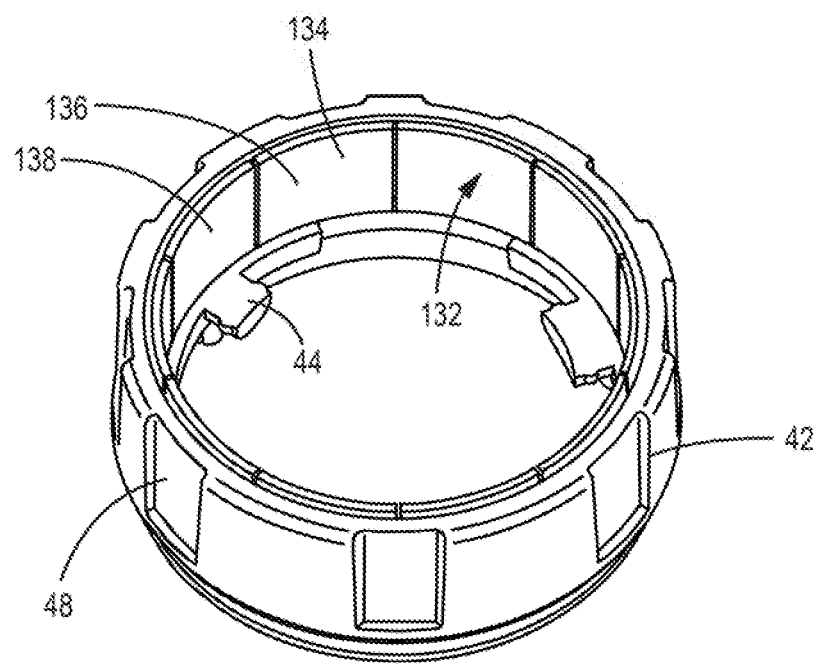
FIG. 8 is a perspective view of the dose setting member of FIG. 7 including the magnetic sensed elements.

Referring to FIGS. 6-8, dose detection module 82 operates using a magnetic sensing system 84. Two magnetic sensors 130 are positioned on lower wall portion 100 (illustratively the inside surface of lower wall portion 100) opposite skirt 42 of dose setting member 30. As for all embodiments, the number and location of the rotation sensor(s) and the sensed element(s) may be varied. For example, the embodiment of FIGS. 6-8 may instead include any number of magnetic sensors 130 evenly or unevenly spaced around skirt 42. The sensed component 132 (FIGS. 7 and 8) comprises a magnetic strip 134 secured to skirt 42, illustratively on the interior of skirt 42. In the illustrative embodiment, the strip comprises 5 pairs of north-south magnetic components, e.g., 136 and 138, each magnetic portion therefore extending for 36°. The magnetic sensors 130 are positioned at a separation of 18° (FIG. 7), and read the digital positions of magnetic strip 132, and therefore of skirt 42, in a 2-bit grey code fashion. For example, as the sensor detects the passage of an N-S magnetic pair, it is detected that skirt 42 has rotated 36°, corresponding to 2 units, for example, of dose being added (or subtracted).

Figure 9:
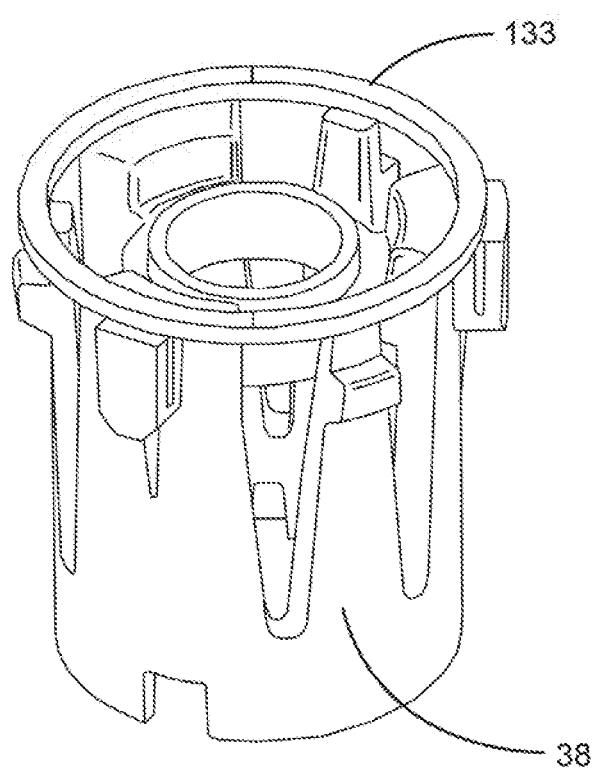
FIG. 9 is a perspective view of an alternate embodiment of a magnetic dose detection system.
Figure 10A:
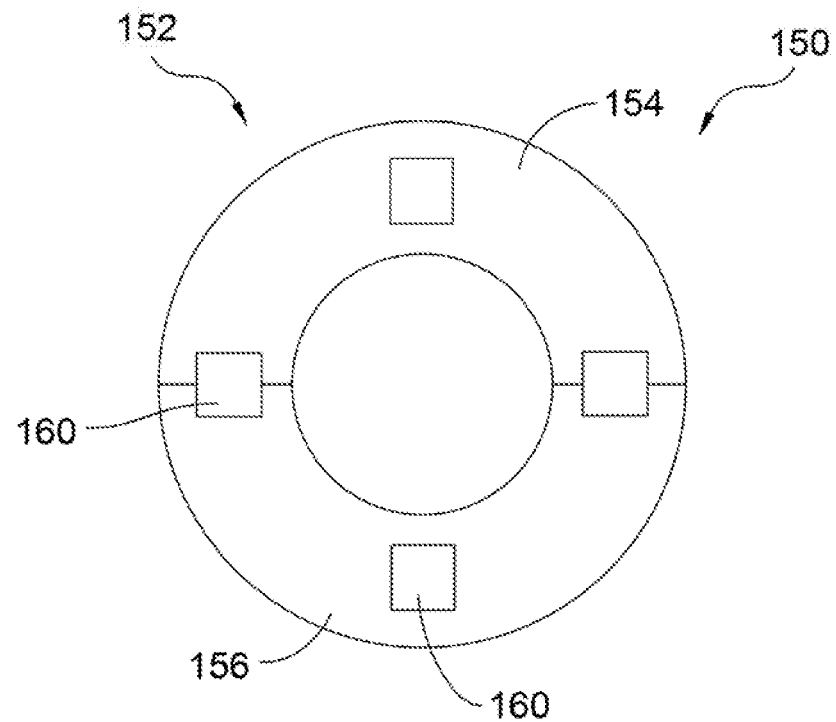
FIGS. 10A-B and 11A-B show yet other exemplary embodiments of dose detection systems utilizing magnetic sensing.
Figure 10B:
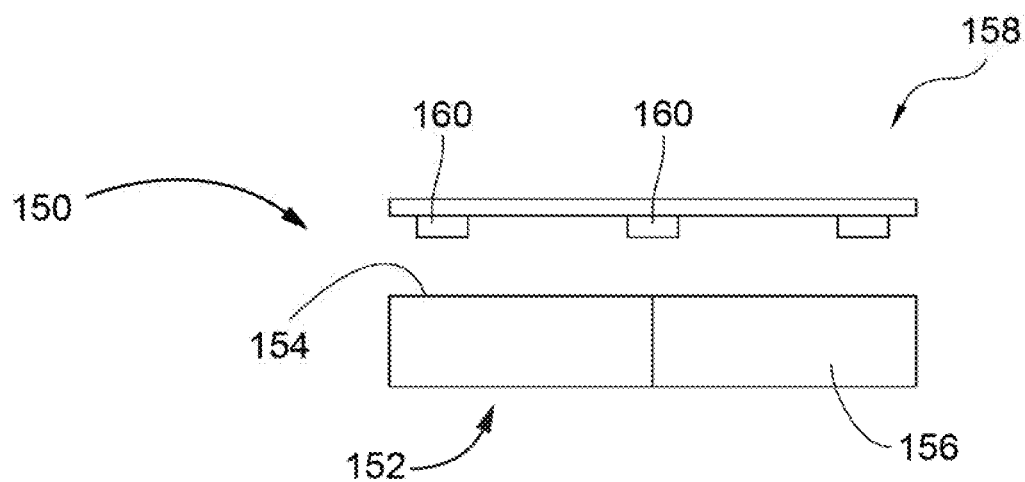

Other magnetic patterns, including different numbers or locations of magnetic elements, may also be used. Further, in an alternative embodiment, a sensed component 133 is attached to or integral with flange 38 of dose setting member 30, as illustrated in FIG. 9.

As previously described, the sensing system 84 is configured to detect the amount of rotation of the sensed element relative to the magnetic sensors 130. This amount of rotation is directly correlated to the amount of dose delivered by the device. The relative rotation is determined by detecting the movements of the skirt 42 during dose delivery, for example, by identifying the difference between the start and stop positions of skirt 42, or by "counting" the number of incremental movements of skirt 42 during the delivery of medication.

Figure 31:
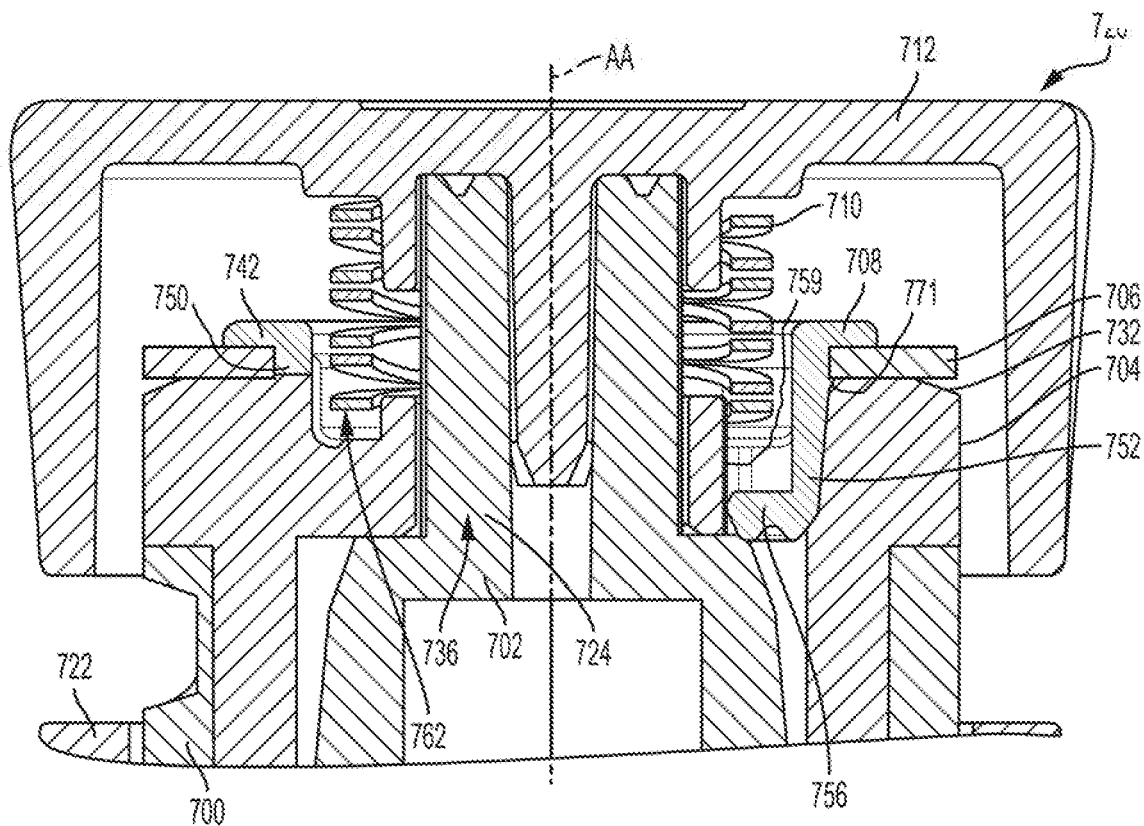
FIG. 31 is a side, diagrammatic view, partially in cross section, of a proximal portion of the subassembly in FIG. 30 assembled.
Figure 32:
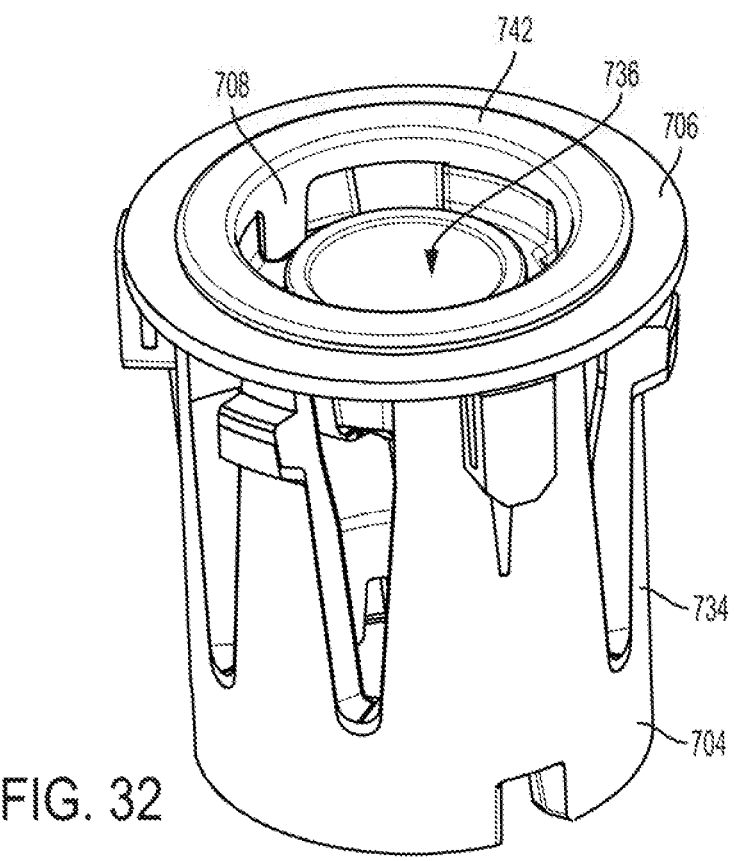
FIG. 32 is a perspective proximal view of a flange, a carrier, and a rotation sensed element assembled to one another.
Figure 33:
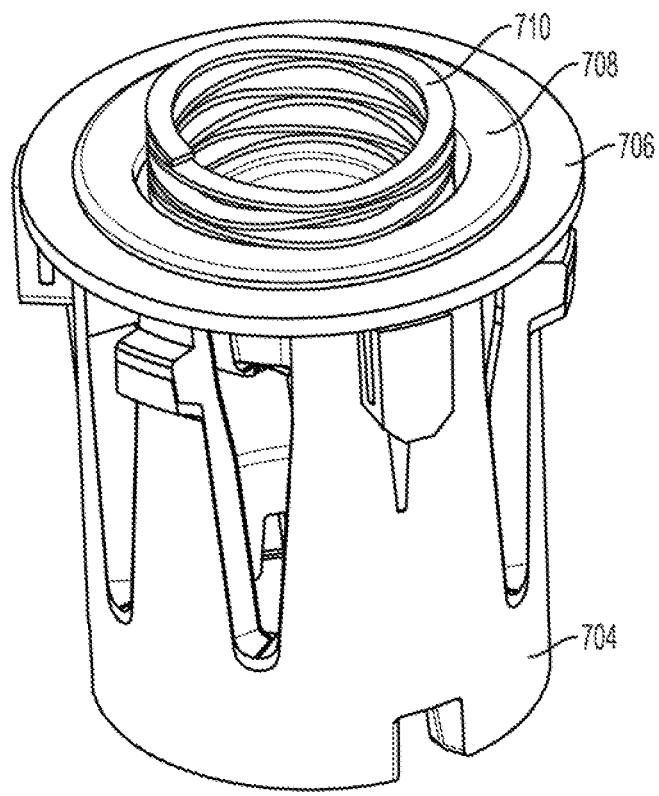
FIG. 33 is a perspective proximal view of the flange, the carrier, the rotation sensed element, and a spring assembled.

Referring to FIGS. 10A, 10B, 11A, and 11B, there is shown an exemplary magnetic sensor system 150 including as the sensed element an annular, ring-shaped, bipolar magnet 152 having a north pole 154 and a south pole 156. Magnets described herein may also be referred to as diametrically magnetized ring. Magnet 152 is attached to flange 38 and therefore rotates with the flange during dose delivery. In one example, the magnet 152 is attached to the flange 38 with an attachment carrier as shown in FIGS. 31-33. Magnet 152 may alternately be attached to dose dial 32 or other members rotationally fixed with the dose setting member. Magnet 152 may configured from a variety materials, such as, rare-earth magnets, for example, neodymium, and others a described later.

Figure 11A:
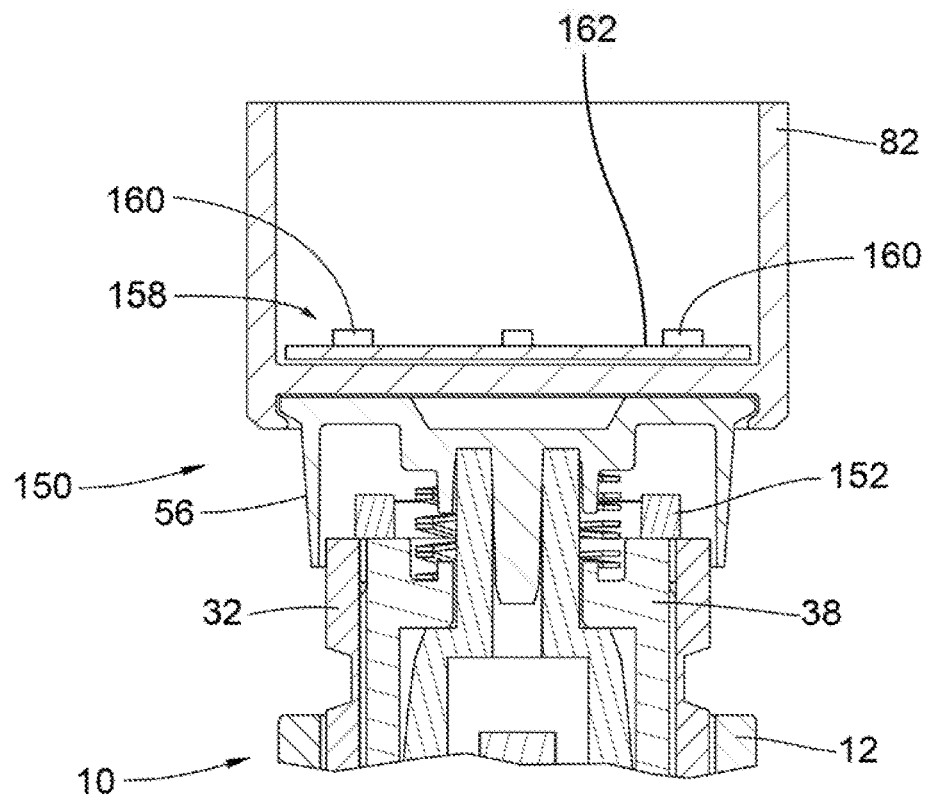

Sensor system 150 further includes a measurement sensor 158 including one or more sensing elements 160 operatively connected with sensor electronics (not shown) contained within module 82. The sensing elements 160 of sensor 158 are shown in FIG. 11A attached to printed circuit board 162 which is turn attached module 82, which is rotationally fixed to dose button 56. Consequently, magnet 152 rotates relative to sensing elements 160 during dose delivery. Sensing elements 160 are operable to detect the relative angular position of magnet 152. Sensing elements 160 may include inductive sensors, capacitive sensors, or other contactless sensors when the ring 152 is a metallic ring. Magnetic sensor system 150 thereby operates to detect the total rotation of flange 38 relative to dose button 56, and therefore the rotation relative to housing 12 during dose delivery. In one example, magnetic sensor system 150 including magnet 152 and sensor 158 with sensing elements 160 may be arranged in the modules shown in FIGS. 13, 25 and 35.

Figure 11B:
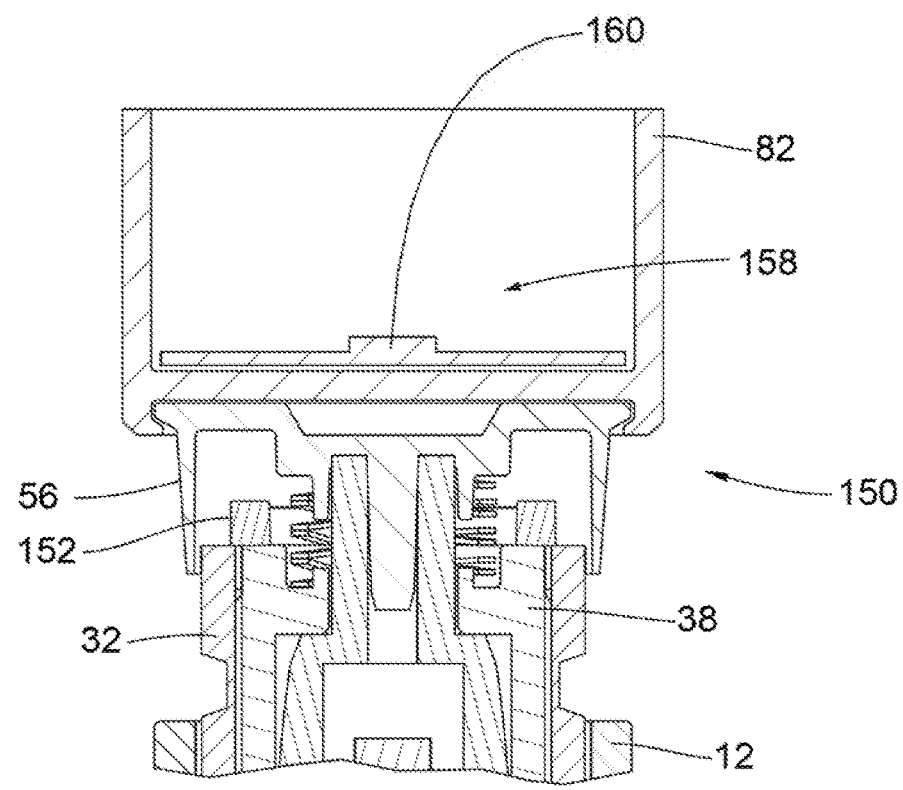

In one embodiment, magnetic sensor system 150 includes four sensing elements 160 equi-radially spaced within module 82 to define a ring pattern as shown. Alternative numbers and positions of the sensing elements may be used. For example, in another embodiment, shown in FIG. 11B, a single sensing element 160 is used. Further, sensing element 160 in FIG. 11B is shown centered within module 82, although other locations may also be used. In another embodiment, shown in FIG. 33 and FIG. 40, for example, five sensing elements 906 equi-circumferentially and equi-radially spaced within the module. In the foregoing embodiments, sensing elements 160 are shown attached within module 82. Alternatively, sensing elements 160 may be attached to any portion of a component rotationally fixed to dose button 56 such that the component does not rotate relative to housing 12 during dose delivery.

For purposes of illustration, magnet 152 is shown as a single, annular, bi-polar magnet attached to flange 38. However, alternative configurations and locations of magnet 152 are contemplated. For example, the magnet may comprise multiple poles, such as alternating north and south poles. In one embodiment the magnet comprises a number of pole pairs equaling the number of discrete rotational, dose-setting positions of flange 38. Magnet 152 may also comprise a number of separate magnet members. In addition, the magnet component may be attached to any portion of a member rotationally fixed to flange 38 during dose delivery, such as skirt 42 or dose dial member 32.

Alternatively, the sensor system may be an inductive or capacitive sensor system. This kind of sensor system utilizes a sensed element comprising a metal band attached to the flange similar to the attachment of the magnetic ring described herein. Sensor system further includes one or more sensing elements, such as the four, five, six or more independent antennas or armatures equi-angularly spaced along the distal wall of the module housing or pen housing. These antennas form antenna pairs located 180 degrees or other degrees apart and provide a ratio-metric measurement of the angular position of metal ring proportional to the dose delivered.

The metal band ring is shaped such that one or more distinct rotational positions of metal ring relative to the module may be detected. Metal band has a shape which generates a varying signal upon rotation of metal ring relative to antennas. Antennas are operably connected with electronics assembly such that the antennas function to detect positions of metal ring relative to sensors, and therefore relative to housing 12 of pen 10, during dose delivery. Metal band may be a single, cylindrical band attached to the exterior of the flange. However, alternate configurations and locations of the metal band are contemplated. For example, the metal band may comprise multiple discrete metal elements. In one embodiment the metal band comprises a number of elements equal to the number of discrete rotational, dose-setting positions of flange. The metal band in the alternative may be attached to any portion of a component rotationally fixed to flange 38 during dose delivery, such as dial member 32. The metal band may comprise a metal element attached to the rotating member on the inside or the outside of the member, or it may be incorporated into such member, as by metallic particles incorporated in the component, or by over-molding the component with the metal band. MCU is operable to determine the position of the metal ring with the sensors.

MCU is operable to determine the start position of magnet 152 by averaging the number of sensing elements 160 (for example, four) at a maximum sampling rate according to standard quadrature differential signals calculation. During dose delivery mode, sampling at a targeted frequency is performed by MCU to detect the number of revolutions of magnet 152. At end of dose delivery, MCU is operable to determine the final position of magnet 152 by averaging the number of sensing elements 160 (for example, four) at a maximum sampling rate according to standard quadrature differential signals calculation. MCU is operable to determine from calculation of the total rotational angle of travel from the determined start position, number of revolutions, and the final position. MCU is operable to determine the number of dose steps or units by dividing the total rotational angle of travel by a predetermined number (such as 10, 15, 18, 20, 24) that is correlated with the design of device and medication.

In one aspect, there is disclosed a modular form of the dose detection system. The use of a removably attached module is particularly adapted to use with a medication delivery device in which the actuator and the dose setting member both include portions external to the medication device housing. These external portions allow for direct attachment of the sensing component to the actuator, such as a dose button, and a sensed component to a dose setting member, such as a dose skirt, flange, or dial member, as described herein. In this regard, a "dose button" is used to refer more generally to a component of a medication delivery device which includes a portion located outside of the device housing and includes an exposed surface available for the user to use in order to deliver a set dose. Similarly, a dose "skirt" refers more generally to a component of a medication delivery device which is located outside of the device housing and which thereby has an exposed portion available for the user to grasp and turn the component in order to set a dose. As disclosed herein, the dose skirt rotates relative to the dose button during dose delivery. Also, the dose skirt may be rotationally fixed to the dose button during dose setting, such that either the dose skirt or dose button may be rotated to set a dose. In an alternative embodiment, the delivery device may not include a dose skirt, and a user may grasp and rotate the actuator (e.g., dose button) for dose setting. In some embodiments, with a dose detection module attached to the actuator and/or the dose skirt, the dose detection module may be rotated to thereby rotate the dose setting member of the delivery device to set a dose to be delivered.

It is a further feature of the present disclosure that the sensing system of dose detection system 80 may be originally incorporated into a medication delivery device as an integrated system rather than as an add-on module.

The foregoing provides a discussion of various structures and methods for sensing the relative rotation of the dose setting member relative to the actuator during dose delivery. In certain embodiments of medication delivery devices, the actuator moves in a spiral fashion relative to the pen body during dose setting. For illustrative purposes, this disclosure describes the dose detection system in respect to such a spiraling actuator. It will be appreciated by those skilled in the art, however, that the principles and physical operation of the disclosed dose detection system may also be used in combination with an actuator that rotates, but does not translate, during dose delivery. It will also be understood that the dose detection system is operable with other configurations of medical delivery devices provided that the device includes an actuator which rotates relative to a dose setting member during dose injection.

Detection systems may also be employed with the module for identifying a characteristic of the medication to be administered by a pen injector. Pen injectors are used with a wide variety of medications, and even with various types of a given medication as already described. For example, insulin is available in different forms depending on the intended purpose. Insulin types include rapid-acting, short-acting, intermediate-acting and long-acting. In another respect, the type of the medication refers to which medication is involved, e.g., insulin versus a non-insulin medication, and/or to a concentration of a medication. It is important not to confuse the type of medication as the consequences may have serious implications.

It is possible to correlate certain parameters based on the type of a medication. Using insulin as an example, there are known limitations as to the appropriate amount of a dose based on factors such as which type of insulin is involved, how the type of insulin correlates to the timing of the dose, etc. In another respect, it is necessary to know which type of medication was administered in order to accurately monitor and evaluate a treatment method. In one aspect, there is provided a sensor system which is capable of differentiating the type of medication that is to be administered.

For determining the medication type, a module is provided which detects a unique identification of the type of medication, such as, for example, any one of the medications described herein, contained in the medication delivery device. Upon mounting the module to the medication delivery device, e.g., pen injector, the module detects the type of medication and stores it in memory. The module is thereafter able to evaluate a medication setting or delivery in view of the type of medication in the pen, as well as previous dosing history and other information. One example of detecting the type of medication is described later with identification sensor 680 in FIG. 29. Another example is described next.

This medication type detection is useful with a variety of sensor systems which are operable to detect a predetermined angular position of sensed elements relative to an alignment feature. These sensor systems include those previously disclosed herein. It is a further aspect that this medication type determination is readily combined with sensor systems for detecting the amount of a dose delivery. The two systems may operate independently or in concert with one another.

In a particular aspect, the sensor system used for detecting dose delivery is also used to identify the medication type. For example, FIGS. 10A-10B and FIGS. 11A-11B and related text describe a magnetic sensor system which includes sensing elements 160 and a magnet 152 to determine the amount of a delivered dose. Magnet 152 has a unique configuration such that the sensor system is able to detect specific angular positions of magnet 152 relative to the sensing elements.

The illustrative sensor system 230 is also useful as a system which is integrated into a medication delivery device, rather than being provided as a removable module. Referring to FIG. 12, there is shown a medication delivery device 310 substantially the same as device 10 in FIGS. 1-4. Medication delivery device 310 includes device body 11 and dose setting member 30 comprising dose dial member 32, flange 38, and skirt 42. These components are configured to function as previously described. Actuator 50 comprises clutch 52 and dose button 56 attached thereto. Dose button 56 is rotationally fixed with dose setting member 30 during dose setting. For dose delivery, this rotational fixing is disengaged, and dose setting member 30 rotates relative to dose button 56 in proportion to the amount of dose delivered. Other embodiments of the dose detection systems described herein may be incorporated integrally into the device 310.

Figure 13:
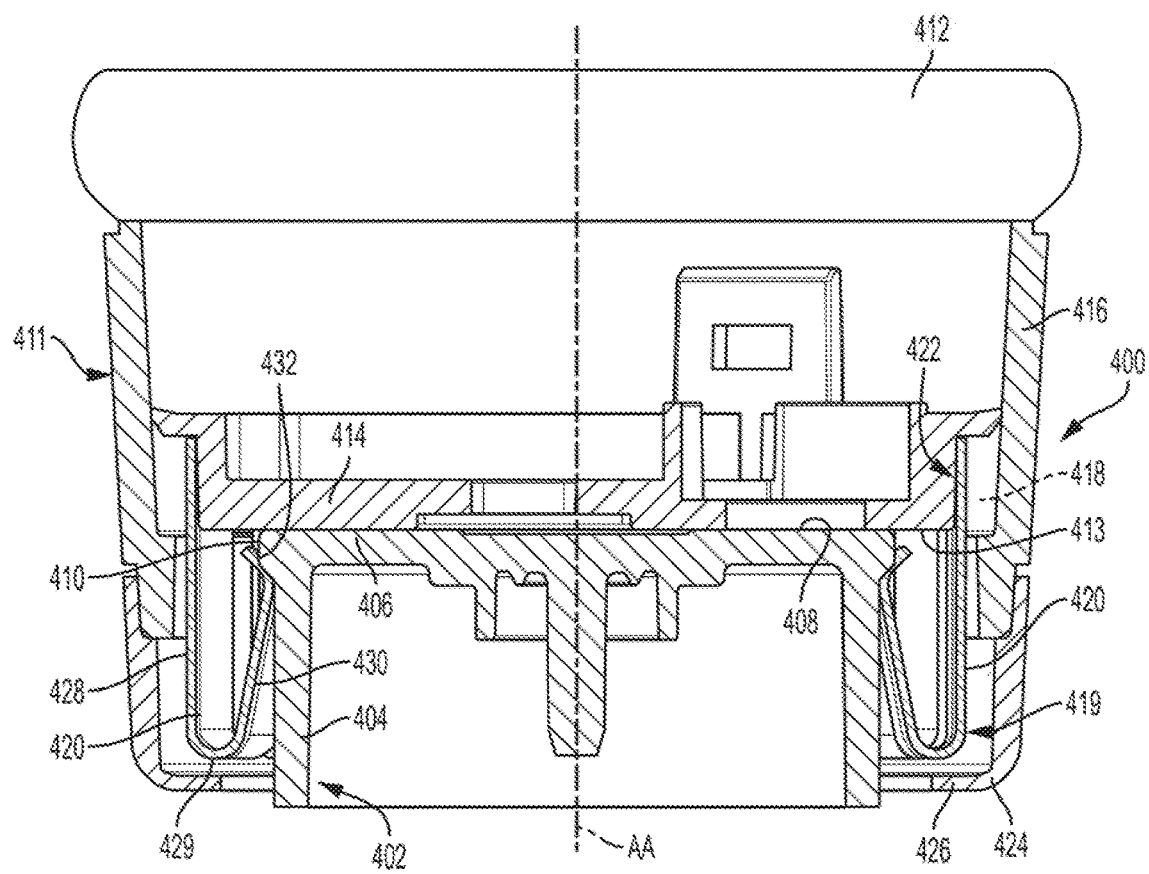
FIG. 13 is a side, diagrammatic cross-sectional view of a dose detection system module according to another exemplary embodiment attached to the proximal portion of a medication delivery device.
Figure 14:
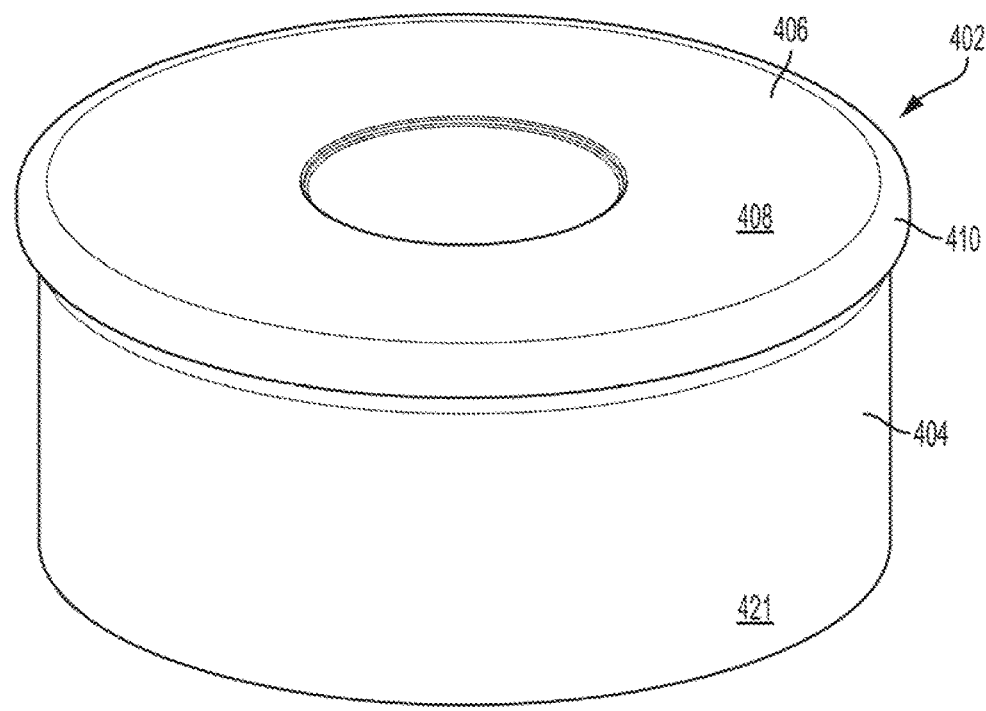
FIG. 14 is a perspective view of an example of a dose button for a medication delivery device.

FIGS. 13-15 depict another example of the module, now referenced as module 400, that is attachable to a medication delivery device having the dose button 402 including a cylindrical sidewall 404 and a top wall 406 disposed coaxially about a device axis AA. Top wall 406 of dose button 402 includes an upper or proximal axial surface 408 which is directly pressed by a user to deliver a dose when module 400 is not mounted on dose button 402. Top wall 406 extends radially-outward of side wall 404, thereby forming a lip 410. Sidewall 404 extends between the upper surface 408 and a distal end as shown in FIG. 14.

Module 400 includes a housing 411 generally comprising a proximal wall 412 and a distal wall 414. Module 400 further includes perimetric sidewall 416 extending between and forming a compartment 418 with proximal wall 412 and distal wall 414. When mounted to a dose button, a distally facing axial surface 413 of distal wall 414 is illustratively received against upper surface 408 of dose button 402. The walls of module 400 are shown in a particular configuration, but the walls may be of any desired configuration suited to forming compartment 418. In one example, compartment 418 may be configured to resist entry of moisture and particulate matter. In another example, compartment 418 may be configured to resist dust and debris but not resist entry of moisture directly. Industry standards provide guidance for the different standards for moisture and dust protection.

Having similar components as module 82 in FIGS. 5-6, compartment 418 may include a various desired components for use with the medication delivery device, as disclosed herein. Such components may include, for example, measurement or other sensors, one or more batteries, MCU, a clock timer, memory, and a communications assembly. Compartment 418 may also include various switches for use as described hereafter.

Any of the modules described herein can be removably coupled to any of the dose buttons described herein via an attachment element 419 coupled to module housing 411. Attachment element 419 includes a plurality of distally extending arms 420. As shown generally in FIG. 13, module 400 is attached to dose button 402 by arms 420 which are attached to and extend distally from housing 411. In an exemplary embodiment arms 420 are equi-radially spaced around dose button 402. Arms 420 are depicted as being attached to distal wall 414 at attachment location 422. Alternatively, arms 420 may be attached to module 400 at other locations, such as at sidewall 416. Sidewall 416 may include a distal portion 424 disposed radially outward from arms 420 which extends distally from sidewall 416 a distance farther than the distalmost extension of arms 420 to at least partially or fully cover arms 420 to inhibit tampering or access to arms when mounted to device. Distal portion 424 may include an inwardly-extending portion 426 which further encloses arms 420. Alternatively, distal portion 424 may be provided as a member which is slidable relative to sidewall 416.

Arms 420 are configured to move over lip 410 of dose button 402 and to provide frictional engagement with a radially outward facing surface 421 of sidewall 404. Arms 420 include a first portion 428 extending axially and configured to extend beyond lip 410. Arms 420 further include a bearing portion 430 extending radially-inward of first portion 428 and received against radially outward facing sidewall 404 of dose button 402. Portions 428, 430 may be joined by a rounded base 429 coupled between them to form a "J" shape with the first portion 428 forming the staff portion and the base and bearing forming the hook end. Bearing portion 430 may include an axially-bearing portion 432 received against the underside of lip 410. This provides added resistance to proximal displacement of module 400 relative to dose button 402. However, the engaged surfaces of the underside of lip 410 and axially-bearing portion 432 may be provided with angled surfaces to facilitate removal of module 400 when desired. In one example, each of arms 420 is radially movable to clear the lip 410 during attachment to and detachment from dose button. In one example, both portions 428, 430 flex outward, and in some examples, only one of the first portion 428 or bearing portion 430 flexes outward to move over lip. Arms 420 may be biased in a radially inward configuration and may be deflected or pivoted outward about attachment location 422. In the biased configuration, arms 420 are adapted and sized to apply radial normal force against a number of engagement spots along the surface of sidewall 404 that is suitable for axial retention to dose button 402, as well as torque transmission (without or little acceptable slip) during dose setting and/or dose dispensing.

Figure 16:
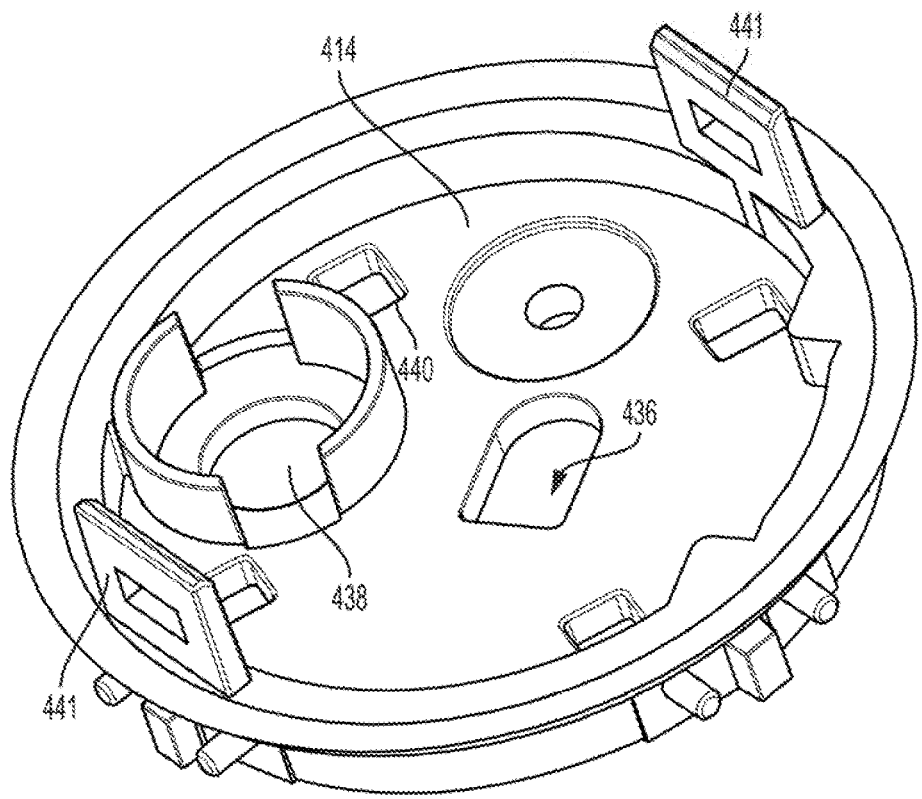
FIG. 16 is a perspective proximal view of a component of the subassembly in FIG. 15.
Figure 17:
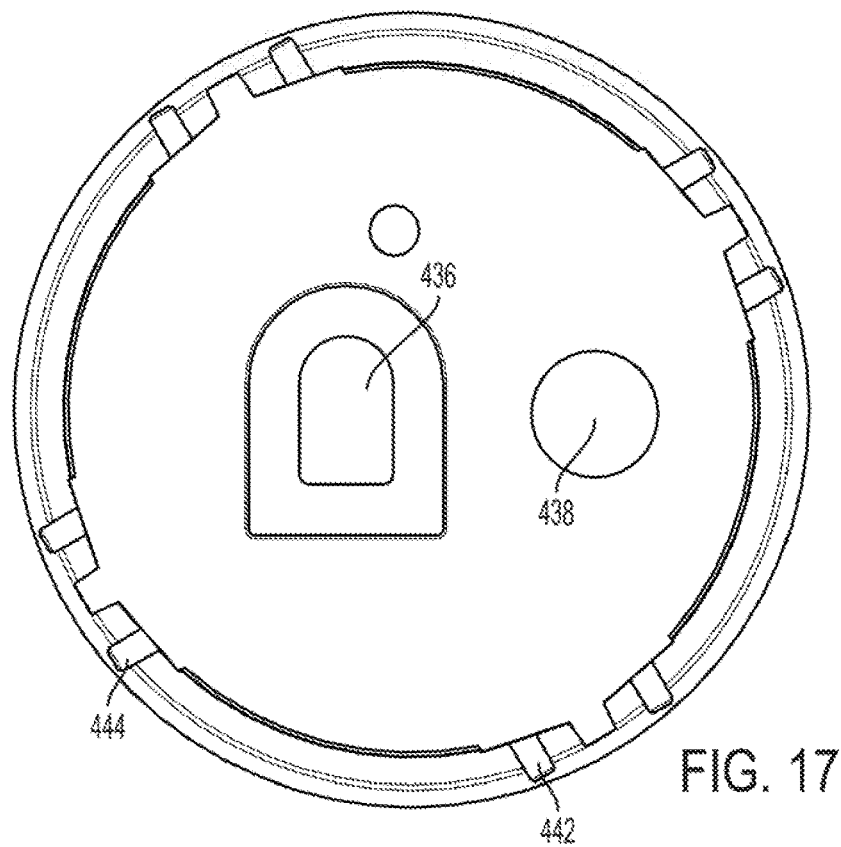
FIG. 17 is a distal view of the component in FIG. 15.

An assembly 434 including arms 420 attached to distal wall 414 (shown as molded or manufactured component) is shown in FIG. 15. For purposes of fabrication, arms 420 and other components are combined with distal wall 414 (shown as a radially outward surface of wall 414), which is then attached to other parts of module 400. FIGS. 16-17 shows the distal wall 414 and some of its component parts. Distal wall 414 includes an aperture 436 formed therein to allow an identification sensor, described hereafter, to view the upper surface 408 of dose button 402. Light guide aperture 436 may have a variety of shapes, including the "D" shape as shown. Another opening 438 formed therein accommodates a presence switch, also described hereafter, to enable module 400 to determine when it is mounted upon dose button 402. In one example, the opening 438 is omitted from distal wall 414. Sensor receiving recessed locations 440 are provided in the distal wall for radially spaced placement of four measurement sensors, e.g., magnetic, inductive, or capacitive sensing elements as previously disclosed. The depth of the recesses 440 is sized to place the sensors in close proximity to the sensed component, while leaving sufficient material thickness to structurally support the sensors during manufacturing and use. Recesses 440 allow for secure fixing of the sensors so that the sensors maintain their respective locations for more consistent sensing capability. Recesses 440 are arranged to place the sensors are disposed equi-angularly (four sensors at 90 degrees apart (as shown); five sensors at 72 degrees apart, six sensors at 60 degrees apart, etc.) relative to one another and equi-radially disposed from the module longitudinal axis. Walls defining the recesses 440 are also structured to disposed the sensors along a common plane. Other ports may be provided for venting of the module. Attachment axial wings 441 may be provided for coupling distal wall 414 to a complementary attachment feature of the module housing.

The number of arms 420 may vary, such as, for example, in the range of 3 to 36, due to desired axial retention force and/or torque transmission. Arms 420 are depicted as being attached to distal wall 414 at attachment location 422 defines by posts, which may be a single post or a pair of posts 442, 444 as shown. Assembly 434 is shown including sixteen arms 420. Assembly 434 is shown including four pairs of mounting posts 442, 444 that are circumferentially spaced around the perimeter of distal wall 414. Each pair of mounting posts is configured to support a circumferential segment 445 having a plurality of arms, such as four arms each. Each segment 445 includes mounting holes 446 which receive the mounting posts 442, 444. Once received in position, the mounting posts 442, 444 are used to heat stake the arm segments to distal wall 414 in a securely fixed manner.

The attachment of the arms 420 to the housing allows for fabrication of the arms from a variety of materials. These materials may be selected to obtain desired features of strength, elasticity, durability and the like. For example, it has been found that beryllium copper has advantageous properties for use as the arms. The separate attachment also provides flexibility as to the placement of the arms relative to the dose button. For example, the arms may be mounted to various walls of the module, including distal wall 414, sidewall 416, or distal portion 424.

Figure 18:
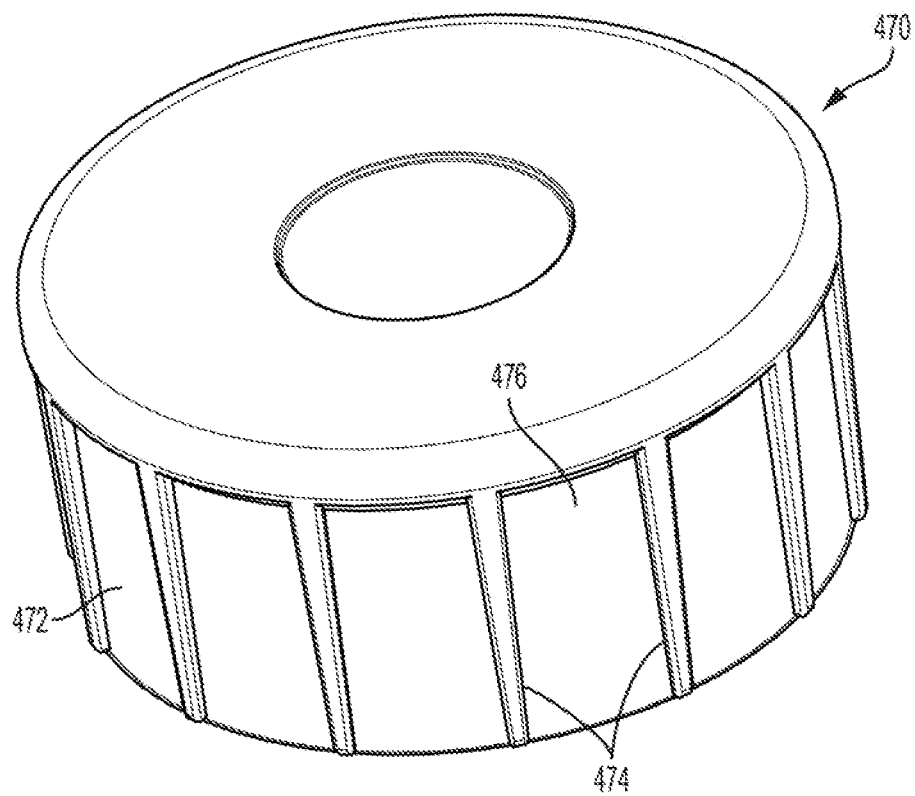
FIG. 18 is a perspective view of another example of a dose button for a medication delivery device.
Figure 19:
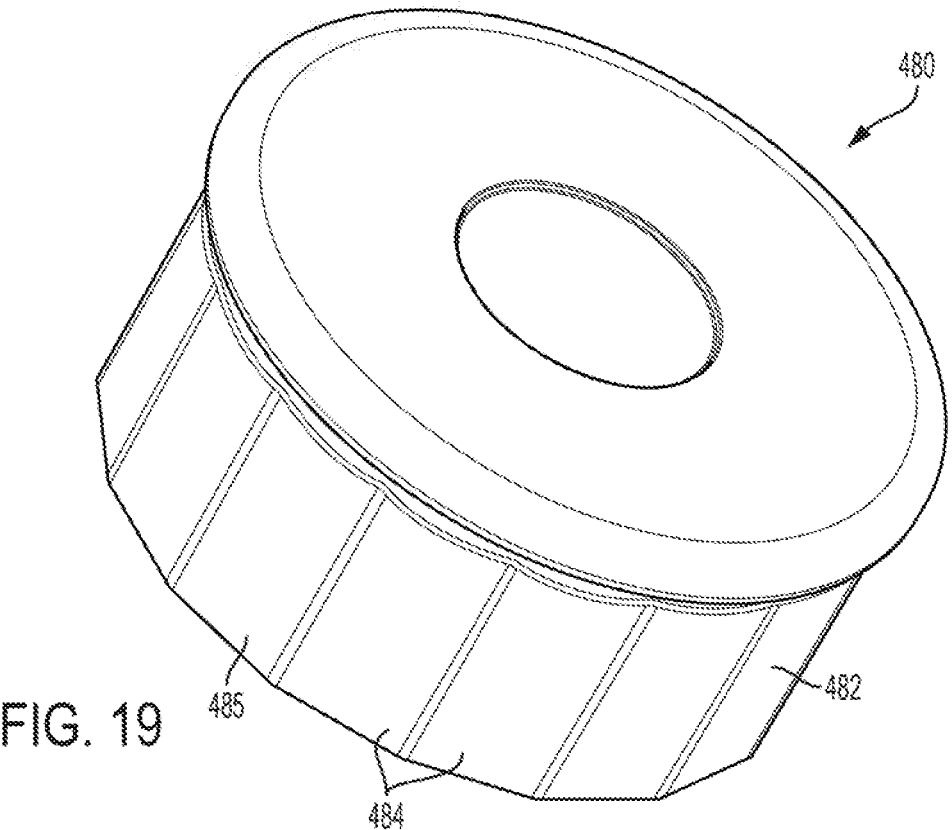
FIG. 19 is a perspective view of another example of a dose button for a medication delivery device.

Arms 420 may be suitable for different configurations of surface 421 of dose button 402. FIG. 14 illustrates the surface 421 have a smooth (without ribs or grooves or planar variations). The surface 421 of button may include surface features to enhance torque transmission with arms 420. Other embodiments may be used for the interaction between the arms and the perimetric wall of the dose button. FIG. 18, for example, shows another example of a dose button 470 for a device including a sidewall 472 having spaced, axially-extending ridges 474, forming a series of recesses 476 therebetween. In this embodiment, portions of arms 420 can be receivable within recesses 476. Arms 420 may be suitable for another configuration of ridges shown in FIG. 22. The circumferential width of recesses 476 may be sized to receive the circumferential width of arms 420. The sizing may allow for a snug fit or may allow some circumferential freedom of arm movement. The presence of the adjoining ridges provides further assurance that the module will not rotate relative to the dose button during use. FIG. 19 shows an alternate design in which dose button 480 includes a sidewall 482 provided in a polygonal shape, thereby defining a series of flat surfaces 484 for reception of the arms of the module. Separating adjacent flat surfaces 484 is a rounded axial joint 485. The use of a flat, smooth cylindrical surface avoids any issues regarding orientation of the module relative to the dose button, while the recessed and polygonal designs provide additional frictional engagement of the arms with the sidewall of the dose button.

FIGS. 20-24 illustrate another example of a module attachment subassembly, now referenced as unit 500, configured, when part of a module, to be removably coupled to any of the dose buttons described herein via an attachment element 519. Attachment element 519 is coupled to a tubular attachment housing 511 (although other parts of the module housing are omitted, aspects of these parts to define a full module housing are shown in FIG. 13 and FIG. 25). Attachment housing 511 with the attachment element 519 may form a part of the module 600 as will be described later. Attachment element 519 includes a plurality of distally extending arms 520. As shown generally in FIG. 20, unit 500 when part of a module is attached to another example of dose button 502 by arms 520 which are attached to and extend distally from housing 511, and in particular distally from annular housing portion 517 of housing 511 at recessed areas defined by the distal wall 514. The annular housing defines a cavity to receive for example at least partially electronics. In an exemplary embodiment arms 520 are equi-radially spaced around dose button 502. Arms 520 are depicted as being coupled to and depending from a distal wall 514 of attachment housing 511.

Figure 21:
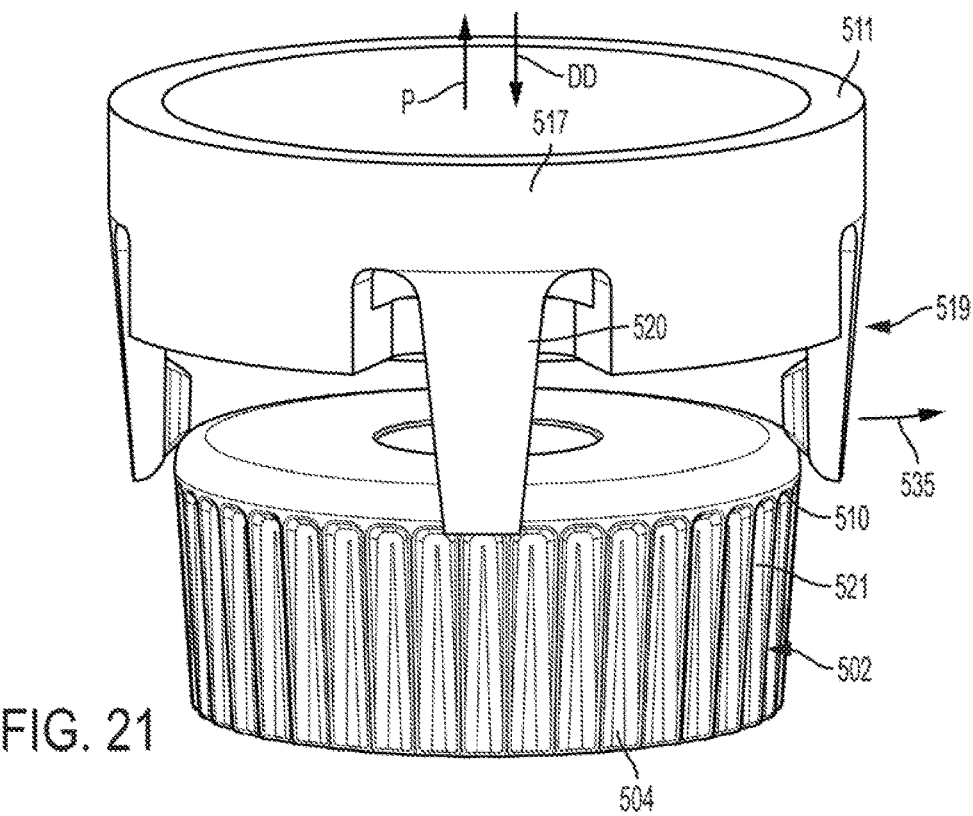
FIG. 21 is a perspective view of the subassembly of the module housing of the dose detection system module removed from the dose button.

FIG. 21 depicts arms 520 being resiliently configured to move over lip 510 of dose button 502 and to provide frictional engagement with a radially outward facing surface 521 of sidewall 504 of dose button 502. With additional reference to FIG. 23, arms 520 include a bearing portion 530 extending radially-inward of the axial body of arms 520 and received against radially outward facing sidewall 504. Bearing portion 530 may include a protruding body 531 extending radially inward from the interior surface of arm 520.

Figure 24:
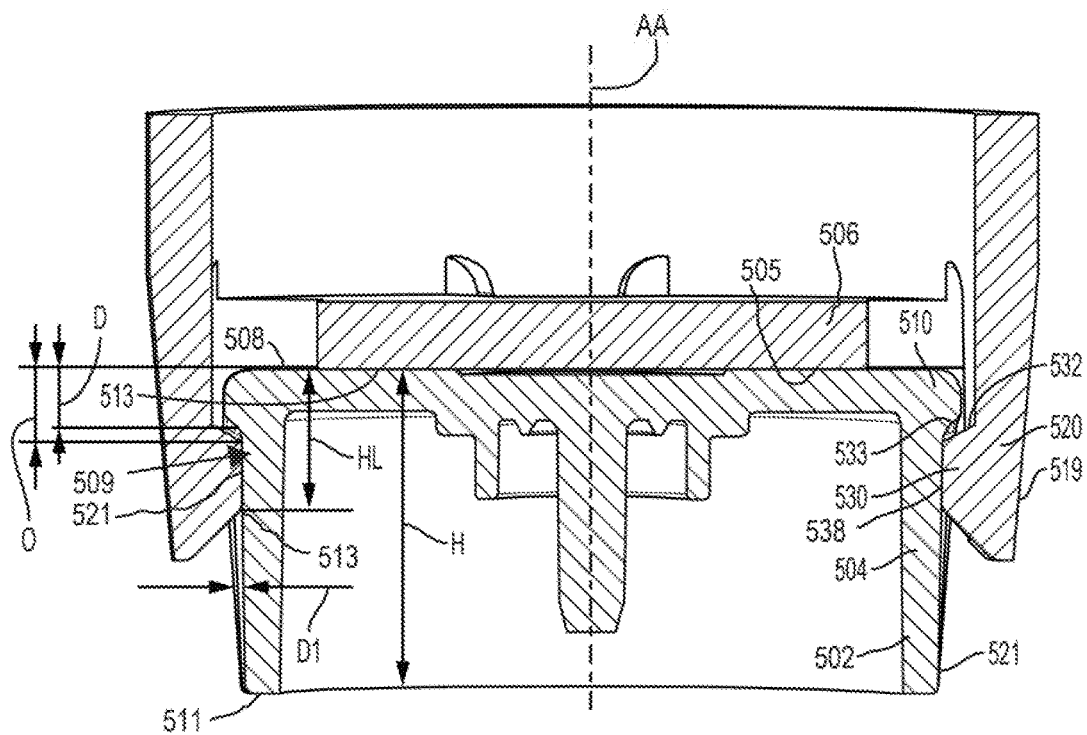
FIG. 24 is a cross-sectional view of the subassembly of the module housing of the dose detection system module mounted to the dose button in FIG. 20.
Figure 25:
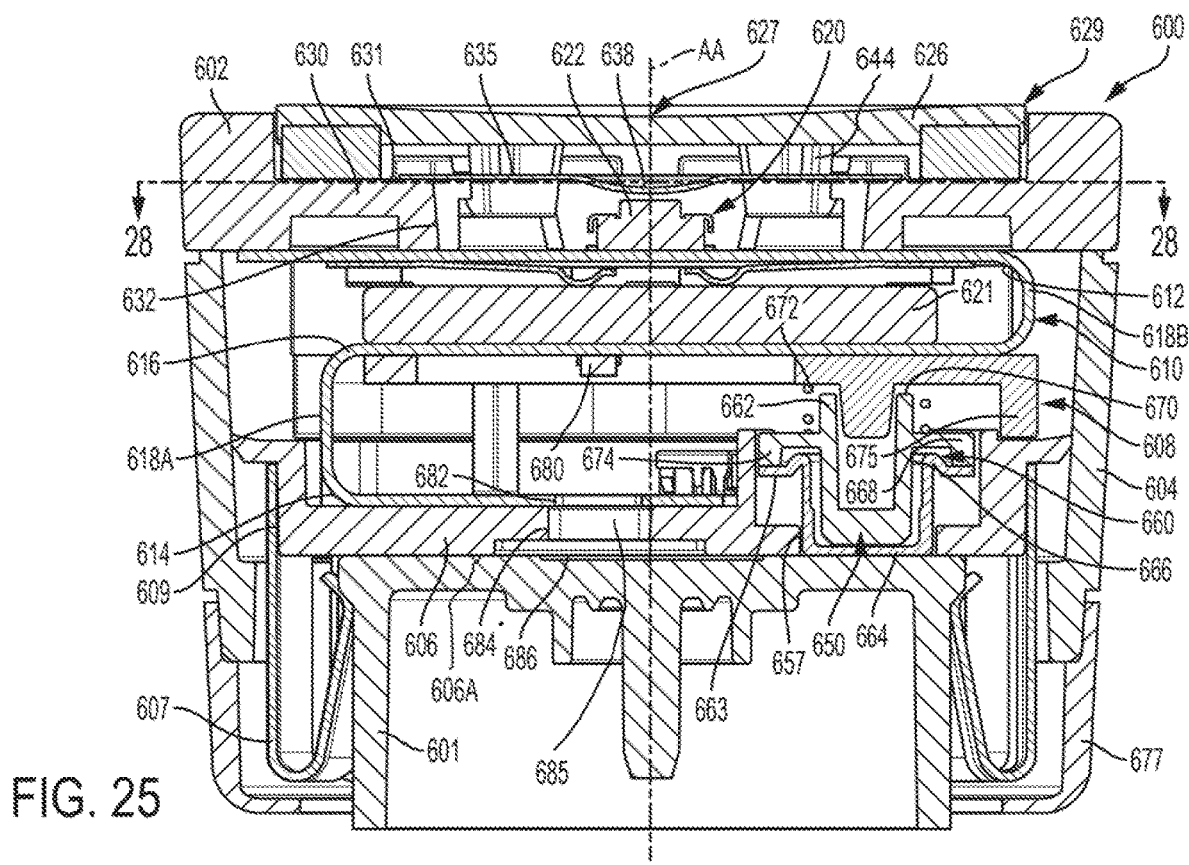
FIGS. 25-26 are side, diagrammatic cross-sectional views of a dose detection system module according to another exemplary embodiment attached to the proximal portion of a medication delivery device.

Protruding body 531 may include an axially-bearing surface 532 to be received against or place in close proximity to the underside 533 of lip 510 shown in FIG. 24. This provides added resistance to proximal displacement of the module relative to dose button 502 when attached. Protruding body 531 of bearing portion 530 may include a distal facing end 537. The surface 532 and/or distal facing end 537 may be angled at any angle to give the protruding body 531 a tapered profile. Protruding body 531 may include a radially facing engagement surface 538 having an axial length extending between surface 532 and end 537. Engagement surface 538 may by planar, rounded (as shown), tapered or V-shaped. As shown in FIG. 23, protruding body 531 may have a smaller width than the width of the arm 520. In another example, the arms may include more than one protruding body arranged to fit within adjacent ridges or alternating ridges.

Figure 20:
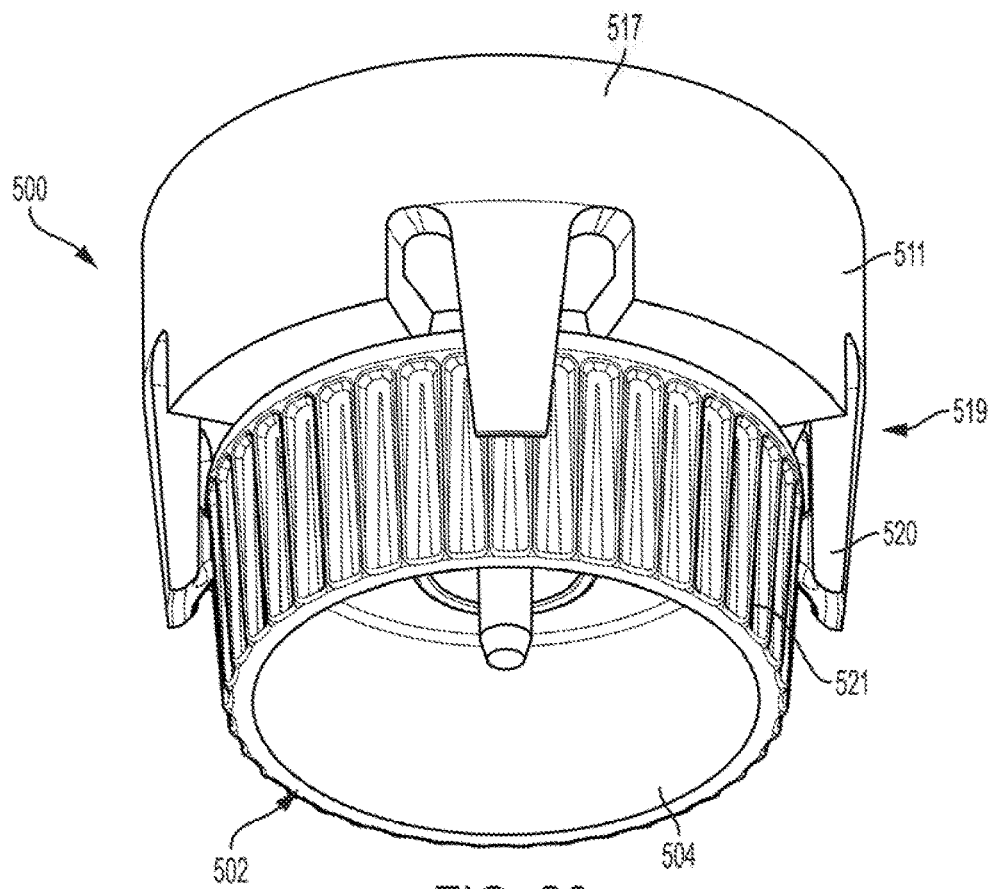
FIG. 20 is a perspective view of a subassembly of a module housing of another example of a dose detection system module mounted to another example of a dose button for a medication delivery device.

FIG. 22 depicts the sidewall 504 of dose button 502 includes a plurality of spaced, axially-extending ridges 545, forming a series of recesses 547 therebetween. Button 502 also includes a proximal wall with a proximal upper surface 508. At least a portion of the proximal surface 508 may have a color to correspond to a unique kind of medication and/or dosage. The button 502 with color is representative of all the other buttons described herein as those other buttons may have similar color schemes. To this end, any of the modules described herein can be attached to different kinds of pens, and with the use of color detection the module can communicate the identification information to an external device. The module and/or external device may determine a different number of units of medication delivered for the same amount of total rotation due to the pen having a unique rotational profile for a given medication and dosage. In one example, the entire upper surface 508 of the button 502 is a single color. In another example, a surface feature or region 507A, such as recess or a protrusion or the center of the button surface, may have a first color, and a region 507B adjacent to the surface feature or specific region may have a second color different than the first color. The medication identification sensing described herein may be directed to the first color or the second color depending the module's configuration. In this embodiment, at least a portion of the bearing portion 530 of arms 520 are receivable within recesses 547. In one example, the circumferential width of each of the recesses 547 may be sized to receive the circumferential width of engagement surface 538 of bearing portion 530, and in other embodiments, recesses 547 may be sized to receive a tip end portion of the engagement surface of any of the tips of the arms described herein, such, as, for example, as shown in FIG. 20. The circumferential width of each bearing portion 530 may be oversized to fit over the recesses 547, engaging adjacent ridges without going into the recesses. In one embodiment, the proximal extent 549 of the recesses 547 may extend within the radial lip 510. The depth D1 of the recesses 547, shown in FIG. 24, may be constant along the axial extent of the recess. In other examples, the depth of the recesses 547 may vary along the axial extent, such as, for example being sized to be deeper toward the proximal end than toward the distal end of recess 547. Arms 520 may also suitable for other button surfaces, such as, for example, shown in FIGS. 14, 18, and 19. The overhang axial distance O of axially-bearing surface 532 of arms 520 relative to the distally facing axial surface 513 of distal wall 514 may be larger than the axial depth D of the radial lip 502.

With reference to FIG. 24 the amount of extension length of the arms 520, beyond a plane defined by the distally facing axial surface 505 of distal wall 506 and orthogonal to the axis AA, may be sized to place the bearing portion 530 along the radially outward facing surface 521 of sidewall 504 of dose button 502. In one example, extension length is sized to place the bearing portion 530 along only a proximal upper portion 509 of the sidewall 504 such that a distal lower portion of the sidewall 504 remains unengaged by any portion of the arms. The dose button shown in FIG. 24 includes an axial height H measured between the upper surface 508 of the dose button 502 and the distal end 511 of the dose button 502. The distal end 513 of the bearing portion 530, that is, the distalmost part of the bearing portion 530 that is in direct engagement with the sidewall 504, of arms 520 engages the surface 521 of sidewall 504 at an axial distance HL, thereby placing the surface engagement portion 538 of bearing portion 530 between the radial lip 510 and the engagement location of distal end 513 against the sidewall. The bearing portion may axially extend between the underside of the rim 510 and the engagement location of the distal end 513 that is located along the upper half of the sidewall 504. Axial distance HL is measured between said plane defined by the surface 505 that is against the upper surface 508 of dose button 502 and such engagement location of the distal end 513, as shown in FIG. 24. In one example, the axial distance HL may be sized up to 50% of the axial height H of the dose button 502 to place the bearing portion 530 along the proximal portion 509 of sidewall 504. This position may reduce the spatial impact of the arms within the attached module placed the button. Engagement surface 538 of the bearing portion 530 is sized axially larger than the axial thickness of the radial lip 510 for greater radial force. The bearing portion 530 of the arms 520 in a more axially compact configuration as shown may reduce the amount of axial travel and friction causing forces of surface 538 of the bearing portion along the rim 510, and thereby reducing the attachment and/or detachment force for the user. A more axially compact bearing portion of the arms may also reduce the amount of duration for attachment and/or detachment of the module so that user is not left doubting whether attachment was successful.

FIG. 21 illustrates each of arms 520 is radially movable in a direction of arrow 535 to clear the lip 510 during attachment to (or moving module in a proximal direction P relative to the dose button) and detachment from dose button (or moving module in a distal direction DD relative to the dose button). Arms 520 may be biased in a radially inward configuration and may be deflected or pivoted outward about where the arms depend from the distal wall 514. In the biased configuration, arms 520 are adapted and sized to apply radial normal force against a number of engagement spots along the surface of sidewall 504 that is suitable for axial retention to dose button 502, as well as torque transmission (without or with little acceptable slip) during dose setting and/or dose dispensing. In other words, during dose setting the unit 500 that is coupled to button 502 is rotated in a first direction that moves the module/button farther away from the device housing.

With any of the attachment elements described herein, such as elements 419 and 519, the attachment force that the user applies in the distal direction DD may be less than the detachment force that the user applies in the proximal direction P. The detachment force may be in the range of 4 N to 30 N. In one example, the arms are configured such that the detachment force is at least 1.5 times the attachment force, and may be at least twice as large as the attachment force to inhibit inadvertent detachment of the module. In one example, the detachment force is over 20 N and the attachment force is under 11 N. In other examples, once the module is attached to the device, a small degree of slippage of the bearing portions along the dose button due to torqueing from dose setting may be permissible in order to avoid over-torqueing and potential damage to the dose setting device components.

The arms 520 and housing 511 may be formed as an integral unit, such as with molding of a plastic material, such as an acetal thermoplastic (for example, Delrin®), or polycarbonate material (for example, Makrolon®). Such an integral unit 561 is shown in FIG. 23. The plastic materials may be selected to obtain desired features of strength, elasticity, durability and the like. Alternatively, the arms 520 may be separately made from the housing and later attached via an adhesive or welding. The number of arms 520 may vary. In the example shown, there are four arms positioned circumferentially spaced equally apart. In some examples, three arms may be provided, in other examples, 5, 6, 7, or 8 arms may be provided.

The arms described herein, such as arms 420 or 520, provide a convenient and effective attachment of the module to the dose button. As the module is intended for use on multiple medication delivery devices, the module attachment allows for ready attachment and removal of the module relative to the dose button. This derives from the arms described herein having suitable configurations and physical properties to set the amount of force required to attach/detach the module. The arms described herein are also configured to have sufficient durability for repeated attachments to medication delivery devices, and to retain elasticity to provide proper securement and retention to the button without the use of a separate retainer piece, such as a coiled spring or ring, disposed along the outside to provide radially compressive force.

Once mounted to a medication delivery device such as, for example, with the use of any one of the attachment elements 419 or 519, the module is frictionally engaged with the dose button. This allows for use of the module to rotate the dose button as desired, such as during dose setting for some medication delivery devices. The surface engagement of the bearing portions of the arms described herein may be controlled through various parameters. Frictional engagement depends on such factors as the force applied normal to the module surface and the coefficient of friction applicable for the contacting surfaces. The applied radial force is dependent, inter alia, on the sizes and shapes of the arms, the elasticity and resilience of the arms, and other factors. The disclosed attachment elements allow for selection among these and other parameters in order to provide the desired balance to frictionally lock the module with the dose button for rotation, and to allow for ready attachment and detachment of the module relative to the dose button.

Any of the modules described herein may include one or more switches to facilitate use of the module, even though the following description is related to the module 600. As previously described, the module is releasably attached to a medication delivery device. When desired, the module is removed from one medication delivery device and then is useful in conjunction with another medication delivery device. One skilled in the art would appreciate that various attachment elements described herein may be used for such coupling to the device. Referring to FIGS. 25-28, the module 600 includes a proximal wall assembly 602, sidewall 604 and distal wall 606. Walls 602, 604, 606 of module 600 thereby defines an internal compartment 608 configured to house an electronics assembly 610. Wall 602 may include a transparent or translucent material around the upper edge to provide a light guide when LEDs are employed.

Although the attachment element 607 is illustratively shown as the attachment element 419 in FIG. 15, it should not be limiting as module 600 can also be provided with any other attachment unit described herein. In such configuration, proximal end opening of the tubular attachment housing 511 is sized to fit over the circumferential outer surface 609 of distal wall 606 with a friction fit or otherwise securely fixed. In this configuration, distal wall 606 is illustratively shown in FIGS. 16-17 as the distal wall 414 (with the feature such as, for example, openings 438, 436 and features 440, 441), with the exception of the posts 442, 444 and block protrusion disposed between the posts 442, 444 are omitted, thereby providing a smooth outer surface 606A of distal wall 606 that is sized and shaped to receive the unit 500.

FIGS. 25, 26, 27 and 29 show an example of electronics assembly 610 that may be used for any of the modules described herein. Assembly 610 includes a first distal segment 612, a second proximal segment 614, and a third intermediate segment 616 therebetween, each having electronically connected by connections and leads, shown generally at 618A-B. Segments 612, 614, 616 may be coupled coaxially disposed over one another in an "S" pattern. Battery 621 is shown axially disposed between the first and third segments 612, 616 and captured by resilient arms. The second segment 614 may include sensor pockets 623 defined therein for receiving the measurement sensors, such as, for example, sensing elements 160. Pockets 623 are aligned and inserted within recessed locations 440 of distal wall of module housing. Alternatively, instead of pockets 623, the measurement sensors may be coupled directly to the second segment circuit without the pockets.

Figure 27:
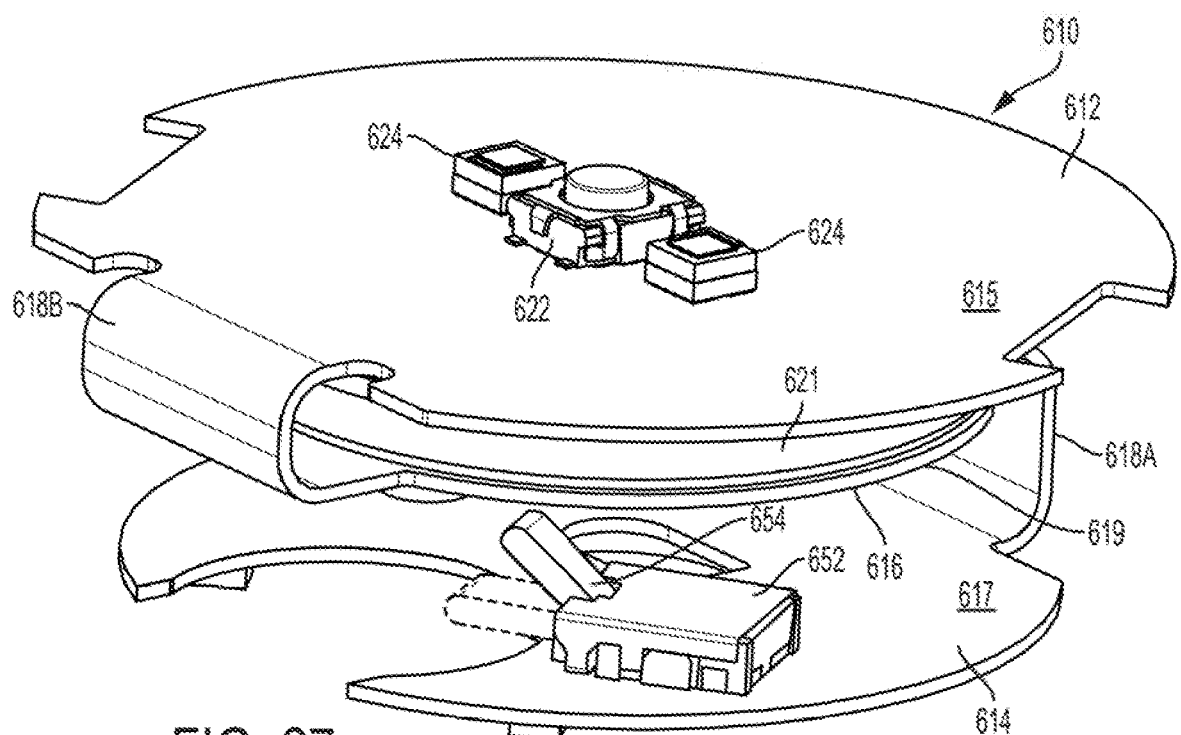
FIG. 27 is a perspective proximal view of an example of an electronics assembly of a dose detection system module.

In FIG. 27, the first segment 612 includes a proximal facing surface 615 and includes an example of a switch 622 of a wake-up switch system 620 mounted thereon. Module may include indicator elements 624, such as LEDs for indication of operator status of device and/or module. In one example, the indicator elements 624 are operably mounted to surface 615 of first segment 612. Activation of wake-up switch 622 may be used to turn on relevant electronics, such as those associated with the delivery of a dose. For example, wake-up switch 622 may turn on the measurement sensor, such as, for example, the sensing elements 160, involved in the measurement of a dose delivery generated by rotation of the sensed element. LEDs or other indicator elements, such as, audible speakers and/or vibration generators, may be used to notify the user of the progression of the system through completion of the dose delivery or notify the user between periods of dose delivery, such as, for example, battery charge indication. In one example, LEDs are mounted on the sides of the switch 622. Wake-up switch system may be configured to increase the power to the electronics from a low power state to a full operation state.

Any of the module described herein may include a wake-up switch system 620. The provision of such wake-up switch with a module may be optional. In one example, the module 600 shown in FIGS. 25-26 includes the wake-up switch system 620 which includes an axially movable segment 626 disposed within a recess defined in the upper surface of the proximal wall assembly 602. Wake-up segment 626 is able to move distally into module 600, and has a biased configuration as shown. Wake-up segment 626 may for example comprise a flexible disc-shaped member which is normally in a proximal position, or it may be a member that is biased proximally such as by springs (not shown). The material of the wake-up segment may allow for some deflection of the center 627 of the segment 626 relative to the circumferential edge 629 of the segment 626. Segment 626 may be a rigid member slidably disposed along walls defining a recess within the proximal portion 602 of the module housing. Segment 626 may include an anchoring segment (not shown) movably coupled to the module housing such that that when segment 626 is in its biased proximal position, segment remains within module housing without exiting the module. Walls 630 of proximal wall assembly 602 may be shaped to define a proximally facing axial surface 631 configured to define a physical stop or its distalmost position for the distal travel of the segment 626 from its biased proximal position. Walls 630 define a smaller sized portion of the throughbore 632 extending axially along the axis AA through the proximal wall 602.

When user distally actuates the wake-up segment 626, the axial force is sufficient to overcome the biasing force of the spring (not shown) and allow distal movement of the segment 626 until directly or indirectly causing activation of the switch system 620. This axial force to actuate wake-up is less than the axial force to cause actuation of the delivery device for dose delivery. In one example, segment 626 may be distally moved to engage the axial surface 631, while the walls 630 defining the throughbore 632 may be sized and shaped to allow continued axial deflection of segment 626 distally beyond the axial surface 630 such that there is sufficient to activate the switch system 620. The switch shown includes a mechanical switch or rubber dome switch, while other switches are contemplated such as electrical contacts. Switches described herein can be mechanically actuated or triggered by engagement with another component.

In one example, switch system 620 may further include a flexible shroud 635 configured to limit the travel of distal deflection of segment 626 when pressed by user to inhibit damage to the wake-up switch 620. Shroud 635 may be axially located between the segment 626 and the switch 622. Axial force from the user may be transmitted via the segment 626 to shroud 635 to cause central portion 638 of shroud 635 to axially deflect to engage the trigger of the switch 622. Shroud 635 may be configured to have a maximum distal extent of deflection. Such distal extent may be sized to allow engagement of the switch trigger but not farther to a position that may damage the switch. Shroud may have various sizes and shapes for such functionality.

Figure 28:
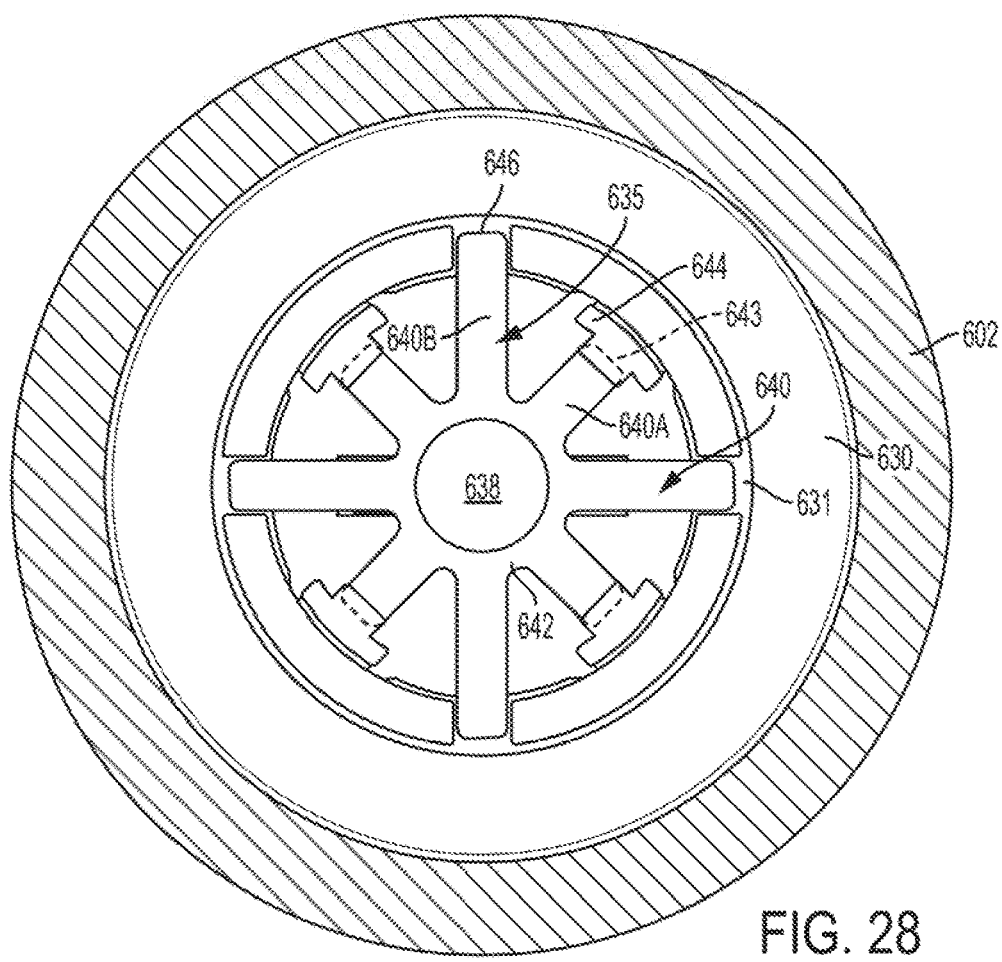
FIG. 28 is a cross-sectional axial view taken along lines 28-28 in FIG. 25.

FIG. 28 illustrates one example of shroud 635, including a plurality of radial legs 640 circumferentially disposed relative to one another, extending from a centerpoint of a hub 642 that surrounds central portion 638 of shroud. Centerpoint of hub is located coaxially with the axis AA. The hub 642 and central portion 638 may have any shape, and may be rectangular, oval, or circular as shown. The central portion 642 may include a concaved region that extends the hub in the distal direction relative to the surrounding hub region radially outside the concaved region. The end tips 643 of a first set of legs 640A may be coupled to anchor portions 644, such as for example the distal surface of anchor portions 644 having a slotted region sized and shaped to receive the size and shape of the tips 643. Anchor portion 644 extend distally from axially movable segment 626, which place the anchor portions 644 on top of the tips 643. Anchor portions 644 moves axially with segment 626 within throughbore 632 when user applies axial force thereto. Anchor portions 644 may be integrally formed with the segment 626 such as from molding or portions 644 may be formed separately and fixedly secured to the distal surface of segment 626. The tips 646 of a second set of legs 640B may be free or remain unengaged with the segment 626. The first set of legs 640A may be contacted by anchor portions 644 at equi-angularly locations to distribute the axial force and deflection to each of the legs 640. In one example, the first set of legs 640A are shorter in radial length than the longer second set of legs 640B. The first set of legs 640A may radially extend directly in between adjacent legs of the second set 640B. While all of the legs 640 may provide flexibility to the shroud 635, the free legs 640B can inhibit the shroud 636 to have the maximum distal extent of deflection while force is axially transmitted from segment 626 to the tips 643 via the anchor portions 644 to move the tips 643 within the throughbore 632. In the example shown, there are eight total legs 640 each disposed radially from the centerpoint by 45 degrees apart. The shorter fixed legs may be disposed 90 degrees apart, and the longer legs may be disposed 90 degrees apart and radially offset relative to the shorter fixed legs. Other numbers of legs and their relative positions may be used. In one example, the electronic assembly 610 is powered on from a sleep state by axial movement of segment 626 and shroud 635 caused by a user to a degree to contact the axial trigger of switch 622, such as, for example, without any distal movement of the module and/or dose button. In the alternative, the wake-up switch may include one or more leaf spring electrical contact elements that are biased away from contact with corresponding contact pads mounted on the first segment, and are movable for contacting the contact pads from force transmission via the member 626. In some examples, power on of electronic assembly occurs by simultaneous contact of each of the contact elements.

Figure 26:
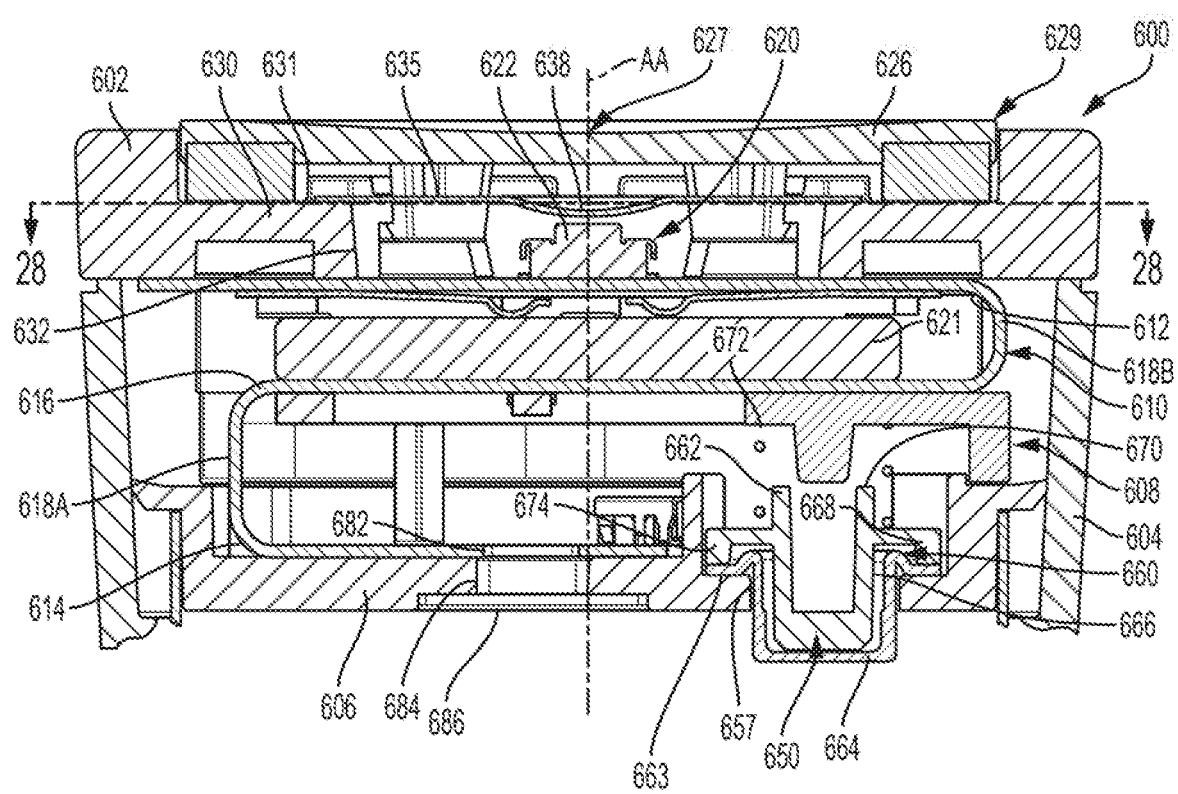

Any of the module described herein may include a presence switch system 650. The provision of such presence switch with a module may be optional. According to FIGS. 25, 26 and 27, module 600 includes presence switch system 650 mounted to distal wall 606 in a manner to detect when module 600 has been mounted to or removed from a medication delivery device. A presences switch 652 of system 650 is operably connected to the proximal face 617 of the second segment 614 of electronics assembly 610. Switch 652 includes a pivot switch arm 654 positioned at least partially overlapping the opening 657 (see opening 438 in FIG. 16) defined by distal wall 606. Distal wall 606 may include the same layout (or substantially the same layout) of features, such as, for example, openings 438, 436 and features 440, 441, shown in FIG. 16-17. Switch arm 654 of switch 652 has a biased position (shown in FIG. 27) and a distal position (shown in dashed lines). As represented in FIG. 25-26, switch system is movable from its biased distal position (as shown in FIG. 26) representing the absence of a medication device, to a proximal position (shown in FIG. 25) indicating that module 600 is mounted to a medication delivery device.

Presence switch system 650 includes a switch actuator 660 that is mounted to distal wall 606. Actuator 660 includes a first member 662 in a nesting relationship with a second member 664. The second member 664 has a cup configuration defining a cylindrical cavity to receive the first member 662. The second member 664 is slidably disposed through opening 657. The second member 664 includes an outer radial lip 663 along its proximal end and housed within module to enhance the inhibition of particulates and/or water ingress. Though the radial lip 663 is shown in FIG. 25 disposed away from distal wall, the radial lip 663 may remain engaged with the distal wall, such as shown in FIG. 26, when the module is attached to the device. The second member 664 may be made of elastomer or soft plastic material for flexibility. Second member 664 is movable within the module housing to a proximal position by direct engagement with the device when mounting the module to the device. First member 662 is shaped and sized to fit within the cavity defined by the second member 664. First member 662 includes a cylindrical body 666 extending axially between its proximal and distal axial ends. An outer radial rim 668 is shown extending from an intermediate segment of the first member body 666 such that a distal hat segment 670 is defined for insertion into a distal end of an actuator spring 672. The actuator spring 672 is fixedly secured at its proximal end to an internal component of the module housing, and the actuator spring's distal end is bearing on the rim 668 and movable therewith. Rim 668 may include a distal skirt 674 depending from the distal surface of the rim 668. In one example, the distal skirt 674 is coupled to the outer radial end of the rim. The rim 668 may comprise of diametrically disposed radial elements instead of a continuous circumferentially element.

Under the biasing force of the actuator spring 672, the first member 662 is in a nested position within the second member 664 and the rim 668 of the first member 662 is configured to contact and distally move the switch arm 654 to place the system at its biased distal position when the module is removed from the device. Switch system 650 in its distal position indicates electronically the module is not mounted to a device, and power limitations may be programmed into the processor to perform minimal functions. Skirt 674 may provide radial pressure along the lip 663 of the second member against the interior surface of distal wall 606 to enhance inhibition of particular ingress. Upon coupling the module to the device, the exterior end of the second member 664 with the first member 662 is in a nested position contacts the dose button of the device and force is transmitted to the rim via the body of the first member to overcome the force of spring 672, thereby causing the first and second members to move proximally within the module housing and thereby allowing the switch system to return to the proximal position. Switch system 650 in its proximal position indicates electronically the module is mounted to a device, and full power may be programmed into the processor to perform all functions.

Actuator 660 is biased in the distal direction by spring 672, and normally extends distally out of opening 657 when module 600 is not mounted to a medication delivery device. As shown somewhat diagrammatically in FIG. 25, mounting module 600 to any one of the dose buttons described herein, generally 601, causes the upper surface of dose button 601 to press actuator 660 proximally, and this movement in turn moves switch arm proximally, triggering presence switch 652. MCU of electronic assembly 610 recognizes the proximal position of switch arm 654 as a confirmation that unit 500 is mounted to a medication delivery device. In response, MCU wakes up or provides power to relevant components of electronics assembly 610 in preparation for use of the medication delivery device. When module 600 is subsequently removed, spring 672 moves actuator 660 back outside of distal wall 606 and switch arm 654 returns to its distal position identifying that module 600 is not mounted to a medication delivery device. MCU then returns the medication delivery device to a non-use state, such as by turning the module systems off or setting them in a sleep mode. One example of electronic assembly 610 is shown schematically in FIG. 46.

Figure 29:
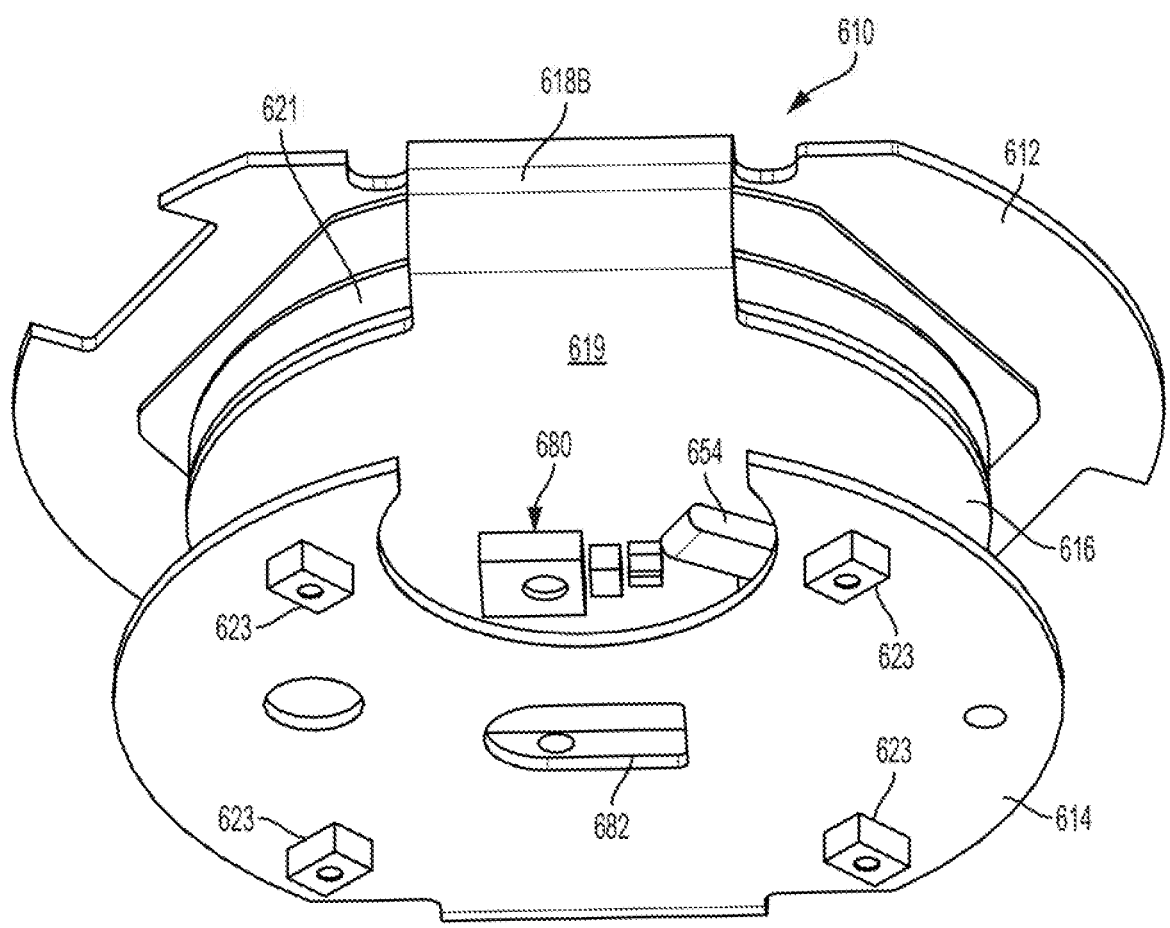
FIG. 29 is a perspective distal view of the electronics assembly in FIG. 27.

Illustratively, any of the modules described herein, such as module 600, may also include a sensor for identifying the type of medication delivery device, or the type of medication contained by the medication delivery device. Referring to FIG. 29, the identification sensor 680 is operably connected to the distal face 617 of the third segment 616 of the electronic assembly 610. The second segment 614 includes a window opening 682 defined therein. Identification sensor 680 is located over window opening 682 and aperture 684 of distal wall 606 (see aperture configuration and layout in aperture 436 in FIGS. 16-17) to be able to view the exposed surface of dose button 601. A recess 686 may be formed along the distal face of the distal wall 606 that overlaps the aperture 684. The recess 686 may receive a coupled lens or shield therein to aid in keeping debris out. Dose button 601 is provided with indicia visible to type sensor 680 through aperture 684. The indicia correlate to information concerning the medication delivery device, such as the type of device or the medication contained by the device. Identification sensor 680 reads the indicia and MCU recognizes the indicia as indicating the medication delivery device information. A light guide member 685 may be disposed within the aperture 684 to provide an optical path for the identification sensor. Securing light guide member 685 to distal wall 606, such as, by snap fit or adhesive or ultrasonic welding, can prevent light and sensing distortion caused by relative movement or vibration of the light guide member. Light guide member 685, which could be made from a transparent or translucent material, such as, for example, a polycarbonate, is shown extending axially between the upper surface of the button 601 and the opening 682. Recess 686 may be also be configured to receive an enlarged base portion of the light guide member 685.

By way of example, identification sensor 680 may comprise an RGB source(s) and sensor to detect color reflected from the dose button and the indicia may comprise different colors, each color being associated with specific information regarding the medication delivery device. Shielding elements may be provided to guide RGB light sources axially to button and to inhibit premature reading of light form sensor. Alternatively, the indicia may comprise grey scale, patterns, or other material that is optically recognizable. In addition, more than one type sensor may be employed to enhance the detection of information regarding the medication delivery device. In one embodiment, identification sensor 680, is positioned to detect the near-center or center of the proximal upper surface of dose button 601. The indicia may at the same time comprise patterns symmetrically positioned around the center of dose button 601, such as concentric color rings. With type sensor 680 so located, presence switch 652 is positioned displaced from the center of module 600.

In use, identification sensor 680 is activated with module 600 mounted to a medication delivery device. In one example, presence switch 652 detects the mounting of unit 500 on a medication delivery device and identification sensor 680 is activated at that time. Whenever collected, the sensed information concerning the medication delivery device may be stored and/or transmitted. Module 600 may then be moved to a lower power mode, such as after a predetermined time period, until reactivated during dose delivery.

As shown diagrammatically in FIG. 27, light indicator elements 624 (shown as LEDs), or other signaling devices, may notify the user of the various states of module 600, as well as other components including the medication delivery device itself. For example, a light signal may be used to indicate the type of medication delivery device or the medication contained by the medication delivery device. Another signal may be provided to confirm the proper placement of the module on the medication delivery device. Further, a signal may indicate the transition of module 600 to or from various states, such as waking up or sleeping conditions. Indicator elements may be operable to indicate in one form (such as green) successful attachment or in another form (such as amber) unsuccessful attachment between the module and the dose button of the device.

Assembling of the module may be configured in consideration of high volume manufacturing. The following steps may apply to any of the modules described herein, with general reference to FIGS. 25 and 27, and in alternative sequential order than what is described below. The distal wall 606 as a component is provided in the orientation and arrangement shown in FIG. 16. The switch actuator 660 with the first and second elements is inserted through opening 657 with the rim 668 of the first element sized to fit within the axial slots formed by upstanding walls surrounding and extending from the edge of opening (as shown in FIG. 16). Actuator spring 672 is placed on top of the actuator as shown in FIG. 25. The second segment 614 is placed with the interior of the distal wall component in alignment around the various features and openings formed along the distal component. An axial spacer component 675 (shown in FIG. 25) is placed over top of the second segment 614 and the distal wall. Spacer 675 includes alignment features to position the segments at a predetermined relative distance. The segments are then folded over along connection 618A in order to place the third segment 616 proximally on top of the spacer 675. Battery 621 is disposed on top of the third segment 616 and configured to operably provide power to all of the segments. The first segment 612 is then folded over along connection 618B in order to place the first segment 612 proximally on top of the battery 621. Attachment elements are then coupled to distal wall 606, either sliding over the distal wall 606 with the unit 500 with arms 520 with the bearing portion as described previously or attachment with the arms of the attachment element 419 as described previously. Proximal wall portion component 602 is positioned over the first segment 612 and includes attachment features for securely attaching to the distal wall 606 including attachment to the attachment axial wings shown in FIG. 16 to form a preassembly. Proximal wall portion 602 may include the axially movable segment 626 and the shroud 635 assembled together as descried herein prior to attachment with the sidewall 604. Tubular configured sidewall component 604 is slidably placed radially surrounding the preassembly and its proximal end fixedly secured to the proximal wall portion 606. Distal skirt portion 677 is fixedly secured to the distal end of the sidewall 604 to thereby form a completely assembled module.

Figure 47:
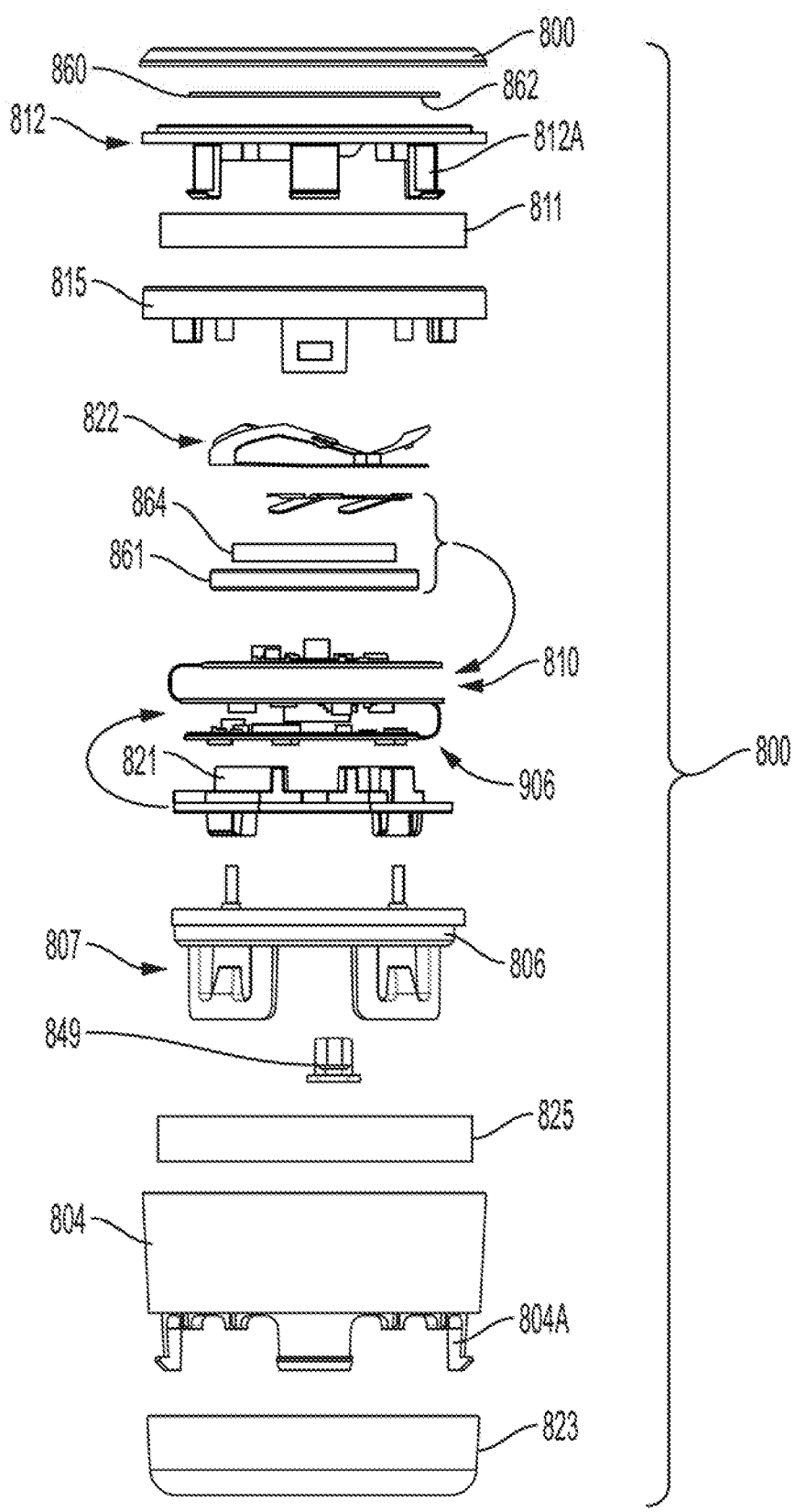
FIG. 47 depicts an exploded view of the module in FIG. 35 with its components axially displaced relative to one another.

Referring to FIG. 35, another embodiment of the module, now referred to as module 800, includes the proximal wall 802, sidewall 804 and distal wall 806. Walls 802, 804, 806 of module 800 thereby defines an internal compartment 808 configured to house the electronics assembly 810. Proximal wall 802 may have a disk shape and form the finger pad that user presses for device operation. Module may include a ring 812 of transparent or translucent material around the upper edge to provide a radial light guide when a light source, such as, for example, LEDs, is employed, such as shown in FIG. 27. Such light source may be located on the proximal surface of a circuit board 809 of the assembly 810 and is positioned to emit light through the opening 813 defined by the light guide ring 812. Confronting surfaces of the ring 812 and proximal wall 802, respectively, may be securely fixed to one another to define the proximal wall assembly of the module housing. In one example, the secure attachment may be by an adhesive, gluing, ultrasonic welding, or the like. In another example, the secure attachment may be a two-sided sticky tape 860. The proximal wall assembly may include a white surface or reflective surface disposed covering the opening 813 for improved radial light transmissivity within the light ring 812 that is emitted through the opening 813. The distal surface of the proximal wall may include the white or reflective surface. In one example, the distal surface 862 of the tape 860 includes the white or reflective surface, and in other examples a disk element with a white or reflective surface may be used. The proximal wall assembly described herein may only refer to the proximal wall without the light ring. Ring 812 may include an attachment element to attach to another module component. For example, ring 812 may include a plurality of retention snap arms 812A depending from a distal surface of ring 812. Arms 812A are configured to permit axial movement of the proximal wall relative to the housing and including tips configured to prevent removal of the ring 812 to a certain position. A button gasket 811 having a ring shape is shown engaging the distal surface of ring 812 and is disposed radially outward relative to the arms 812A. FIG. 47 depicts an exploded view of one embodiment of the module, such as module 800, separated into its individual components along a common axis.

Module may include a first spacer element 815 having a ring shape and defining an inner radial surface 817 disposed along the circumference defined by the snap arms 812A. Surface 817 configured to allow controlled axial movement of the proximal wall assembly from the proximal position to the distal position for wake-up capability. The distal surface of spacer element 815 along the inner radial surface 817 provides an area for the snap arms 812A to engage for retention as the proximal wall assembly returns to the proximal positon under the biasing force. In some embodiments, the light ring is omitted and the proximal wall includes the snap arms for engagement with the surface 817. Spacer element 815 may include a proximal flange 819A disposed along the radial outward extent of the spacer element. The upper end of flange 819A can provide a physical stop to limit distal movement of the proximal wall 802. Spacer element 815 may include a distal flange 819B disposed along the radial outward extend of the spacer element and recessed radially inward relative to the proximal flange 819A. The recess may be sized to accommodate the thickness of sidewall 804 when the upper end of the sidewall engages the radial outer surface of the distal flange 819B.

Button gasket 811 is disposed axially between the proximal wall 802 and ring 812 and a housing portion in the form of the spacer element 815. In one example, the button gasket 811 is engaged between ring 812, or the proximal wall if there is no ring, and element 815. Gasket 811 is axially compressible from its natural state. The gasket material, such as for example, a cellular urethane form, may be configured to provide compressibility. The material of gasket 811 may also provide sealing from liquid egress, but allowing the ventilation. In other embodiments, the gasket material may provide sealing from liquid and air egress. In its natural state, the gasket 811 may provide a biasing force and support along the outer circumference of the proximal wall assembly to maintain the proximal wall assembly in its extended proximal position. When a user presses down on the proximal wall to use the device, the button gasket 811 may axially compress as the ring/proximal wall unit moves distally relative to the spacer element 815 that is in a fixed position. The gasket 811 may aid in returning the proximal wall assembly to the extended position and provide consistent tactile feedback to the user throughout its movement. Instead of the compressible gasket, a spring with lining or other sealing means may be used.

Module may include a second spacer element 821 disposed distal to the first spacer element 815 in between the element 815 and distal wall 806. Second spacer element 821 has a ring shape. The second spacer element 821 is coupled to the first spacer element 815, such as, for example, each having axially extending features that allow for coupling. Battery 861 is shown disposed between elements 815, 821. A battery retainer element (not shown) can be coupled to the proximal surface of the second space element. A battery support element 864 may be included between the proximal side of the battery and one of the circuit boards of the electronics assembly, and in frictional contact with the battery to inhibit movement of the battery within the module. In one example, the battery support element 864 may include a ring of axially compressible material, such as, closed cell foam. The element 864 may have a cross-sectional area less than the battery's cross-sectional area. Sidewall 804 is shown disposed radially outward relative to the contents of the module and axially extended between the first spacer element 815 and a base ring 823 that is coupled to the distal end of the sidewall 804. Base ring 823 may be optional. Sidewall 804 may include a plurality of distally extending retention snap arms 804A for engaging with correspondingly shaped recesses formed along the interior surface of the base ring 823 in a manner to securely fix the components together. Snap arms 804A may be disposed radially inward from the general outer circumference of the sidewall 804 to define a recess sized to receive the general thickness of the upper end of the base ring 823. A seat 804B may be formed along the interior surface of the sidewall 804, extending farther radially inward of the surface. Seat 804B is configured to receive a distal gasket 825.

Distal gasket 825 has a ring shape and is disposed radially between the interior surface of sidewall 804 and the outer circumference of the distal wall 802, and axially between seat 804B and a seat 827A defined by a radial flange 827 extending from the distal wall 802. In one example, gasket 825 is sealably engaged between sidewall 804 and distal wall 802. Gasket 825 may be made from a gasket material, such as for example, a cellular urethane form, may be configured to provide compressibility.

Although the module 800 is shown with the presence switch omitted, a presence switch system, such as, for example, the system 650 described earlier may be incorporated into the module as can be appreciated by those skilled in the art.

Module 800 is shown including another embodiment of a wake-up switch system, now referred to as wake-up switch system 820. Although wake-up switch system 820 is illustratively shown, it should not be limiting as module 800 can also be provided with the wake-up switch system 620. Similarly, the other modules described herein may include wake-up switch system 820.

Figure 36:
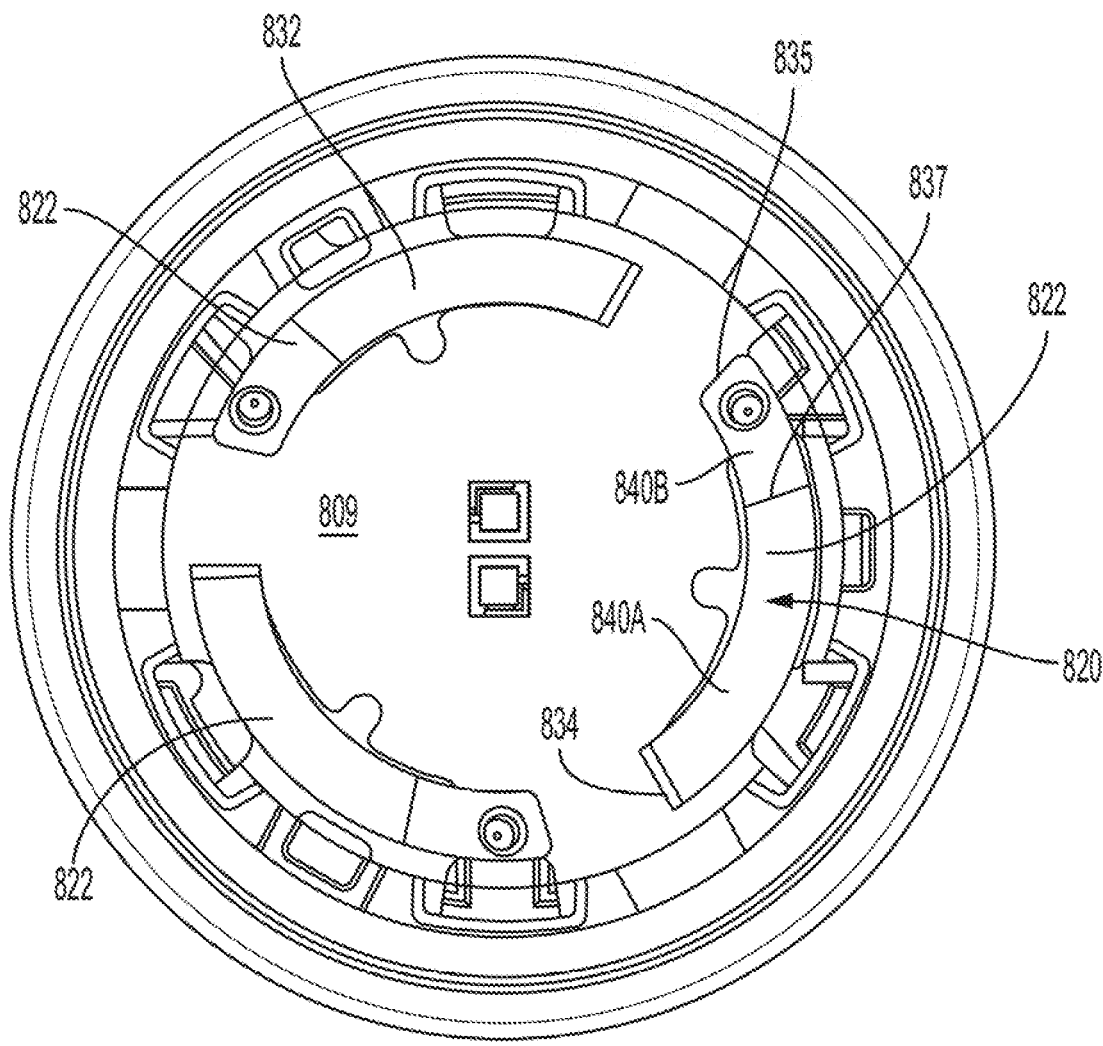
FIG. 36 is a proximal axial view of the module of FIG. 35, shown with the proximal wall assembly removed.

With additional reference to FIG. 36, wake-up switch system 820 includes one or axially moveable contact arms 822 and a corresponding contact pad 824 coupled to the circuit board 809, which can be the flexible printed circuit board (FPCB), of the electronics assembly 810 and in electrical communication with the MCU. Contact arm 822 is able to move distally from a biased, non-contact natural configuration, as shown in the figures, where the contact arm 822 is axially spaced from the contact pad 824 such that there is no electrical communication (thus electronics in a low power state) to a contact configuration by which the contact arm 822 and contact pad 824 are in a contacting relationship such that there is electrical communication between the two (thus increasing power to electronics to the full operation state). Contact arm 822 may have a pre-load to maintain contact with the proximal wall 802 along different axial positions of the movable proximal wall. The biasing may be provided by a discrete spring or the contact arm 822 may have a leaf spring configuration, such as shown.

In one embodiment, the contact arm 822 includes a base 830 fixedly mounted to the circuit board 809, a movable arm length portion 832 coupled to the base 830 via a joint 834. The arm length portion 832 is capable of pivoting motion relative to the base 830 about the joint 834. The biasing force from the contact arm 822 may be sufficient to maintain the upper proximal wall 802 in a proximal first position. When a user distally actuates the proximal wall 802, the axial force is sufficient to overcome the biasing force of the contact arm 822 and allow for the distal movement of the proximal wall 802 away from its first position to a distal second potion where the contacting arm 822 and contact pad 824 are in contact for activation of the switch system and/or wake-up of the control system. Movement of the proximal wall 802 may occur relative to the module housing that is in a fixed position during this action to power-on the system without an actuation force on the actuator. Movement of the proximal wall 802 may also occur relative to the module housing that is in the process of moving to a final distal position during the actuation force on the actuator to cause dose delivery. The switch system 820 may include alternative switch configurations, such as, for example, a mechanical switch or rubber dome switch.

Contact length arm portion 832 may extend from the base 830 at an acute angle relative to a plan defined by the base 830, although the angle of extension of the arm portion may be orthogonal or acute relative to the base. From a radial view perspective, the contact arm may have a V-shaped body. In one example, any part of the arm portion 832 may include a contacting portion contactable with the contact pad 824. In one embodiment shown, the tip end 835 of the arm portion 832 defines the contacting portion. In another embodiment, the contacting portion is along the intermediate body of the arm portion 832. The contacting portion of the arm portion 832 may be configured for enhanced contacting the contact pad 824, such as, for example, including a polished or smoothed surface and/or a rounded surface or hook shape and/or a domed surface (such as shown in FIGS. 35-36).

Any application force with the proximal wall 802 may move the contact arm from its natural state, to its contact configuration. In one embodiment, the arm portion 832 may be angled along its body at a bearing joint 837 to define a proximal extending first portion 840A and a distally extending second portion 840B. The first portion 840A extends between the base 830 and joint 834 portion and the bearing joint 837. The second portion 840B extends between the bearing joint 837 and the tip end 835. The length and angle of extension of first portion 840A is configured to place the bearing joint 837 at a location to maintain contact with the interior surface 802A of the proximal wall or the light ring, or alternatively corresponding bosses 802B extending distally from surface 802A, of the proximal upper wall 802 when moving between its first and second positions. The length and angle of extension of second portion 840B in the distal direction is configured to place the tip end 835 in a spaced relationship with the contact pad 824 when the proximal wall 802 is at the first position, and to allow distal movement of the tip end 835, together with the proximal wall 802, for a sufficient distance to contact the contact pad 824 when the proximal wall 802 is at the second position. In an alternative embodiment, the bearing portion 837 of the contact arm 822 may be located in closer proximity to the tip end 835 of the arm portion than the location of the contacting portion. To this end, the contacting portion may be formed along a valley or recess of the arm portion. In some contact arm embodiments, the bearing portion of the contact arm is disposed in a more proximal location than the contacting portion.

From an axial view perspective, the configuration of the arm portion 832 of contact arm 822 may be linear, angular, or curved. FIG. 36 illustrates an example of the arm portion 832 having an arcuate shape. Although one contact arm and contact pad system may be sufficient for wake-up functionality of a module, FIG. 36 depicts the system including three sets of contact arms 822 and contact pads (not clearly shown in the figure). As shown, the three contact arms 822 may be disposed radially from the longitudinal axis about the same distance. The arms 822 may be disposed circumferentially spaced from one another at equal distance, such as, for example, allowing for 20 to 40 degrees of separation between adjacent ends of the contact arms. Multiple sets, such as, two, three, four, five, or more, may distribute the biasing force from the contact arms 822 to the upper wall 802 more evenly. Even with multiple sets, the controls may be configured to require one only set of contact arm 822 and contact pad 824 or less than all of the total number sets to make contact for activation. Requiring less than the total amount of contacts for activation can allow the user to press any portion of the proximal wall to cause wake-up, rather than requiring the user accurate finger placement. To aid inadvertent activation, the controls may be configured to require more than one set, such as, for example, all three sets, of contact arms 822 and contact pads 824 to make contact for activation.

The base 830 and contact arm portion 832 may be formed integrally from the same material, such as, an electrically conductive material, such as metal. The contact pad 824 is made of material conductive with the contact arm. The base and arm portion may be formed separately from same materials or different materials. If formed separately, the base and arm portion may be coupled to one another, such as, for example, welding, metal welding epoxy, brazing, or other means depending on the materials of the components. The base and arm portion may be formed from a plastic material having conductive material impregnating the plastic material in at least the tip end portion or having a conductive material coating along the tip end. In one example, the base and arm portion is formed integrally from an electrically conductive metallic material and are coupled to one another at a living hinge joint such that the contact arm has a leaf spring configuration.

FIG. 37 shows another example of a module attachment subassembly, now referenced as spacer unit 839. Unit 839 is configured, when part of a module, to permit the module 800 to be removably coupled to any of the dose buttons described herein via the attachment element 807. Distal wall 806 includes the aperture 836 defined therein for receiving a light guide member 849 for the identification sensor, such as, for example, identification sensor 680 in FIG. 29. Vent opening 841 may be defined in the distal wall 806. Sensor receiving recessed locations 842 are defined in the proximal surface of the distal wall 806 for equi-radially-spaced, and equi-angularly, placement of measurement sensors, e.g., for five magnetic, inductive, or capactive sensing elements or magnetic sensors 906 as disclosed herein. Recesses 842 may be located in the distal surface of distal wall 806. Attachment stakes 843 may be provided for coupling distal wall 806 and/or unit 839 to a complementary attachment feature of the module housing.

Figure 39:
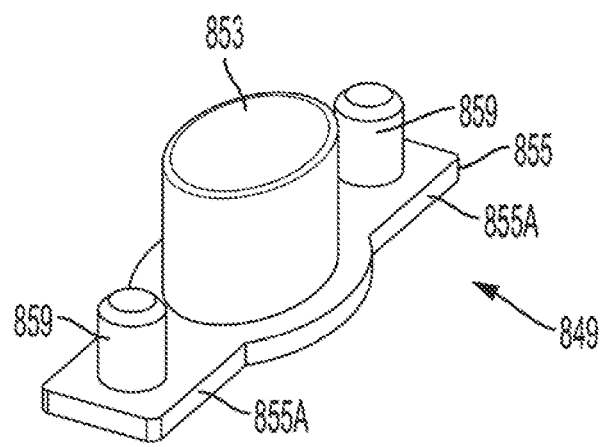
FIG. 39 is a perspective view a light guide member component provided in the module of FIG. 35.
Figure 38:
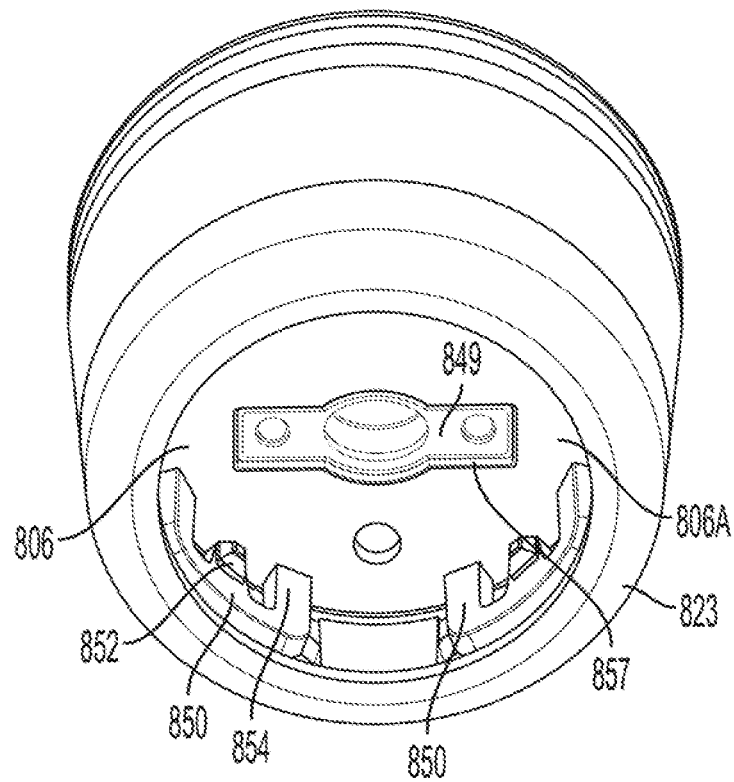
FIG. 38 is a perspective distal partial view of the module in FIG. 35, shown with the delivery device omitted.

With reference to FIG. 39, light guide member 849 is shown with a light guide post 853 extending from a base 855. The light guide member being made of a material, such as an optically clear polycarbonate, that permits at least some light transmission therethrough for the identification sensor to emit and sense light reflected from the colored portion of the proximal surface of the button. The post 853 is sized to fit within the aperture 836. Shown in FIG. 38, a recessed region 857 defined in the distal surface 806A of the distal wall 806 may surround the aperture 836. The recessed region 857 may have a depth and shape to correspond to the thickness and shape of the base 855. The aperture 836 and the recessed region 857 may be sized and shaped to receive the light guide member 849 in a secured manner. The axial length of extension can provide a light guide path for the identification sensor from the distal surface of the distal wall 806 that will abut against the colored surface feature of the device button proximally to directly contact the sensor, or there may be an axially spaced gap, as shown, between the end of the post 853 and light color sensor. The light guide post 853 has a cross-sectional shape of any one of a variety of geometric shapes, such as circular, elliptical, or rectangular. In one example, the post 853 has an elliptical cross-sectional shape. One or more attachment posts 859 (two shown) may also proximally extend from the base 855. Each attachment post 859 may be spaced radially from the light guide post 853. To this end, the base 855 may include wing portions 855A to accommodate the attachment post. A corresponding number of post apertures 863 may be defined in the distal wall 806 to receive the attachment posts 859 during manufacturing. Once received therein, the attachment posts may be heated, such as for example, through ultrasonic welding, to allow material to fill voids the respective post apertures for a secure attachment to enhance consistent sensing capability.

Module 800 includes another embodiment of the attachment element 807. Although the attachment element 807 is illustratively shown, it should not be limiting as module 800 can also be provided with the attachment unit 500 or attachment element 419. Similarly, the other modules described herein may include the attachment element 807.

Attachment element 807 with the distal wall 806 may form a unit part of the module 800. Attachment element 807 may include a plurality of distally extending arms 850. In an exemplary embodiment, arms 850 are equi-angularly spaced around the dose button. Arms 850 are depicted as being coupled to and depending distally from the distal wall 806. When module is attached to the device, arms 850 are positioned to contact the radially outward facing surface of the dose button. Arms 850 include an axial extending body 854. Body 854 may include a protruding bearing portion 852 extending radially-inward of the body 854. Body 854 of arms 850 may include a W-shaped body, where outer distally extending legs 856A-B of arm body extends from the distal wall 806 at two attachment locations and the proximal extending inner arm 858 includes the protruding body 852. Surfaces of the protruding body of bearing portion 852 may be orthogonal, curved and/or angled. Body 854 may, alternatively, include a J-shape having a portion that defines the proximally extending arm.

With additional reference to FIG. 35, battery 861 may provide shielding properties for the magnetic sensors and magnetic ring. In one example, the battery 861 may be a coin cell battery with a ferromagnetic nickel coating. Placement of the battery 861 may be axially proximal to the magnetic sensors to provide shielding for the sensors, providing shielding along its proximal side to inhibit magnetic field influences from the proximal direction, and/or providing shielding along its distal side deflecting the magnetic flux from the magnetic ring toward the sensors. In one example, battery 861 may assist in re-directing the magnetic flux lines, such as, from the ring, such as the rotation sensed element 706, toward the position of sensors, such as sensors 906, and in re-directing the magnetic flux lines from unwanted external interference away from sensor position. In this example, the size of the battery, such as the radius, may coincide with the radial location of the sensors from the axis. In another example, the make-up of battery 861 may provide other shielding properties, such as the battery including iron (most series), cobalt or other nickel alloys with appropriate thicknesses. The battery 861 can have a cross-sectional area size relative to the radial placement of the magnetic sensors and/or can be axially spaced from the magnetic sensors to provide such shielding.

Any of the modules described herein, such as, for example, module 800, can comprise five (shown) or six sensing elements, such as magnetic sensors. The sensing elements may be disposed within the module compartment 808 and coupled to the circuit board 809 of the electronics assembly 810 and thus to the MCU. In one example, the sensing elements comprises five or six magnetic sensors disposed within corresponding sensor receiving recessed locations 842 defined within the distal wall 806, as shown in FIG. 37, although the sensing elements may be disposed on top of the distal wall 806 (that is, not in recesses), or more proximal to the distal wall 806 within the compartment of the module.

Figure 40:
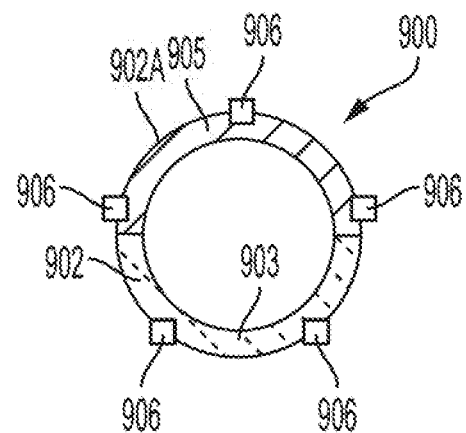
FIG. 40 is an axial view of yet other exemplary embodiment of the dose delivery detection system utilizing magnetic sensing.
Figure 41:
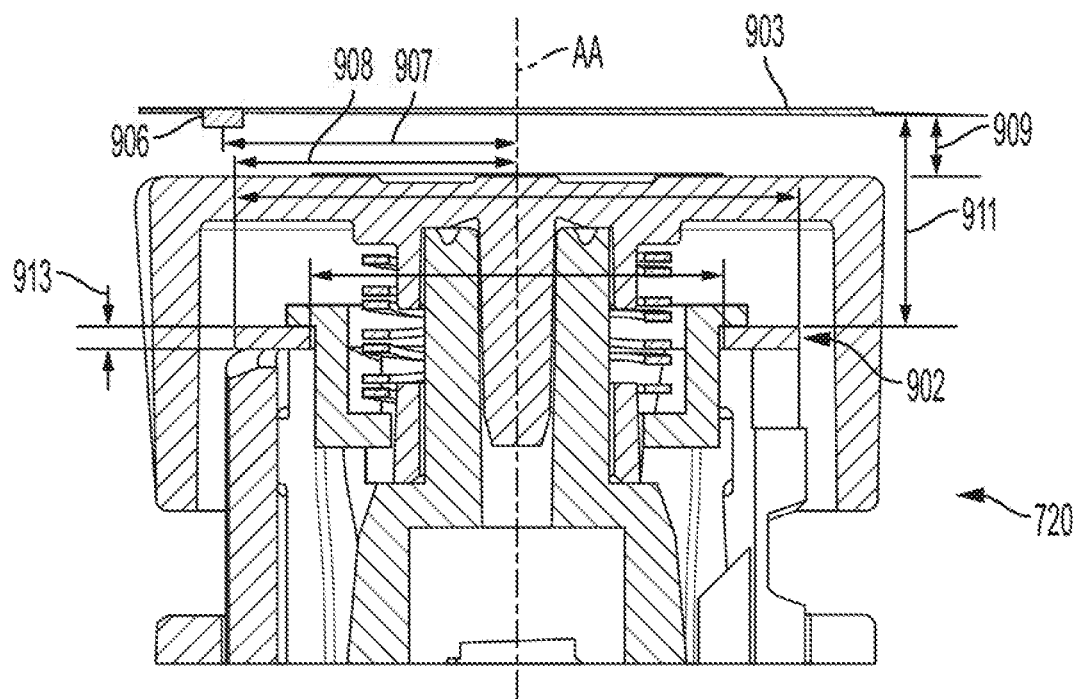
FIG. 41 is a cross-sectional view of the proximal portion of the medication delivery device and its relative position to the magnetic sensing system.

FIGS. 40-41 depict an example of an arrangement of the sensors relative to the magnetic ring, and is illustrative for all other magnetic dose detection systems described herein. FIG. 40 illustrates another example of the magnetic sensor system, now referred to as system 900, including as the sensed element the diametrically magnetized ring 902 having the north pole 903 and the south pole 905. Magnetized ring 902 is attached to the dose setting member, such as, for example the flange, as previously described. The radial placement of the magnetic sensors 906, such as, for example, hall-effect sensors, relative to the magnetized ring 902, can be in an equi-angularly relative to one another in a ring pattern. In one example, the magnetic sensors 906 are disposed radially in an overlapping relationship with the outer circumferential edge 902A of the magnetized ring 902 such that a portion of the magnetic sensor 906 resides over the magnetized ring 902 and the remaining portion resides outside the magnetized ring 902, such as shown in FIG. 40. The overlapping arrangement was found to place the sensors in the range for high flux capability and thus for more consistent magnetic flux sensing. FIG. 41 shows the radial distance 907 determined from the center of the magnetic sensor 906 to the axis AA. The radial distance 907 may be sized to be at least the outer radius 908 of the magnetized ring 902. In one example, the radial distance 907 is 0.1-20% greater than the outer radius of the magnetized ring 902, and in another example, the radial distance 907 is at least 10% greater than the outer radius of the magnetized ring 902. It has been surprising that this position can provide enhanced peak magnetic flux for sensing over other radial positions.

FIG. 11A depicts another example of the relevant radial placement with the magnetic sensors disposed entirely over the ring. FIG. 11B depicts another example of the relevant radial placement with the magnetic sensors disposed entirely inside opening formed by the ring.

FIG. 41 illustrates an example of an axial placement and a radial placement of the magnetic sensors 906 relative to magnetized ring 902. Sensors 906 may be disposed along the circuit board 903 of the electronics assembly of the module (module components omitted for clarity) that is disposed along a common plane that is substantially orthogonal to the axis AA. Magnetic ring 902 of a thickness 913 may be disposed in a planar positon, parallel to the plane of the sensors 906. Ring 902 may be disposed in the device 720 arrangement, while the sensor 906 may be disposed in the module that is removably attachable to the device. In an alternative example, the components of the module, including the sensors 906, may be permanently integrated with the device with magnetized ring 902 like what is shown in FIG. 12.

Geometry of the ring can be modified within available space constraints to meet the magnetic flux performance requirements for the selected sensors. FIG. 41 depicts the relative axial position 911 of the magnetic sensors 906 over the magnetized ring 902 when the dose button is uncompressed, such as during dose setting. During dose delivery, the relative axial position of the magnetic sensors 906 over the magnetized ring 902 changes after distal displacement of the dose button and sensors 906 by a distance, shown by arrow 909, toward the rotating magnetized ring 902 that remains axially stationary. The amount of distal movement the magnetic sensors 906 can be in the range of 1 mm to 3 mm relative to the magnetized ring 902. In one example, during use, as the user applies pressure on the top of the module, the button/spring sub-assembly undergoes axial compression, and reduces the relative axial distance between sensor 906 and magnetized ring 902 by an axial distance of 1.7 mm. At the dose delivery position, the magnetic flux of magnetized ring 902 available for reading by the sensors 906 is at least twice the value than when the sensors 906 are in the dose setting position.

Magnet material for diametrically magnetized ring 902 should be selected such that flux available at the dialing and dosing distances will be acceptable for reliable sensing. In one example, the magnetic ring use for the sensed component, for example, may be made from sintered Neodymium N35 grade material with nickel coating. A neodymium magnet (also known as NdFeB or NIB or Neo magnet) is a rare-earth permanent magnet made from the alloy of neodymium, iron and boron. Other sintered Neodymium magnet grades such as N42, N45, N50 and alike or bonded Neodymium grade (injection or compression molded with thermoplastic or thermoset) may be considered for the appropriate flux availability at the magnetic sensors. The selected magnet material is expected to meet mechanical strength requirement for firmly fitting against the plastic carrier, such as carrier 708, and sized to sustain operational and handing impacts without cracks or failure. The secured magnetized ring is secured fixedly to the dose setting member to not rotate by itself, but does rotate with the dose setting member during dialing or dosing.

The axial movement of the sensors relative to the magnetized ring during dose delivery and the change in the magnetic flux due to this axial position change and due to rotation of the ring can make dose detection accuracy challenging. Also, more cost-effective diametrically magnetized rings of sintered N35 Neo magnet can provide non-uniform magnetic field properties, leading to greater inconsistent sensing detection and dial error. The dial error of the module for dose detection is the rotational position difference in degrees between the actual physical rotational position of the device dose components, such as the magnetic ring, ("the dialed position"), and the sensed rotational position detected by the magnetic sensor system ("the detected position"). For example, when a user desires a certain number of units of drug to be delivered from the device, the user rotates the device button with the module attached thereto relative to the device housing by an amount as indicated by the dosing dial, such as 10 units or approximately 180 degrees of rotation based on 18 degrees±X % per 1 unit. When the button is pressed to begin the deliver operation, the dose detection system can track the initial position and the final position at the completion of the dose delivery, in which the difference between initial and final positions corresponds to a number of degrees of rotation and correlated amount of dose units delivered.

Dial error may be illustrated with the following example. The dialed initial position may place the dose/dialed member of the device, and thus the magnetic ring, at a nominal zero initial physical position after dose setting has occurred, and a delivered final physical position of the ring after rotation of 90 actual degrees, correlating to five units during dose delivery. With dial errors, the dose detection system in a four-sensor system with regular production diametrically magnetized rings may detect −10 degrees for the nominal zero initial positon of the ring, and 100 degrees for the delivered final position, resulting in a total of 110 degrees of detected rotation of the ring. This would correspond to a sensed dose of over six units delivered, which is greater than the five units actually delivered.

Dial errors can be introduced to the system from the magnetic sensors and other factors. The first spatial harmonic waveform (main waveform/signal) can be susceptible to phase, gain or offset errors during rotation of magnetized ring relative to the sensors that measure a sine wave, with the number of sensors equally spaced around a circumference from one another and equally axially spaced from the magnet would represent the number of times the sine wave is sampled. Appropriate calibration of sensors may reduce these errors significantly. However, other error contributions can be from higher harmonics such as third or fourth harmonics to the first harmonic. Some error can be reduced by consistent radial positioning of the magnet sensors from module axis, as well as consistent circumferential spacing between each of the sensors, reducing tilt of plane of co-located sensors to be substantially normal to module axis and in parallel to the magnetic ring, and calibration of the system.

Improving the uniformity of the flux in magnetic properties of the diametrically magnetized rings by using higher-grade magnetic material sources, such as, for example, N50 grade Neodymium magnet, or tighter manufacturing controls, may reduce the dial error. Such improved magnetic components would be more expensive and limit the magnet sourcing capability. In addition, there was uncertainty as to whether providing additional magnet sensors (one or two more) that already showed non-uniform properties would improve the sensing capability. It has been discovered that that the use of five or six magnet sensors 906 for the rotating diametrically magnetized ring 902 during dose delivery improved the position signals used for dose determination by proper filtering of offset second and third order harmonic signal distortion normally present in regular production magnets, which led to the reduction of dial error. Such filtering was not present with the 4-sensor architecture. To this end, improvement have been discovered to ensure that the amount of units delivered detected by the dose detection system corresponds to the actual amount of units delivered.

Figure 42:
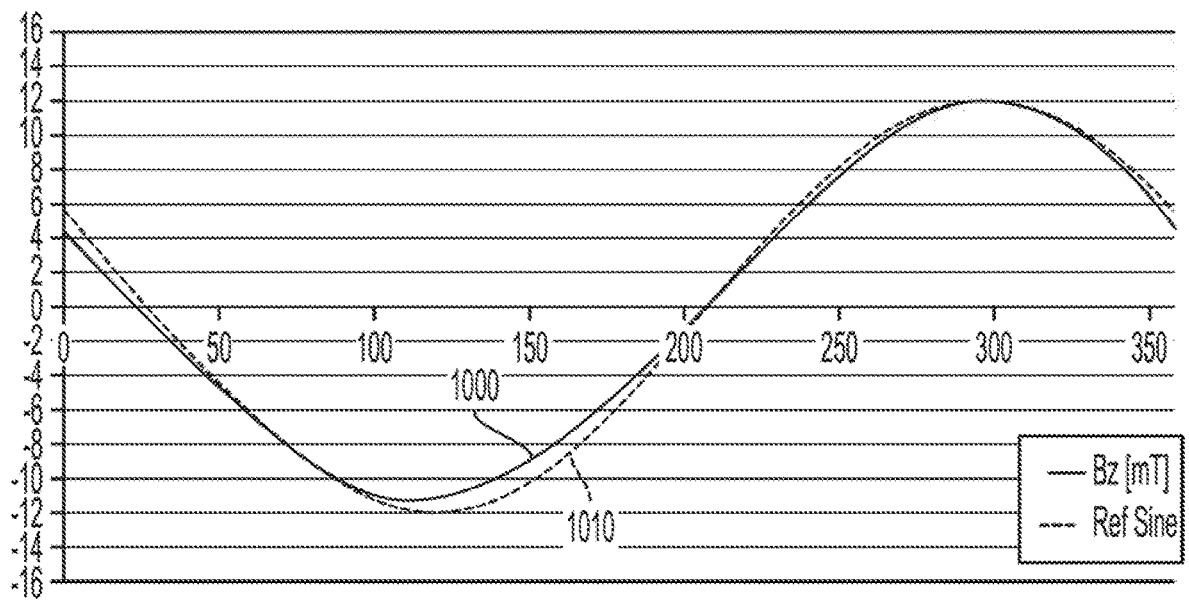
FIG. 42 is a graph comparing a measured rotational magnetic flux waveform with a purely sinusoidal model of the magnetic flux waveform during rotational position sensing.
Figure 43:
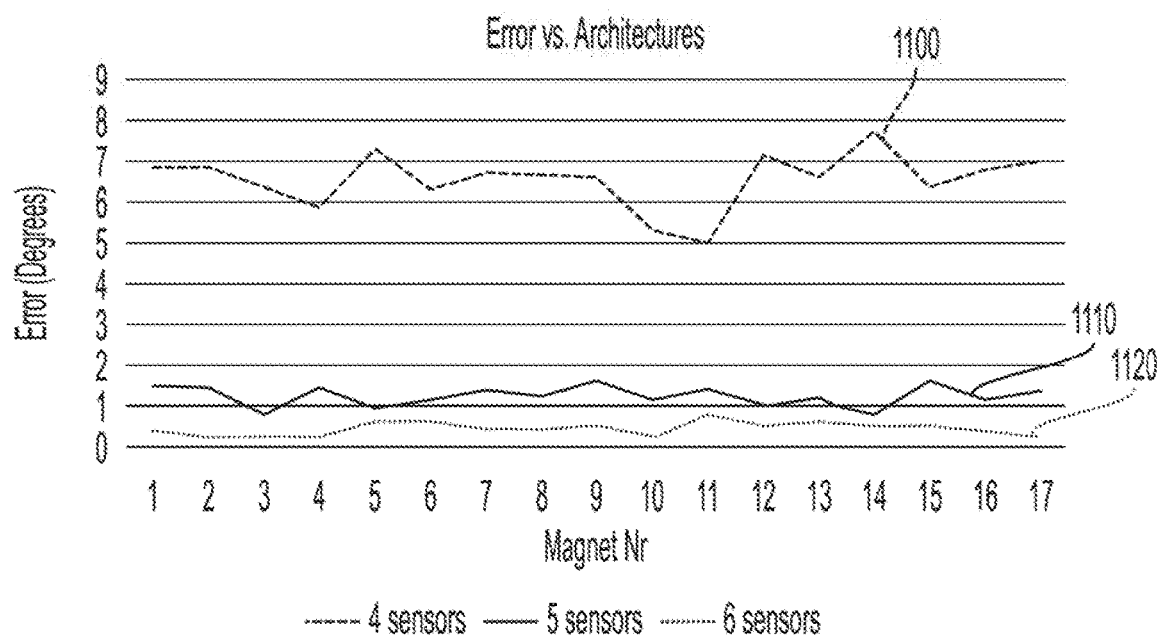
FIG. 43 is a graph comparing the results of dial/dose errors contributed from magnetic non-uniformity and harmonic distortions from a sample number of N35 grade magnets made from regular production means for 4-, 5- and 6-sensor architectures.
Figure 44:
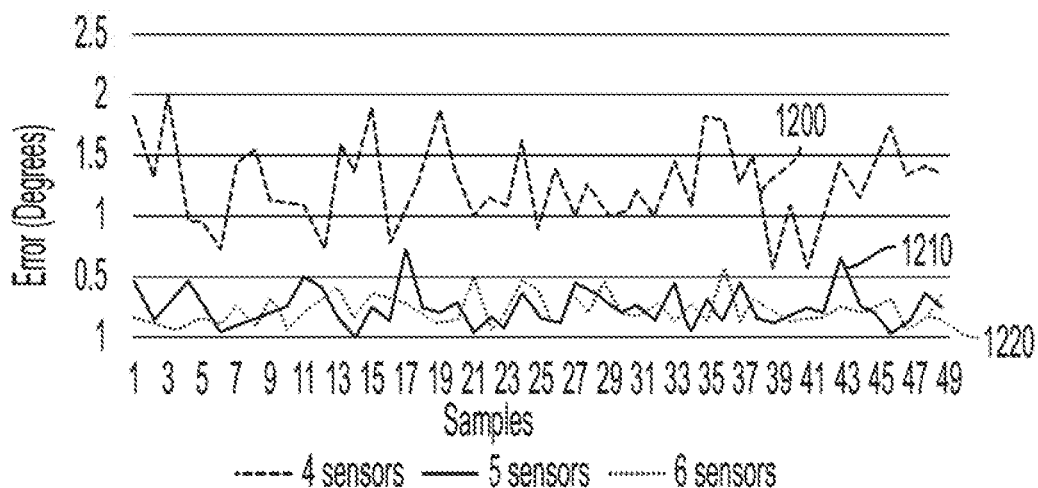
FIG. 44 is a graph comparing the results of dial/dose errors contributed from magnetic non-uniformity and harmonic distortions from a sample number of N35 high-grade magnets made from customized production for 4-, 5- and 6-sensor architectures.
Figure 45:
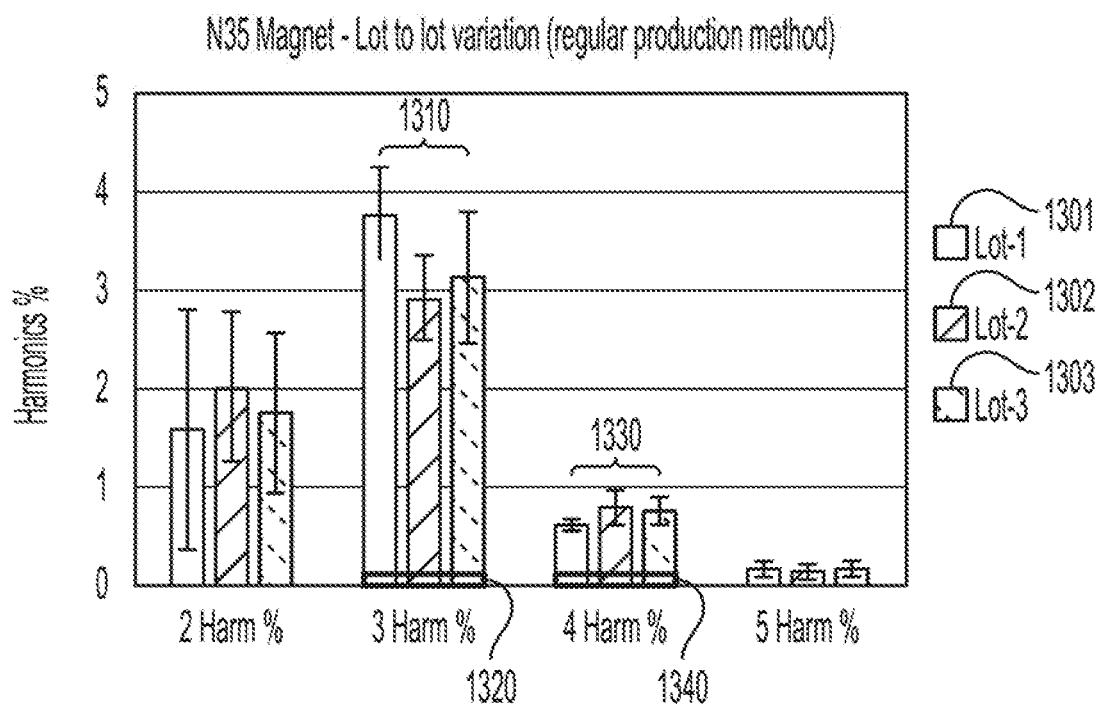
FIG. 45 is a graph depicting different orders of percentage of harmonics for lot-to-lot variation of N35 grade magnets made from regular production means.

Regular production N35 Neo sintered diametrically magnetized rings were tested to determine harmonic distortion of sensor signals for second, third, fourth and fifth order harmonics percentage amplitude vs. first order harmonics. Results are shown in FIG. 42. A customized magnetic test fixture was built to emulate the magnet-sensor sub-system function arranged in the modules described herein. The fixture is configured to adjust relative radial and circumferential position and axial (tilt out of plane) positions of the sensors and magnetic rings to not only test different configuration, but also reproduce the axial and radial arrangement in FIG. 40 and FIG. 41. Results from individual sensors can be analyzed to understand the effects of magnetic non-uniformity on harmonic distortions and dial/dose errors. Dial errors resulting from 4- vs. 5- and 6-sensor architectures for N35 grade magnets made from regular production (more cost effective) and customized production (less cost effective) methods are shown in FIGS. 43-44, respectively. FIG. 45 illustrates the sensitivity of 4-sensor architecture with regular production N35 Neo sintered diametrically magnetized rings to third harmonics, leading to its susceptibility to the increase of dial errors to over six degrees, and the immunity of 5-sensor architecture with regular production N35 Neo sintered diametrically magnetized rings to third harmonics, leading to a substantial reduction to dial errors to less than two degrees.

FIG. 42 depicts the dial error of a 4-sensor architecture used with regular production N35 magnetic rings. The 4-sensor architecture has been demonstrated to exhibit increased undesirable error contributions from third harmonics affecting the reliability of the position signals. It was thought that the radially equidistant sensor configuration would be immune to small amplitude variations from the magnetic flux of the rotating magnetized ring. Numerical simulation of the 4- vs 5- and 6-sensor architecture considering Neodymium magnet flux properties showed that the addition of sensors equally spaced along the circumference reduced higher order harmonics on angle measurements, thereby reducing the dialing and dosing error variations. Various tests with sintered N35 Neo magnets from regular production (ones originally showing non-uniform properties), sintered N35 magnets with customized production methods (w/tighter controls), and sintered N50 Neo higher grade magnets were performed to compare the sensor architecture effects with each other and to numerical modeling simulations, where it was found that third harmonics had the most influence on angle measurements. To this end, five sensor architecture was able to cancel up to the third harmonic distortion better than the four sensor architecture, while it is possible to cancel up to fourth harmonics with the six sensor architecture.

In FIG. 42, the effect of the error contributions from higher order harmonics that lead to deviation of the measured rotational magnetic flux waveform during rotational position sensing along 360 degrees (at line 1000) for a four-sensor architecture as compared to a calculated mathematic desired model of the magnetic flux waveform during rotational position sensing (at line 1010) based on magnet geometry and its properties. Such deviation between the two lines 1000, 1010 may contribute to dial errors in four-sensor systems.

From test data, the module with five or six magnetic sensors is configured to have significantly reduce the distortion error in a manner that it is likely to produce a dial error contribution from the magnet distortion from the sensor/ring arrangement that would be two degrees or less. In one example, in FIG. 43, for a lot of regular production magnets, the dial error for a 4-sensor architecture was an average of 6.5 degrees (at line 1100). The dial error for 5-sensor architecture with similar regular production magnets was an average of 1.2 degrees (at line 1110), respectively, and further an average of 0.5 degrees with a 6-sensor architecture (at line 1120). Five-sensor or 6-sensor architecture with regular production N35 magnetic rings is shown to have reduced the dial error by over five times compared to the 4-sensor architecture. Five-sensor or 6-sensor architecture with custom production magnets is shown to have reduced the error by over three times compared to the 4-sensor architecture. In FIG. 44, for customized production magnets, the dial error reduced from average of 1.4 degrees to an average of 0.4 degrees from 4-sensor (at line 1200) to 5-sensor architecture (at line 1210), respectively, and to an average of 0.4 degrees with a 6-sensor architecture (at line 1220).

FIG. 45 summarizes percentage harmonics variation from three lots (1301, 1302, 1303) of N35 grade sintered magnetic rings produced by regular production method for 4-sensor and 5-sensor systems. The 4-sensor architecture (at line 1310) exhibited up to an average of 3.8 percent third harmonics, while the 5-sensor architecture (at line 1320) exhibited an approximately zero percent at the third harmonics. The 5-sensor architecture (at line 1320) exhibited up to an average of 0.8 percent fourth harmonics, while the 4-sensor architecture (at line 1340) was exhibited an approximately zero percent at the fourth harmonics. The contribution of third harmonics to the main waveform is what resulted in the dial error in the 4-sensor architecture to over six degrees, as shown in FIG. 43, while the improvement to the main waveform with the reduction of third harmonics with the addition of sensors to 5-sensor or 6-sensor architecture, resulting in a reduced dial error below two degrees as shown in FIG. 43.

Figure 30:
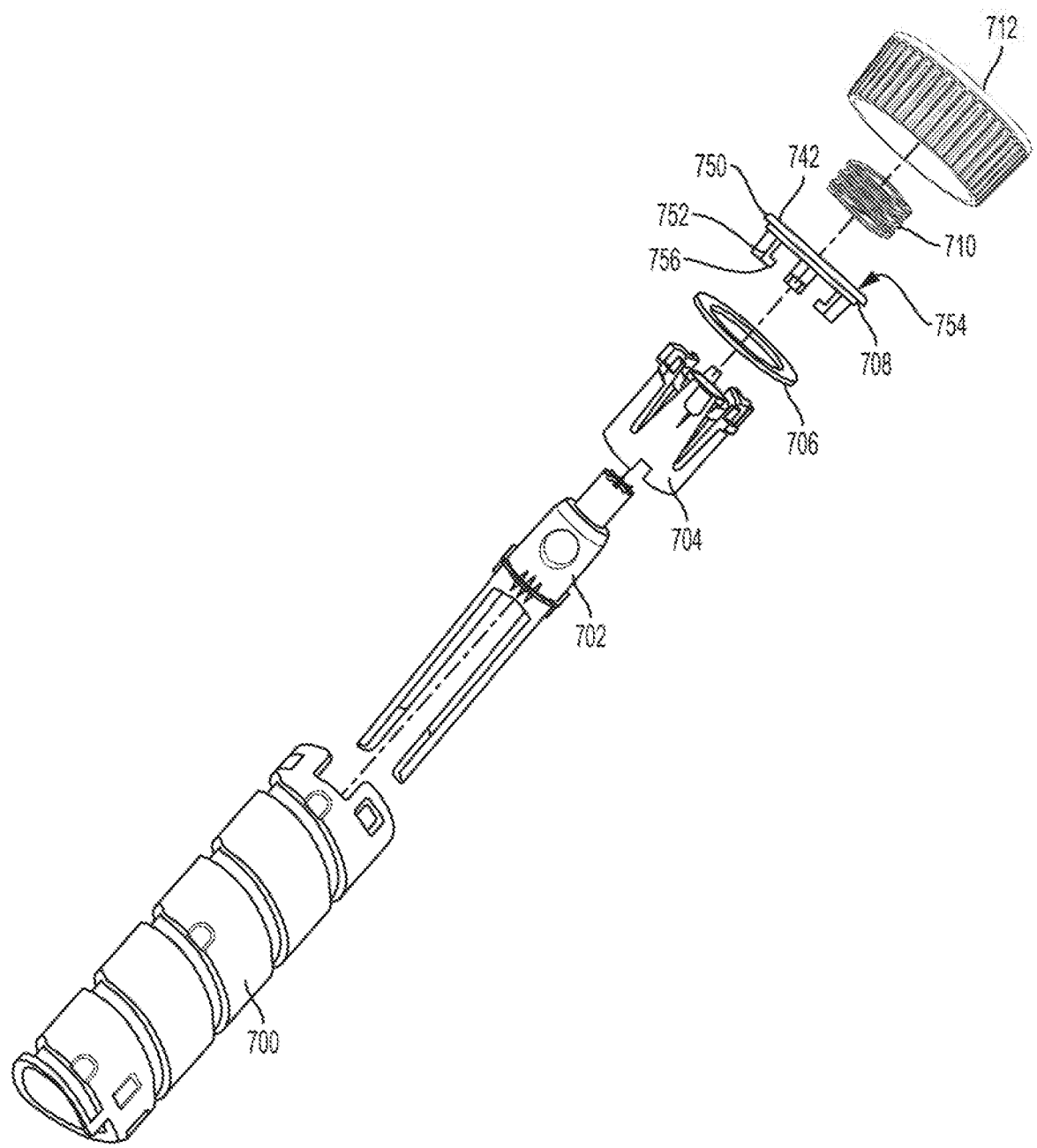
FIG. 30 is a perspective piece part exploded view of a subassembly of a proximal portion of a medication delivery device.

Further illustrative embodiments of a dose delivery detection system are provided in FIGS. 30-34. The embodiments are shown in somewhat diagrammatic fashion, as common details have already been provided with respect to FIGS. 1-5. Described herein are several exemplary embodiments of medication delivery devices utilizing magnetic sensing of dose delivery. The ring-shaped element, such as, for example, magnet or metal ring, may be fixedly secured to the dose dial member and/or flange of a device by various attachment means, such as adhesives, welding, or mechanical attachments. For high volume manufacturing, the attachment means may be beneficial. In FIGS. 30-34 there is shown an illustrative manner of mounting a ring-shaped element to a flange forming a part of a medication delivery device. FIG. 30 illustrates the components in axial alignment that are coupled to one another as an integral single unit (as shown in FIG. 31) which rotates and axial moves as a single unit, including: the dial member 700, an exemplary clutch 702, a dose setting component, such as, for example, flange 704, to receive a rotation sensed element 706, a carrier 708 to fixedly couple the rotation sensed element 706 to the flange 704, a button spring 710 for biasing a dose button 712. Instead of the flange, other dose setting components described herein may be used. Dose button 712 may have the configuration of any of the buttons described herein. Referring to FIG. 31 and as previously described with respect to FIGS. 1-4, medication delivery device 720 includes dial member 700 mounted within device body 722. Flange 704 is received within dose dial member 700, and clutch 702 is positioned within flange 704. Dose dial member 700, flange 704 are rotationally fixed together and rotate during dose setting and/or dose delivery in direct relation to the amount of a set or delivered dose. Clutch 702 includes stem 724 to which is mounted dose button 712. Spring 710 acts between dose button 712 and flange 704 to bias dose button 712 proximally away from flange 704. As previously described, the medication delivery device is further provided with a rotation sensed element attached to the flange such as the sensor is housed entirely within the dose button. Any of the modules described herein includes the electronics assembly and the sensing elements to detect rotation of the rotation sensed element 706 during dose setting and/or delivery to determine the amount of dose involved.

Flange 704 is generally cylindrical in shape and defines a proximal axial surface 732 at the end of sidewall 734. Flange 704 further defines a central opening 736 that is interior of proximal surface 732. As shown in FIG. 32, the rotational sensor 706 has an annular shape, such as an annular magnet, metal ring, or magnetized or metalized polymer ring, is positioned on proximal surface 732 of flange 704. Carrier 708 includes an overlapping proximal lip or support 742 which is positioned against the proximal surface of the rotational sensor 706 opposite proximal surface 732 to sandwich the sensor 706 therebetweeen. Support 742 is shown as a generally ring-shaped component, however it may alternatively comprise a segmented ring or a plurality of supports spaced about rotational sensor 706.

In this configuration, carrier 708 retains sensor 706 in position on top of flange 704 by having support 742 bear distally against sensor 706. This is accomplished by having carrier 708 fixed axially relative to flange 704. In one embodiment, carrier 708 is attached directly to flange 704, for example at a location distal of sensor 706. In another illustrative embodiment, carrier 704 is spring-biased in a distal direction, such as by spring 710 urging carrier 708 away from dose button 712, or by a spring acting to pull carrier 704 toward flange 704.

Figure 34:
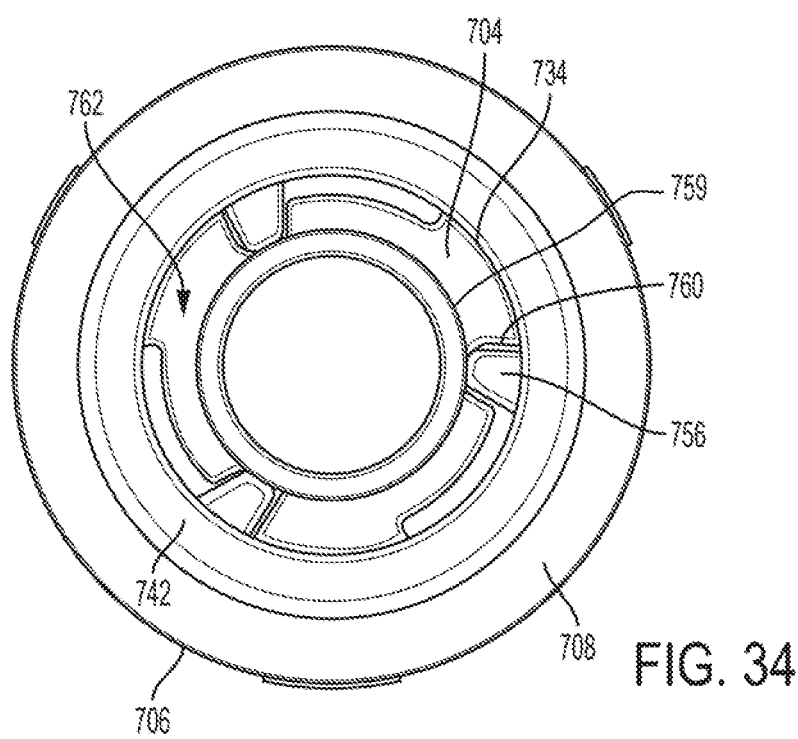
FIG. 34 is a proximal view of the flange, the carrier, and the rotation sensed element assembled.

Referring back to FIG. 30, carrier 708 includes a tubular body 750 with a plurality of axially extending legs 752 circumferentially spaced from one another about a generally axial bore 754 that extends through the carrier. Body 750 includes support 742 sized to capture the rotation sensed element 706 against the flange. Body 750 is sized to receive the inner diameter or cross-sectional area of the sensor 706. As shown in FIG. 31, the support 742 extends radially outward beyond the size of the body 750. The portions of the body 750 with the legs 772 depending therefrom may include a snap radial lip 771 positioned distal away from the support 742 to the size of the axial thickness of the sensor 706 to engage the distal surface of the sensor 706. Each of the legs 772 includes a radially inward protruding element 756 sized and shaped for insertion within corresponding suitably sized axial slots 760 formed in the sidewall 734 of the flange, as illustrated in FIG. 34. Slots may be sized to snugly receive the element 756 such that through frictional engagement the two component are rotationally locked and torque is transmitted therebetween.

The radial ends of the element 756 may be in engagement with a central hub of the flange 704 as shown in FIG. 31 and FIG. 33. As shown in FIG. 31, in one approach, legs 752 of carrier 708 define a circumferential cross-sectional span sized for secure frictional engagement along the cylindrical interior surface 759 of the flange 704 when inserted within the opening 736 of flange 704. In one example, legs 752 extend within central opening 736, and in one approach are directly attached to flange 704 at a location distal of sensor 706. The relevant placement of the spring 710 is shown in FIGS. 31 and 33. Flange 704 may include a radial slot 762 formed in its proximal axial surface 732. Slots 760 are formed in the flange in a manner such that the interior surface of the legs 752 are in close alignment with the interior surface of the outer wall that defines the radial slot 762, as shown in FIG. 31. In this configuration, the distal end of spring 710 is positioned to within the radial slot 762. The walls defining the radial slot 762 support the distal end of spring 710 and allows bearing against the dose button at the mounting collar, thereby urging carrier 708 in a distal direction away from the dose button.

The various components of carrier 708 may comprise either partial or full circumferential members. For example, the body of the carrier 708 may extend fully around the flange, or may be formed as spaced segments. Advantageously, use of the carrier means that rotation sensed element is held firmly in place without the use of adhesives. Although adhesives may be used, adhesives can complicate the fabrication process.

Electronics assembly 610 includes a variety of operably connected components for module 600 as well as any of the other modules described herein, including a battery 621 for power source and associated contacts, MCU for executing programmed instructions, memory for storing programs and data, a communications assembly for transmitting and/or receiving data, timer for tracking time, and various switches and sensors as described. Any of the modules described herein, such as, for example, modules 82, 232, 400, or 600, may be configured to house any of the electronics assemblies described herein, including being configured to house the sensing elements 160 for use with the sensor system 150 described previously.

FIG. 46 illustrates an example of the electronics assembly, referred to as 1400, which can be included in any of the modules described herein. MCU is programmed to achieve the electronic features of the module. MCU includes control logic operative to perform the operations described herein, including obtaining data used for determining a dose delivered by medication delivery device based on a detected rotation of the dose delivery member relative to the actuator. MCU may be operable to obtain data by determining the amount of rotation of the rotation sensed element fixed to the flange, which is determined by detecting the magnetic field of the rotation sensed element by the sensing elements of the measurement sensor, such as, for example, Hall Effect sensors, of the system.

Assembly includes MCU that can be operably coupled to one or more of dose sensors 1402A-E, memory 1408, identification sensor 1404, counter 1414, light driver 1411 and light indicators 1412, power-on module 1406, communication module 1410, display driver/display 1416, power source 1418, and presence module 1420. Assembly 1400 may include any number of dose sensors, such as, for example, five magnetic sensors 1402A-E (shown) or six sensors. MCU is configured to determine the total units of rotation. MCU may be configured via the presence module 1420, shown in this embodiment to be optional by dashed lines, to determine via the triggering of the presence switch system whether the module is coupled to the device's button. MCU is configured to determine the color of the dose button via the identification sensor 1404, and in some examples, associate the color data determined onboard, or off board with an external device, the color corresponding to a particular medication. MCU is configured to determine triggering of the wake-up switch in order to power on the electronic assembly for use, shown as power-on module 1406. In one example, the total rotation may be communicated to an external device that includes a memory having a database, look up table, or other data stored in memory to correlate the total rotational units to an amount of medication delivered for a given medication identified. In another example, MCU's may be configured to determine the amount of medication delivered. MCU may be operative to store the detected dose in local memory 1408 (e.g., internal flash memory or on-board EEPROM). MCU is further operative to wirelessly transmit a signal representative of device data, such as, for example, (any one or any combination thereof) the rotational units, medication identification (such as color) data, timestamp, time since last dose, battery charge status, module identification number, time of module attachment or detachment, time of inactivity, and/or other errors (such as for example dose detection and/or transmission error, medication identification detection and/or transmission error), to a paired remote electronic device, such as a user's smartphone, over a Bluetooth low energy (BLE) or other suitable short or long-range wireless communication protocol module 1410, such as, for example, near-field communication (NFC), WIFI, or cellular network. Illustratively, the BLE control logic and MCU are integrated on a same circuit. In one example, any of the modules described herein, such as module 600, may include the display module 1420, shown in this embodiment to be optional by dashed lines, for indication of information to a user. Such a display, which may be LEDs, LCD, or other digital or analog displays, may be integrated with proximal portion finger pad. MCU includes a display driver software module and control logic operative to receive and processed sensed data and to display information on said display, such as, for example, dose setting, dosed dispensed, status of injection, completion of injection, date and/or time, or time to next injection. In another example, MCU includes a LED driver 1411 coupled to one or more LEDS 1412, such as, for example, RGB LED, Orange LED and Green LED, used to communicate by sequences of on-off and different colors to the patient of whether data was successfully transmitted, whether the battery charge is high or low, or other clinical communications. Counter 1414 is shown as a real time clock (RTC) that is electronically coupled to the MCU to track time, such as, for example, dose time. Counter 1414 may also be a time counter that tracks seconds from zero based on energization. The time or count value may be communicated to the external device.

The dose detection systems have been described by way of example with particular designs of a medication delivery device, such as a pen injector. However, the illustrative dose detection systems may also be used with alternative medication delivery devices, and with other sensing configurations, operable in the manner described herein. For example, any one or more of the various sensing and switch systems may be omitted from the module.

While the invention has been illustrated and described in detail in the drawings and foregoing description, the same is to be considered as illustrative and not restrictive in character. For example, device sensing module can sense dose setting amounts if adapted to work with a device portion having suitable parts that experience relative rotation during dose setting. This application is therefore intended to cover any variations, uses or adaptations of the invention using its general principles. Further, this application is intended to cover such departures from the present disclosure as come within known or customary practice in the art to which this invention pertains. All changes, equivalents, and modifications that come within the spirit of the inventions defined by the claims included herein are desired to be protected.

Various aspects are described in this disclosure, which include, but are not limited to, the following aspects:

1. A medication delivery device including a device body; a dose setting component coupled to the device body and rotatable relative to the device body in relation to an amount of a set or delivered dose, the dose setting component having a proximal surface; an annular sensed element positioned on the proximal surface of the dose setting component; and a carrier including a proximal overlapping support contactable against the annular sensed element opposite the proximal surface of the dose setting component, the carrier being axially and rotationally fixed to the dose setting component.

2. The medication delivery device of aspect 1 in which the carrier is secured to the dose setting component at a location distal of the annular sensed element.

3. The medication delivery device of any one of aspects 1-2 in which the carrier includes a plurality of legs extending distally from the support, wherein the dose setting component includes a flange that includes axial slots to receive a portion of the legs to rotationally lock the carrier with the flange.

4. The medication delivery device of any one of aspects 1-3 wherein the annular sensed element is an annular magnet.

5. The medication delivery device of any one of aspects 1-4 wherein the annular sensed element is coupled to the dose setting component with the carrier without an adhesive.

6. The medication delivery device of any one of aspects 1-5 including a dose button coupled to an end of the device body, and a spring disposed between the dose button and the dose setting component to bias the carrier away from the dose button.

7. The medication delivery device of aspect 6 including a dose detection system coupled to the dose button.

8. The medication delivery device of aspect 7 wherein the dose detection system includes a plurality of sensors to detect movement of the annular sensed element.

9. The medication delivery device of aspect 8 wherein the dose detection system is housed in a module that is removably attached to the dose button.

10. The medication delivery device of aspect 9 wherein the module includes a plurality of arms to engage a sidewall of the dose button.

11. The medication delivery device of aspect 8 wherein the dose detection system is housed in the dose button.

12. The medication delivery device of any one of aspects 1-11 wherein the carrier includes a tubular body sized to fit within the annular sensed element.

13. The medication delivery device of aspect 12 wherein the tubular body includes a radial lip positioned distal to the proximal overlapping support.

14. A medication delivery device including: device body; a flange coupled to the device body and rotatable relative to the device body in relation to an amount of a set or delivered dose, the flange having a proximal surface; an annular magnetic element positioned on the proximal surface of the flange; and a carrier including a proximal support overlapping the annular magnetic element opposite the proximal surface of the flange, the carrier being axially and rotationally fixed to the flange.

15. The medication delivery device of aspect 14 in which the carrier is secured to the flange at a location distal of the annular magnetic element.

16. The medication delivery device of any one of aspects 14-15 wherein the carrier includes a tubular body sized to fit within the annular sensed element 17. The medication delivery device of any one of aspects 14-16 in which the carrier includes a plurality of legs extending distally from the proximal support to couple to the flange.

18. The medication delivery device of any one of aspects 14-17 wherein the annular magnetic element is an annular bipolar magnet.

19. The medication delivery device of any one of aspects 1-18 wherein the device body includes a cartridge and a medication contained within the cartridge.

20. A method of coupling a sensed element to a dose setting component of a medication delivery device, the dose setting component having a proximal surface, including: providing a carrier and an annular sensed element, the carrier including a tubular body sized to fit within the annular sensed element, a proximal lip extending radially beyond the tubular body, and a plurality of coupling legs extending distally from the tubular body away from the proximal lip; coupling the annular sensed element over the tubular body of the carrier and in contact underneath the proximal lip; and coupling the carrier with the annular sensed element to the dose setting component for sandwiching the annular sensed element between the radial lip and the proximal surface of the dose setting component, where the coupling legs of the carrier is engaged with the dose setting component to rotationally lock the carrier with the annular sensed element to the dose setting component.

We claim:

1. A medication delivery device to receive a dose detection system, the medication delivery device comprising:
a device body;
a dose setting component coupled to said device body and rotatable relative to said device body in relation to an amount of a set or delivered dose, said dose setting component having a proximal surface;
an annular sensed element to be detected by the dose detection system when attached to the medication delivery device, the annular sensed element having a proximal surface and a distal surface, the distal surface of the annular sensed element positioned on the proximal surface of said dose setting component; and
a carrier including a proximal overlapping support contactable against the proximal surface of said annular sensed element, said carrier being axially and rotationally fixed to said dose setting component.

2. The medication delivery device of claim 1 in which the carrier is secured to said dose setting component at a location distal of said annular sensed element.

3. The medication delivery device of claim 1 in which the carrier comprises a plurality of legs extending distally from said proximal overlapping support, wherein the dose setting component comprises a flange that includes axial slots to receive a portion of said legs to rotationally lock the carrier with the flange.

4. The medication delivery device of claim 1 wherein the annular sensed element is an annular magnet.

5. The medication delivery device of claim 1 wherein said annular sensed element is coupled to the dose setting component with the carrier without an adhesive.

6. The medication delivery device of claim 1 including a dose button coupled to an end of the device body, and a spring disposed between the dose button and the dose setting component to bias said carrier away from said dose button.

7. The medication delivery device of claim 6 including a dose detection system coupled to the dose button.

8. The medication delivery device of claim 7 wherein the dose detection system includes a plurality of sensors to detect movement of the annular sensed element.

9. The medication delivery device of claim 8 wherein the dose detection system is housed in a module that is removably attached to the dose button.

10. The medication delivery device of claim 9 wherein the module includes a plurality of arms to engage a sidewall of the dose button.

11. The medication delivery device of claim 8 wherein the dose detection system is housed in the dose button.

12. The medication delivery device of claim 1 wherein the carrier includes a tubular body sized to fit within the annular sensed element.

13. The medication delivery device of claim 12 wherein the tubular body includes a radial lip positioned distal to the proximal overlapping support.

14. The medication delivery device of claim 1 wherein the device body includes a cartridge and a medication contained within said cartridge.

15. A medication delivery device comprising:
a device body;
a flange coupled to said device body and rotatable relative to said device body in relation to an amount of a set or delivered dose, said flange having a proximal surface;
an actuator having a proximal face, the proximal face disposed proximal to the proximal surface of said flange;
an annular magnetic element positioned on the proximal surface of said flange; and
a carrier including a proximal support overlapping a proximal portion of said annular magnetic element, said carrier being axially and rotationally fixed to said flange.

16. The medication delivery device of claim 15 in which the carrier is secured to said flange at a location distal of said annular magnetic element.

17. The medication delivery device of claim 16 wherein the carrier includes a tubular body sized to fit within the annular magnetic element.

18. The medication delivery device of claim 17 in which the carrier comprises a plurality of legs extending distally from said proximal support to couple to the flange.

19. The medication delivery device of claim 15 wherein the annular magnetic element is an annular bipolar magnet.

20. A method of coupling an annular sensed element to a dose setting component of a medication delivery device, said dose setting component having a proximal surface, comprising:

providing a carrier and an annular sensed element, the carrier including a tubular body sized to fit within the annular sensed element, a proximal lip extending radially beyond the tubular body, and a plurality of coupling legs extending distally from said tubular body away from the proximal lip;
coupling the annular sensed element over the tubular body of said carrier and in contact underneath the proximal lip; and
coupling the carrier with the annular sensed element to the dose setting component for sandwiching the annular sensed element between the proximal lip and the proximal surface of the dose setting component, where the coupling legs of the carrier is engaged with the dose setting component to rotationally lock the carrier with the annular sensed element to the dose setting component.

21. A medication delivery device comprising:
a device body;
an actuator coupled to said device body, the actuator having a proximal face;
a dose setting component coupled to said device body, the dose setting component rotatable relative to said device body during dose setting and/or delivery;
an annular sensed element rotationally fixed to said dose setting component, a proximal surface of the annular sensed element being distal to the proximal face of the actuator; and
a carrier axially and rotationally fixed to said dose setting component, wherein the annular sensed element is disposed between a portion of the carrier and the dose setting component.

22. The medication delivery device of claim 21 wherein the annular sensed element comprises one or more magnetic dipoles.

23. The medication delivery device of claim 22 including a dose detection system coupled to the actuator, the dose detection system having one or more magnetic sensors configured to detect a magnetic field of the annular sensed element.

24. The medication delivery device of claim 21 including a dose detection system coupled to the actuator, the dose detection system configured to detect a sensed parameter of the annular sensed element.

25. The medication delivery device of claim 21 wherein the device body includes a cartridge and a medication contained within said cartridge.

\* \* \* \* \*